United States Patent
Diehl et al.

(10) Patent No.: US 9,562,097 B2
(45) Date of Patent: Feb. 7, 2017

(54) USE OF ANTI-CD83 AGONIST ANTIBODIES FOR TREATING AUTOIMMUNE DISEASES

(75) Inventors: Lauri Diehl, South San Francisco, CA (US); Jennifer Bates, South San Francisco, CA (US); Tao Sai, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 368 days.

(21) Appl. No.: 14/129,053

(22) PCT Filed: Jun. 29, 2012

(86) PCT No.: PCT/US2012/045142
§ 371 (c)(1),
(2), (4) Date: May 23, 2014

(87) PCT Pub. No.: WO2013/006505
PCT Pub. Date: Jan. 10, 2013

(65) Prior Publication Data
US 2014/0286950 A1 Sep. 25, 2014

Related U.S. Application Data

(60) Provisional application No. 61/504,127, filed on Jul. 1, 2011.

(30) Foreign Application Priority Data

Dec. 27, 2011 (JP) ................................ 2011-285585

(51) Int. Cl.
*A61K 39/395* (2006.01)
*C07K 16/28* (2006.01)
*A61K 39/00* (2006.01)

(52) U.S. Cl.
CPC ..... *C07K 16/2803* (2013.01); *A61K 2039/505* (2013.01); *C07K 2317/75* (2013.01); *C07K 2319/30* (2013.01)

(58) Field of Classification Search
None
See application file for complete search history.

(56) References Cited

U.S. PATENT DOCUMENTS

| | | |
|---|---|---|
| RE30,985 E | 6/1982 | Cartaya |
| 4,419,446 A | 12/1983 | Howley et al. |
| 4,560,655 A | 12/1985 | Baker |
| 4,601,978 A | 7/1986 | Karin |
| 4,657,760 A | 4/1987 | Kung et al. |
| 4,657,866 A | 4/1987 | Kumar |
| 4,676,980 A | 6/1987 | Segal et al. |
| 4,767,704 A | 8/1988 | Cleveland et al. |
| 4,816,567 A | 3/1989 | Cabilly et al. |
| 4,927,762 A | 5/1990 | Darfler |
| 4,965,199 A | 10/1990 | Capon et al. |
| 5,122,469 A | 6/1992 | Mather et al. |
| 5,206,344 A | 4/1993 | Katre et al. |
| 5,225,212 A | 7/1993 | Martin et al. |
| 5,229,275 A | 7/1993 | Goroff |
| 5,545,806 A | 8/1996 | Lonberg et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,569,825 A | 10/1996 | Lonberg et al. |
| 5,571,894 A | 11/1996 | Wels et al. |
| 5,573,905 A | 11/1996 | Lerner et al. |
| 5,587,458 A | 12/1996 | King et al. |
| 5,591,669 A | 1/1997 | Krimpenfort et al. |
| 5,625,126 A | 4/1997 | Lonberg et al. |
| 5,633,425 A | 5/1997 | Lonberg et al. |
| 5,641,870 A | 6/1997 | Rinderknecht et al. |
| 5,648,237 A | 7/1997 | Carter et al. |
| 5,661,016 A | 8/1997 | Lonberg et al. |
| 5,731,168 A | 3/1998 | Carter et al. |
| 5,739,277 A | 4/1998 | Presta et al. |
| 5,789,199 A | 8/1998 | Joly et al. |
| 5,840,523 A | 11/1998 | Simmons et al. |
| 5,869,046 A | 2/1999 | Presta et al. |
| 6,075,181 A | 6/2000 | Kucherlapati et al. |
| 6,150,584 A | 11/2000 | Kucherlapati et al. |
| 6,982,321 B2 | 1/2006 | Winter |
| 7,087,409 B2 | 8/2006 | Barbas et al. |
| 2006/0140936 A1* | 6/2006 | Goldenberg ........ A61K 49/0002 424/133.1 |
| 2008/0299122 A1* | 12/2008 | Garcia-Martinez ............ C07K 16/2803 424/137.1 |

FOREIGN PATENT DOCUMENTS

| | | |
|---|---|---|
| EE | 266710 A3 | 4/1989 |
| EM | 0 183 070 A2 | 6/1986 |

(Continued)

OTHER PUBLICATIONS

Uzzaman et al. Allergy and Asthma Proceedings 2012, vol. 33, No. 3, p. s96-s99.*
Armour, K.L. et al. (Dec. 2003). "Differential Binding to Human FcgammaRIIa and FcgammaRIIb Receptors by Human IgG Wildtype and Mutant Antibodies," *Mol. Immunol.* 40:585-593.
Barbas, C.F. et al. (Apr. 26, 1994). "In vitro Evolution of a Neutralizing Human Antibody to Human Immunodeficiency Virus Type 1 to Enhance Affinity and Broaden Strain Cross-Reactivity," *Proc. Nat. Acad. Sci. USA* 91(9):3809-3813.
Barnes, D. et al. (1980). "Methods for Growth of Cultured Cells in Serum-Free Medium," *Anal. Biochem.* 102:255-270.
Boerner, P. et al. (1991). "Production of Antigen-Specific Human Monoclonal Antibodies From in Vitro-primed Human Splenocytes," *J. Immunol.* 147(1):86-95.
Bourgon, R. et al. (May 25, 2010). "Independent Filtering Increases Detection Power for High-Throughput Experiments," *Proc. Natl. Acad. Sci. USA* 107(21):9546-9551.

(Continued)

*Primary Examiner* — Ilia Ouspenski
(74) *Attorney, Agent, or Firm* — Morrison & Foerster LLP

(57) ABSTRACT

This invention relates to compositions comprising anti-CD83 agonist antibodies and methods of treating autoimmune disorders (such as inflammatory bowel disease) with anti-CD83 agonist antibodies, as well as articles of manufacture comprising anti-CD83 agonist antibodies.

21 Claims, 30 Drawing Sheets

(56) References Cited

FOREIGN PATENT DOCUMENTS

| | | |
|---|---|---|
| EP | 0 183 070 A3 | 6/1986 |
| EP | 0 183 070 B1 | 6/1986 |
| EP | 0 244 234 A2 | 11/1987 |
| EP | 0 244 234 A3 | 11/1987 |
| EP | 0 244 234 B1 | 11/1987 |
| EP | 0 244 234 B2 | 11/1987 |
| EP | 0 308 936 A2 | 3/1989 |
| EP | 0 402 226 A1 | 12/1990 |
| EP | 0 404 097 A2 | 12/1990 |
| EP | 0 404 097 A3 | 12/1990 |
| EP | 0 404 097 B1 | 12/1990 |
| EP | 0 073 657 B1 | 3/1993 |
| JP | 2005-519586 A | 7/2005 |
| JP | 2015-511931 A | 4/2015 |
| WO | WO-87/00195 A1 | 1/1987 |
| WO | WO-90/03430 A1 | 4/1990 |
| WO | WO-90/13646 A1 | 11/1990 |
| WO | WO-91/00360 A1 | 1/1991 |
| WO | WO-91/10741 A1 | 7/1991 |
| WO | WO-92/20373 A1 | 11/1992 |
| WO | WO-93/08829 A1 | 5/1993 |
| WO | WO-93/11161 A1 | 6/1993 |
| WO | WO-93/16185 A2 | 8/1993 |
| WO | WO-93/16185 A3 | 8/1993 |
| WO | WO-94/04690 A1 | 3/1994 |
| WO | WO-94/04690 C1 | 3/1994 |
| WO | WO-94/11026 A2 | 5/1994 |
| WO | WO-94/11026 A3 | 5/1994 |
| WO | WO-96/27011 A1 | 9/1996 |
| WO | WO-96/33735 A1 | 10/1996 |
| WO | WO-96/34096 A1 | 10/1996 |
| WO | WO-97/17852 A1 | 5/1997 |
| WO | WO-98/24893 A2 | 6/1998 |
| WO | WO-98/24893 A3 | 6/1998 |
| WO | WO-99/58572 A1 | 11/1999 |
| WO | WO-03/045318 A2 | 6/2003 |
| WO | WO-2004/016284 A1 | 2/2004 |
| WO | WO-2004/048552 A2 | 6/2004 |
| WO | WO-2013/006505 A1 | 1/2013 |

OTHER PUBLICATIONS

Brennan, M. et al. (Jul. 5, 1985). "Preparation of Bispecific Antibodies by Chemical Recombination of Monoclonal Immunoglobulin $G_1$ Fragments," *Science* 229:81-83.

Brodeur, B.R. et al. (1987). "Mouse-Human Myeloma Partners for the Production of Heterohybridomas," Chapter 4 in *Monoclonal Antibody Production Techniques and Applications*, Marcel Dekker, Inc.: New York, New York, pp. 51-73.

Brüggemann, M. et al. (1993). "Designer Mice: The Production of Human Antibody Repertoires in Transgenic Animals,"*Year in Immuno.* 7:33-40.

Carter, P. et al. (Feb. 1992). "High Level *Escherichia coli* Expression and Production of a Bivalent Humanized Antibody Fragment," *Bio/Technology* 10:163-167.

Carter, P. et al. (May 1992). "Humanization of an Anti-p185$^{HER2}$ Antibody for Human Cancer Therapy," *Proc. Natl. Acad. Sci. USA* 89:4285.

Chen, Y. et al. (1999). "Selection and Analysis of an Optimized Anti-VEGF Antibody: Crystal Structure of an Affinity-Matured Fab in Complex with Antigen," *J. MoL Biol.* 293:865-881.

Chothia, C. et al. (1987). "Canonical Structures for the Hypervariable Regions of Immunoglobulins," *J. Mol. Biol.* 196:901-917.

Clackson, T. et al. (Aug. 15, 1991). "Making Antibody Fragments Using Phage Display Libraries," *Nature* 352:624-628.

Cole, S.P.C. et al. (1985). "The EBV-Hybridoma Technique and its Application to Human Lung Cancer," in *Monoclonal Antibodies and Cancer Therapy Proceedings of the Roche-UCLA Symposium*, Park City, UT, Jan. 26-Feb. 2, 1985, Reisfeld, R.A. et al. Eds., p. 77-96.

Crowley, C.W. et al. (Jun. 1, 1993). "Prevention of Metastasis bu Inhibition of the Urokinase Receptor," *Proc. Natl. Acad. Sci. USA* 90(11):5021-5025.

Cunningham, B.C. et al. (Jun. 2, 1989). "High-Resolution Epitope Mapping of hGH-Receptor Interactions by Alanine-Scanning Mutagenesis," *Science* 244:1081-1085.

Fellouse, F.A. et al. (Aug. 24, 2004). "Synthetic Antibodies From a Four-Amino-Acid Code: A Dominant Role for Tyrosine in Antigen Recognition," *Proc. Natl. Acad. Sci. USA* 101(34):12467-12472.

Fishwild, D.M. et al. (Jul. 1996). "High-avidity Human IgGκ Monoclonal Antibodies From a Novel Strain of Minilocus Transgenic Mice," *Nature Biotechnol.* 14:845-851.

Fleer, R. et al. (Oct. 1991). "Stable Multicopy Vectors for High-Level Secretion of Recombinant Human Serum Albumin by *Kluyveromyces* Yeasts," *Bio/Technology* 9:968-975.

Fujimoto, Y. et al. (Mar. 22, 2002). "CD83 Expression Influences CD4+ T Cell Development," *Cell* 108:755-767.

Gerngross, T.U. (Nov. 2004). "Advances in the Production of Human Therapeutic Proteins in Yeasts and Filamentous Fungi," *Nat. Biotech.* 22(11):1409-1414.

Goding, J.W. (1983). "Production of Monoclonal Antibodies," Chapter 3 in *Monoclonal Antibodies: Principles and Practice*, Academic Press., pp. 56-103, Table of Contents pp. vii-ix.

Graham, T.L. et al. (1977). "Characteristics of a Human Cell Line Transformed by DNA From Human Adenovirus Type 5," *J. Gen. Virol.* 36:59-72.

Griffiths, A.D. et al. (1993). "Human Anti-Self Antibodies with High Specificity From Phage Display Libraries," *EMBO J.* 12(2):725-734.

Gruber, M. et al. (1994). "Efficient Tumor Cell Lysis Mediated by a Bispecific Single Chain Antibody Expressed in *Escherichia coli*," *J. Immunol.* 152:5368-5374.

Guss, B. et al. (1986). Structure of the IgG-Binding Regions of Streptococcal Protein G,' *EMBO J.* 5(7):1567-1575.

Ham, R.G. et al. (1979). "Media and Growth Requirement," Chapter 5 in *Methods in Enzymology*, Academic Press, Inc. 58:44-93.

Hamers-Casterman, C. et al. (Jun. 3, 1993). "Naturally Occurring Antibodies Devoid of Light Chains," *Nature* 363:446-448.

Hammerling, G.J. et al. Eds. (1981). "Monoclonal Antibodies and T-Cell Hybridomas,"Chapter 12 In *Research Monographs in Immunology* Elsevier: New York, NY, 3:563-681.

Harris, W.J. (1995). "Therapeutic Monoclonals," *Biochem. Soc. Transactions* 23:1035-1038.

Hawkins, R.E. et al. (1992). "Selection of Phage Antibodies by Binding Affinity: Mimicking Affinity Maturation," *J. Mol. Biol.* 226:889-896.

Holliger, P. et al. (Jul. 1993). "'Diabodies': Small Bivalent and Bispecific Antibody Fragments," *Proc. Natl. Acad. Sci. USA* 90:6444-6448.

Hongo, J-A.S. et al. (1995). "Deveopment and Characterization of Murine Monoclonal Antibodies to the Latency-Associated Peptide of Transforming Growth Factor $β_1$," *Hybridoma* 14(3):253-260.

Hoogenboom, H.R. et al. (1992). "By-Passing Immunisation: Human Antibodies From Synthetic Repertoires of Germline $V_H$ Gene Segments Rearranged in Vitro," J. Mol. Biol. 227:381-388.

Hurle, M.R. et al. (1994). "Protein Engineering Techniques for Antibody Humanization," *Curr. Opin. Biotech.* 5:428-433.

International Search Report mailed Oct. 12, 2012, for PCT Application No. PCT/US2012/045142, filed Jun. 29, 2012, six pages.

Jackson, J.R. et al. (1995). "In Vitro Antibody Maturation," *J. Immunol.* 154(7):3310-3319.

Jakobovits, A. et al. (Mar. 18, 1993). "Germ-line Transmission and Expression of a Human-Derived Yeast Artificial Chromosome," *Nature* 362:255-258.

Jakobovits, A. et al. (Mar. 1993). "Analysis of Homozygous Mutant Chimeric Mice: Deletion of the Immunoglobulin Heavy-Chain Joining Region Blocks B-Cell Development and Antibody Production," *Proc. Natl. Acad. Sci. USA* 90:2551-2555.

Johnson, K.S. et al. (1993). "Human Antibody Engineering," *Curr. Opin. Struct. Biol.* 3:564-571.

Johnson, G. et al. (2003). "The Kabat Database and a Bioinformatics Example," Chapter 2 In *Methods in Molecular Biology: Anti-*

(56) References Cited

OTHER PUBLICATIONS body Engineering: Methods and Protocols, Lo, B.K.C. Ed., Humana Press: Totowa, NJ, 248:11-25.
Jones, E.W. (Jan. 1977). "Proteinases Mutants of *Saccharomyces cerevisiae*," *Genetics* 85:23-33.
Jones, P.T. et al. (May 29, 1986). "Replacing the Complementarity-Determining Regions in a Human Antibody With Those From a Mouse," *Nature* 321:522-525.
Kohler, G. et al. (Aug. 7, 1975). "Continuous Cultures of Fused Cells Secreting Antibody of Predefined Specificity," *Nature* 256:495-497.
Kostelny, S.A. et al. (Mar. 1, 1992). "Formation of a Bispecific Antibody by the Use of Leucine Zippers," *J. Immunol.* 148(5):1547-1553.
Kotzor, N. et al. (2004). "The Soluble Form of CD83 Dramatically Changes the Cytoskeleton of Dendritic Cells," *Immunobiology* 209(1-2):129-140.
Kozbor, D. (Dec. 1984). "A Human Hybrid Myeloma for Production of Human Monoclonal Antibodies," *J. Immunol.* 133(6):3001-3005.
Lee, C.V. et al. (2004). "Bivalent Antibody Phage Display Mimics Natural Immunoglobulin," *J. Immunol. Methods* 284(1-2):119-132.
Lee, C.V. et al. (2004). "High-Affinity Human Antibodies From Phage-displayed Synthetic Fab Libraries with a Single Framework Scaffold," *J. Mol. Biol.* 340(5):1073-1093.
Li, H. et al. (Feb. 2006, e-pub. Jan. 22, 2006). "Optimization of Humanized IgGs in Glycoengineered Pichia Pastoris," *Nat. Biotech.* 24(2):210-215.
Li, J. et al. (Mar. 7, 2006). "Human Antibodies for Immunotherapy Development Generated via a Human B Cell Hybridoma Technology," *Proc. Natl. Acad. Sci. USA* 103(10):3557-3562.
Lindmark, R. et al. (1983). "Binding of Immunoglobulins to Protein A and Immunoglobulin Levels in Mammalian Sera," *J. Immunol. Meth.* 62:1-13.
Lodes, M.J. et al. (May 2004). "Bacterial Flagellin is a Dominant Antigen in Crohn Disease," *J. Clin. Invest.* 113(9):1296-1306.
Lonberg, N. et al. (Apr. 28, 1994). "Antigen-Specific Human Antibodies from Mice Comprising Four Distinct Genetic Modifications," *Nature* 368:856-859.
Lonberg, N. et al. (1995). "Human Antibodies From Transgenic Mice," *Intern. Rev. Immunol.* 13:65-93.
Marks, J.D. et al. (1991). "By-Passing Immunization: Human Antibodies from V-gene Libraries Displayed on Phage," *J. Mol. Biol.* 222:581-597.
Marks, J.D. et al. (Jul. 1992). "By-Passing Immunization: Building Affinity Human Antibodies by Chain Shuffling," *Bio/Technology* 10:779-783.
Mather, J.P. (1980). "Establishment and Characterization of Two Distinct Mouse Testicular Epithelial Cell Lines," *Biol. Reprod.* 23:243-251.
Mather, J.P. et al. (1982). "Culture of Testicular Cells in Hormone-Supplemented Serum-Free Medium," *Annals NY Acad. Sci.* 383:44-68.
McCafferty, J. et al. (Dec. 6, 1990). "Phage Antibodies: Filamentous Phage Displaying Antibody Variable Domains," *Nature* 348:552-554.
Miller, S.D. et al. (My 2007). "Experimental Autoimmune Encephalomyelitis in the Mouse," Chapter 15 in *Current Protocols in Immunology*, Unit 15.1, 26 pages.
Milstein, C. et al. (Oct. 6, 1983). "Hybrid Hybridomas and Their Use in Immunohistochemistry," *Nature* 305:537-539.
Mordenti, J. et al. (1989). "The Use of Interspecies Scaling in Toxicokinetics," In *Toxicokinetics and New Drug Development*, Yacobi et al. Eds., Pergamon Press: New York, pp. 42-46.
Morimoto, K. et al. (1992). "Single-Step Purification of F(ab')$_2$ Fragments of Mouse Monoclonal Antibodies (Immunoglobulins G1) by Hydrophobic Interaction High Performance Liquid Chromatography Using TSKgel Phenyl-5PW," *Journal of Biochemical and Biophysical Methods* 24:107-117.
Morrison, S.L. (Apr. 28, 1994). "Success in Specification," *Nature* 368:812-813.
Morrison, S.L. et al. (Nov. 1984). "Chimeric Human Antibody Molecules: Mouse Antigen-Binding Domains with Human Constant Region Domains," *Proc. Natl. Acad. Sci.* 81:6841-6855.
Munson, P.J. et al. (1980). "Ligand: A Versatile Computerized Approach for Characterization of Ligand-Binding Systems," *Anal. Biochem.* 107:220-239.
Neuberger, M. (Jul. 1996). "Generating High-Avidity Human Mabs in Mice," *Nature Biotechnol.* 14:826.
Plückthun, A. (1992). "Mono- and Bivalent Antibody Fragments Produced in *Escherichia coli*: Engineering, Folding and Antigen Binding," *Immunol Revs.* 130:151-188.
Plückthun, A. (1994). "Antibodies from *Escherichia coli*," Chapter 11 in *The Pharmacology Of Monoclonal Antibodies* Rosenburg et al. eds., Springer-Verlag, New York, 113:269-315.
Presta, L.G. (1992). "Antibody Engineering," *Curr. Op. Struct. Biol.* 2:593-596.
Presta, L.G. et al. (Sep. 1, 1993). "Humanization of an Antibody Directed Against IgE," *J. Immunol.* 151 (5):2623-2632.
Presta, L.G. et al. (Oct. 15, 1997). "Humanization of an Anti-Vascular Endothelial Growth Factor Monoclonal Antibody for the Therapy of Solid Tumors and Other Disorders," *Cancer Res.* 57:4593-4599.
Reddy, M.P. et al. (Feb. 15, 2000). "Elimination of Fc Receptor-Dependent Effector Functions of a Modified IgG4 Monoclonal Antibody to Human CD4," *J. Immunol.* 164(4):1925-1933.
Reyes, G.R. et al. (Jun. 17, 1982). "Expression of Human β-interferon cDNA Under the Control of a Thymidine Kinase Promoter from Herpes Simplex Virus," *Nature* 297:598-601.
Riechmann, L. et al. (Mar. 24, 1988). "Reshaping Human Antibodies for Therapy," *Nature* 332:323-329.
Scheinin, T. et al. (2003). "Validation of the interleukin-10 knockout mouse model of colitis: antitumour necrosis factor-antibodies suppress the progression of colitis", *Clin. Exp. Immunol.* 133:38-43.
Schier, R. et al. (1996). "Identification of Functional and Structural Amino-Acid Residues by Parsimonious Mutagenesis," *Gene* 169:147-155.
Schirbel, A. et al. (2011). "Targeting the innate immune system in pediatric inflammatory bowel disease", *Expert Rev. Gastroenterol. Hepatol.* 5(1):33-41.
Sénéchal, B. et al. (Jun. 1, 2004; e-pub. Feb. 12, 2004). "Infection of the Mature Monocyte-Derived Dendritic Cells with Human Cytomegalovirus Inhibits Stimulation of T-Cell Proliferation via the Release of Soluble CD83," *Blood* 103(11):4207-4215.
Shalaby, M.R. et al. (Jan. 1, 1992)."Development of Humanized Bispecific Antibodies Reactive with Cytotoxic Lymphocytes and Tumor Cells Overexpressing the HER2 Protoonogene," *J. Exp. Med.* 175:217-225.
Sheriff, S. et al. (Sep. 1996). "Redefining the Minimal Antigen-Binding Fragment," *Nature Struct. Biol.* 3(9):733-736.
Sidhu, S.S. et al. (2004). "Phage-Displayed Antibody Libraries of Synthetic Heavy Chain Complementarity Determining Regions," *J. Mol. Biol.* 338(2):299-310.
Silva, M.A. et al. (Jul. 2008). "Dendritic Cells and Toll-like Receptors 2 and 4 in the Ileum of Crohn's Disease Patients," *Dig. Dis. Sci.* 53(7):1917-1928.
Sims, M.J. et al. (Aug. 15, 1993). "A Humanized CD18 Antibody Can Block Function Without Cell Destruction," *J. Immunol.* 151(4):2296-2308.
Skerra, A. et al. (1993). "Bacterial Expression of Immunoglobulin in Fragments," *Curr. Opinion in Immunol.* 5:256-262.
Smyth, G.K. (2004, e-pub. Feb. 12, 2004). "Linear Models and Empirical Bayes Methods for Assessing Differential Expression in Microarray Experiments," *Stat. Appl. Genet. Mol. Biol.* 3, Article 3.
Stinchcomb, D.T. et al. (Nov. 1, 1979). "Isolation and Characterisation of a Yeast Chromosomal Replicator," *Nature* 282:39-43.
Stites, et al. "Immunoglobulin Proteins," Chapter 6 in *Basic and Clincial Immunology*, 8th Edition, Appleton & Lange, Norwalk, CT, pp. 66-79 (1994).
Suresh, M.R. et al. (1986). "Bispecific Monoclonal Antibodies from Hybrid Hybridomas,"*Methods in Enzymology* 121:210-228.

(56) References Cited

OTHER PUBLICATIONS

Traunecker, A. et al. (1991). "Bispecific Single Chain Molecules (Janusins) Target Cytotoxic Lymphocytes on HIV Infected Cells," *EMBO J.* 10(12):3655-3659.

Tutt, A. et al. (Jul. 1, 1991). "Trispecific F(ab')₃ Derivatives That Use Cooperative Signaling Via the TCR/CD3 Complex and CD2 to Activate and Redirect Resting Cytotoxic T Cells" *J. Immunol.* 147:60-69.

Umeno, J. et al. (Dec. 2011, e-pub. Feb. 23, 2011). "Meta-Analysis of Published Studies Identified Eight Additional Common Susceptibility loci for Crohn's Disease and Ulcerative Colities," *Inflamm. Bowel Dis.* 17(12):2407-2415.

Urlaub, G. et al. (Jul. 1980). "Isolation of Chinese Hamster Cell Mutants Deficient in Dihydrofolate Reductase Activity," *Proc. Natl. Acad. Sci. USA* 77(7):4216-4220.

Van Den Berg, J.A. (Feb. 1990). "*Kluyveromyces* As a Host for Heterologous Gene Expression: Expression and Secretion of Prochymosin," *Bio/Technology* 8:135-139.

Van Dijk, M.A. et al. (2001). "Human Antibodies As Next Generation Therapeutics," *Curr. Opin. Chem. Biol.* 5:368-374.

Vaswani, S.K. et al. (Aug. 1998). "Humanized Antibodies as Potential Therapeutic Drugs," *Ann. Allergy, Asthma & Immunol.* 1:105-115.

Verhoeyen, M. et al. (Mar. 25, 1988). "Reshaping Human Antibodies: Grafting an Antilysozyme Activity," *Science* 239:1534-1536.

Waterhouse, P. et al. (1993). "Combinatorial Infection and in vivo Recombination: A Strategy for Making Large Phage Antibody Repertoires," *Nucl. Acids Res.* 21(9):2265-2266.

Written Opinion mailed Oct. 12, 2012, for PCT Application No. PCT/US2012/045142, filed Jun. 29, 2012, four pages.

Wu, T. et al. (2009). "The AKT Axis as a Therapeutic Target in Autoimmune Diseases," *Endocrine Metabolic & Immune Disorders—Drug Targets* 9(2):145-150.

Xu, J. L. et al. (Jul. 2000). "Diversity in the CDR3 Region of $V_H$ Is Sufficient for Most Antibody Specificities," *Immunity* 13:37-45.

Yaniv, J.M. (May 6, 1982). "Enhancing Elements for Activation of Eukaryotic Promoters," *Nature* 297:17-18.

Yazaki et al. (2003). *Methods in Molecular Biology*, Lo, B.K.C. Ed., Humana Press: Totowa, N.J., 248: 255-268.

Yelton, D.E. et al. (1995). "Affinity Maturation of the BR96 Ani-Carcinoma Antibody by Codon-Based Mutagenesis," *J. Immunol.* 155:1994-2004.

Zapata, G. et al. (1995). "Engineering Linear F(ab')2 Fragments for Efficient Production in *Escherichia coli* and Enhanced Antiproliferative Activity," *Protein Eng.* 8(10):1057-1062.

Bates, J. et al. (2011). "CD83 Regulates DC Immune Responses through a Homotypic Interaction," Abstract Supplement, *15th International Congress of Mucosal Immunology (ICMI11 2011)*, Jul. 5-9, 2011, Paris, France, Abstract No. W.78, p. 62, total 1 page.

Schirbel, A. et al. (2011). "Targeting the innate immune system in pediatric inflammatory bowel disease," *Expert Rev. Gastroenterol. Hepatol.* 5(1):33-41.

Chen et al. "Two Novel Monoclonal Antibodies Produced Against Human CD83 Molecule," *Hybridoma* 30(3):297-302, (Jun. 2011).

Pashine et al. "Failed Efficacy of Soluble Human C083-Ig in Allogeneic Mixed Lymphocyte Reactions and Experimental Autoimmune Encephalomyelitis: Implications for a Lack of Therapeutic Potential," *Immunology letters* 115(1):9-15, (Jan. 2008).

\* cited by examiner

USE OF ANTI-CD83 AGONIST ANTIBODIES FOR TREATING AUTOIMMUNE DISEASES

CROSS-REFERENCE TO RELATED PATENT APPLICATIONS

This application is a U.S. national phase patent application of PCT/US2012/045142, filed Jun. 29, 2012, which claims the benefit of U.S. Provisional Patent Application Ser. No. 61/504,127, filed Jul. 1, 2011, and Japanese Patent Application Nos. 2011-285585, filed Dec. 27, 2011, each of which is incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392009900SEQLIST.txt, date recorded: Mar. 18, 2014, size: 43 KB).

FIELD OF THE INVENTION

This invention relates to anti-CD83 agonist antibodies and methods for using anti-CD83 agonist antibodies to treat autoimmune diseases, such as inflammatory bowel disease.

BACKGROUND OF THE INVENTION

Inflammatory bowel diseases (IBD), such as ulcerative colitis and Crohn's disease, are characterized by chronic and relapsing inflammation of the intestine. Recent evidence indicates that IBD is due to a loss of tolerance to commensal intestinal flora in which the mucosal immune system can not differentiate between pathogens and commensal organisms. Therefore IBD patients develop immune recognition to normal flora which results in a gastrointestinal inflammatory response. The extent to which seroreactivity to normal flora develops is roughly correlated with disease duration and disease severity (Lodes et al., *J Clin Invest.*, 113:1296-1306, 2004). More than 25 alleles have been identified that overlap between ulcerative colitis and Crohn's disease genetics (Umeno et al., *Inflamm Bowel Dis.* In press, 2011). These IBD genetic alleles converge on several common pathways that result in 1) Defects in epithelial integrity, 2) Defects in myeloid microbial responses and production of proinflammatory cytokines, and 3) Increased T-helper 17 cell and T-helper 1 cell responses. Studies show that most IBD patients have a spontaneous relapse and remission cycle where they achieve clinical remission at reasonable frequency but do not sustain remission for extended periods. This observation indicates the existence of as yet undefined mucosal homeostatic mechanisms that may drive the IBD remission phase (Schirbel et al., *Expert Rev Gastroenterol Hepatol.*, 5(1):33-41, 2011). The identification of molecules and mechanisms involved in maintaining mucosal homeostasis would therefore be beneficial for driving as well as maintaining IBD remission.

CD83 is a highly conserved 45 kilodalton transmembrane glycoprotein that is predominantly expressed on the surface of dendritic cells and thymic epithelial cells. Additionally, CD83 is transiently expressed on the surface of other activated cells of the immune system and can also be found in a soluble form. Structural analysis of the predicted amino acid sequence of CD83 demonstrates that it is a member of the immunoglobulin super family indicating a role in the immune system. Literature reports suggests that soluble CD83 (sCD83) may play an immunomodulatory role due to the observation that sCD83 released by HCMV-infected mature dendritic cells inhibits T cell proliferation (Senechal et al., *Blood.*, 103(11):4207-4215, 2004) and that sCD83 has a morphologic effect on the dendritic cell cytoskeleton (Kotzor et al., *Immunobiology.*, 209(1-2):129-140, 2004). However, no ligand has been identified for CD83 and the function of CD83 remains poorly understood. Interestingly, CD83 gene expression is downregulated at the mucosal surface in human Crohn's disease (Silva et al., *Dig. Dis. Sci.*, 53(7):1917-1928, 2008), suggesting that CD83 may be involved in the maintenance of mucosal homeostasis and therefore be a therapeutic target for modulating the immune system in IBD.

All references cited herein, including patent applications and publications, are hereby incorporated by reference in their entirety.

SUMMARY OF THE INVENTION

Provided herein are methods for treating or preventing an autoimmune disease in an individual comprising administering to the individual an effective amount of an anti-CD83 agonist antibody. In some embodiments, the individual is a human.

In some embodiments, the autoimmune disease is selected from the group consisting of rheumatoid arthritis, juvenile rheumatoid arthritis, systemic lupus erythematosus (SLE), lupus nephritis, ulcerative colitis, Wegener's disease, inflammatory bowel disease, idiopathic thrombocytopenic purpura (ITP), thrombotic thrombocytopenic purpura (TTP), autoimmune thrombocytopenia, multiple sclerosis, psoriasis, IgA nephropathy, IgM polyneuropathies, myasthenia gravis, vasculitis, diabetes mellitus, Reynaud's syndrome, Sjorgen's syndrome and glomerulonephritis. In some embodiments, the autoimmune disease is associated with myeloid cell activation (dendritic cell and macrophage), such as multiple sclerosis and inflammatory bowel disease.

In some embodiments, the individual has or is diagnosed with an autoimmune disease. In some embodiments, the individual has or is diagnosed with inflammatory bowel disease (such as Crohn's disease, ulcerative colitis, and indeterminate colitis).

In some embodiments, the anti-CD83 agonist antibody inhibits release of a pro-inflammatory cytokine from mature dendritic cells (for example, release of pro-inflammatory cytokine MCP-1 and/or IL-12p40 are inhibited). In some embodiments, the anti-CD83 agonist antibody induces release of an anti-inflammatory cytokine from mature dendritic cells (for example, release of anti-inflammatory cytokine IL-1ra is induced). In some embodiments, the anti-CD83 agonist antibody induces a decrease of cell surface expression of CD83 and/or HLA-DR on mature dendritic cells. In some embodiments, the anti-CD83 agonist antibody inhibits activation of MAPK and/or mTOR signaling in mature dendritic cells. In some embodiments, the inhibition of the activation of MAPK signaling is measured by a decrease in phosphorylation of p38 and/or CREB proteins in mature dendritic cells. In some embodiments, the inhibition of the activation of mTOR signaling is measured by a decrease in phosphorylation of the mTOR protein in mature dendritic cells. In some embodiments, the anti-CD83 agonist antibody upregulates expression of wound healing genes (for example, vcan, spock2, and fbn2) in mature dendritic cells.

In some embodiments, the anti-CD83 agonist antibody is a monoclonal antibody. In some embodiments, the anti-CD83 agonist antibody is an antigen-binding fragment, for example, a fragment selected from the group consisting of Fab, Fab'-SH, Fv, scFv, and (Fab')$_2$ fragments. In some embodiments, the anti-CD83 agonist antibody is a humanized antibody. In some embodiments, the anti-CD83 agonist antibody is a human antibody. In some embodiments, the anti-CD83 agonist antibody is a chimeric antibody. In some embodiments, the anti-CD83 agonist antibody comprises a heavy chain variable domain comprising HVR-H1 comprising the amino acid sequence of SEQ ID NO:31, HVR-H2 comprising the amino acid sequence of SEQ ID NO:32, and HVR-H3 comprising the amino acid sequence of SEQ ID NO:33; and/or a light chain variable domain comprising HVR-L1 comprising the amino acid sequence of SEQ ID NO:37, HVR-L2 comprising the amino acid sequence of SEQ ID NO:38, and HVR-L3 comprising the amino acid sequence of SEQ ID NO:39. In some embodiments, the anti-CD83 agonist antibody comprises a heavy chain variable domain comprising the amino acid sequence of SEQ ID NO:30, and/or a light chain variable domain comprising the amino acid sequence of SEQ ID NO:36.

In some embodiments, the anti-CD83 agonist antibody is administered intravenously, intramuscularly, subcutaneously, topically, orally, transdermally, intraperitoneally, intraorbitally, by implantation, by inhalation, intrathecally, intraventricularly, or intranasally.

Also provided herein are articles of manufacture or kits comprising an anti-CD83 agonist antibody. In some embodiments, the articles or kits may further comprise a package insert comprising instructions for using the anti-CD83 agonist antibody to treat or prevent an autoimmune disease in an individual.

Also provided herein is an isolated anti-CD83 antibody comprising a variable domain comprising at least one, two, three, four, five or six hypervariable region (HVR) sequences selected from the group consisting of: (a) HVR-H1 comprising the amino acid sequence of SEQ ID NO:31; (b) HVR-H2 comprising the amino acid sequence of SEQ ID NO:32; (c) HVR-H3 comprising the amino acid sequence of SEQ ID NO:33; (d) HVR-L1 comprising the amino acid sequence of SEQ ID NO:37; (e) HVR-L2 comprising the amino acid sequence of SEQ ID NO:38; (f) HVR-L3 comprising the amino acid sequence of SEQ ID NO:39. Also provided herein is an isolated anti-CD83 antibody comprising a heavy chain variable domain and a light chain variable domain comprising the following six HVR sequences: (a) HVR-H1 comprising the amino acid sequence of SEQ ID NO:31; (b) HVR-H2 comprising the amino acid sequence of SEQ ID NO:32; (c) HVR-H3 comprising the amino acid sequence of SEQ ID NO:33; (d) HVR-L1 comprising the amino acid sequence of SEQ ID NO:37; (e) HVR-L2 comprising the amino acid sequence of SEQ ID NO:38; (f) HVR-L3 comprising the amino acid sequence of SEQ ID NO:39.

In some embodiments, the antibody comprises (a) HVR-H1 comprising the amino acid sequence of SEQ ID NO:31; (b) HVR-H2 comprising the amino acid sequence of SEQ ID NO:32, and (c) HVR-H3 comprising the amino acid sequence of SEQ ID NO:33. In some embodiments, the antibody further comprises (a) HVR-L1 comprising the amino acid sequence of SEQ ID NO:37; (b) HVR-L2 comprising the amino acid sequence of SEQ ID NO:38; and (c) HVR-L3 comprising the amino acid sequence of SEQ ID NO:39.

In some embodiments, the antibody comprises (a) HVR-L1 comprising the amino acid sequence of SEQ ID NO:37; (b) HVR-L2 comprising the amino acid sequence of SEQ ID NO:38; and (c) HVR-L3 comprising the amino acid sequence of SEQ ID NO: 39.

In some embodiments, wherein the antibody is a chimeric antibody or a humanized antibody. In some embodiments, the antibody comprises a heavy chain variable domain comprising the amino acid sequence of SEQ ID NO:30, and/or a light chain variable domain comprising the amino acid sequence of SEQ ID NO:36.

Also provided herein is a pharmaceutical composition comprising an anti-CD83 antibody described herein and a pharmaceutically acceptable carrier.

Also provided herein is an isolated nucleic acid comprising a nucleotide sequence encoding an anti-CD83 antibody described herein. Provided herein is a vector comprising the nucleic acid. In some embodiments, the vector is an expression vector. Also provided herein is a host cell comprising the vector. In some embodiments, the host cell is prokaryotic or eukaryotic.

Also provided herein is a method for making an anti-CD83 antibody, said method comprising culturing a host cell described herein under conditions suitable for expression of a nucleic acid encoding an anti-CD83 antibody described herein. In some embodiments, the method further comprises recovering the anti-CD83 antibody produced by the host cell.

It is to be understood that one, some, or all of the properties of the various embodiments described herein may be combined to form other embodiments of the present invention. These and other aspects of the invention will become apparent to one of skill in the art.

DETAILED DESCRIPTION OF THE INVENTION

I. General Techniques

Figure 1:
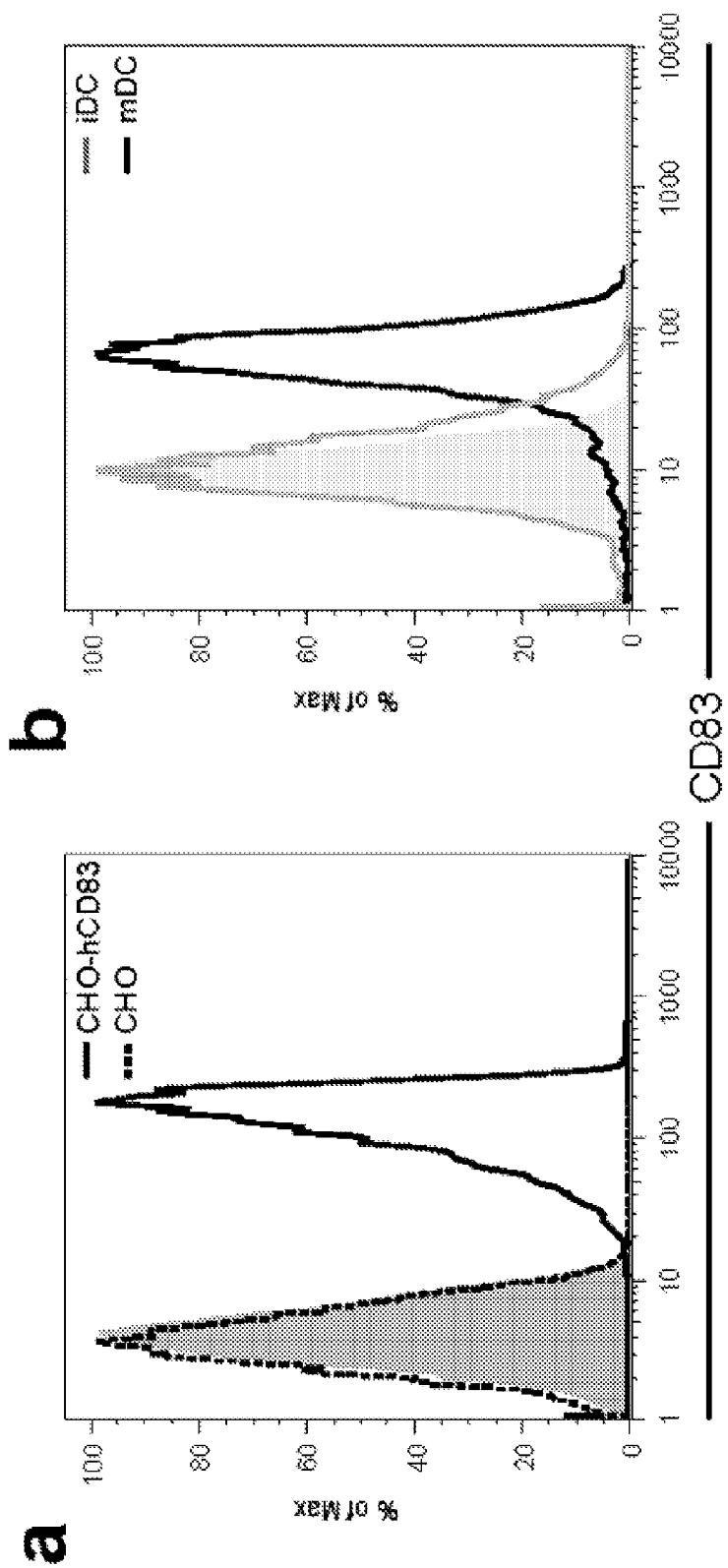
FIG. 1 shows CD83 engaged in homotypic binding at the surface of cells expressing CD83. (a) CD83 expressed on the surface of stably transfected CHO-hCD83 cells were quantified by flow cytometry. (b) Expression of CD83 expressed on MUTZ-3 derived mature DC were quantified by flow cytometry. (c and d) CD83.fc bound to CHO-hCD83 and mature DC.
Figure 1:
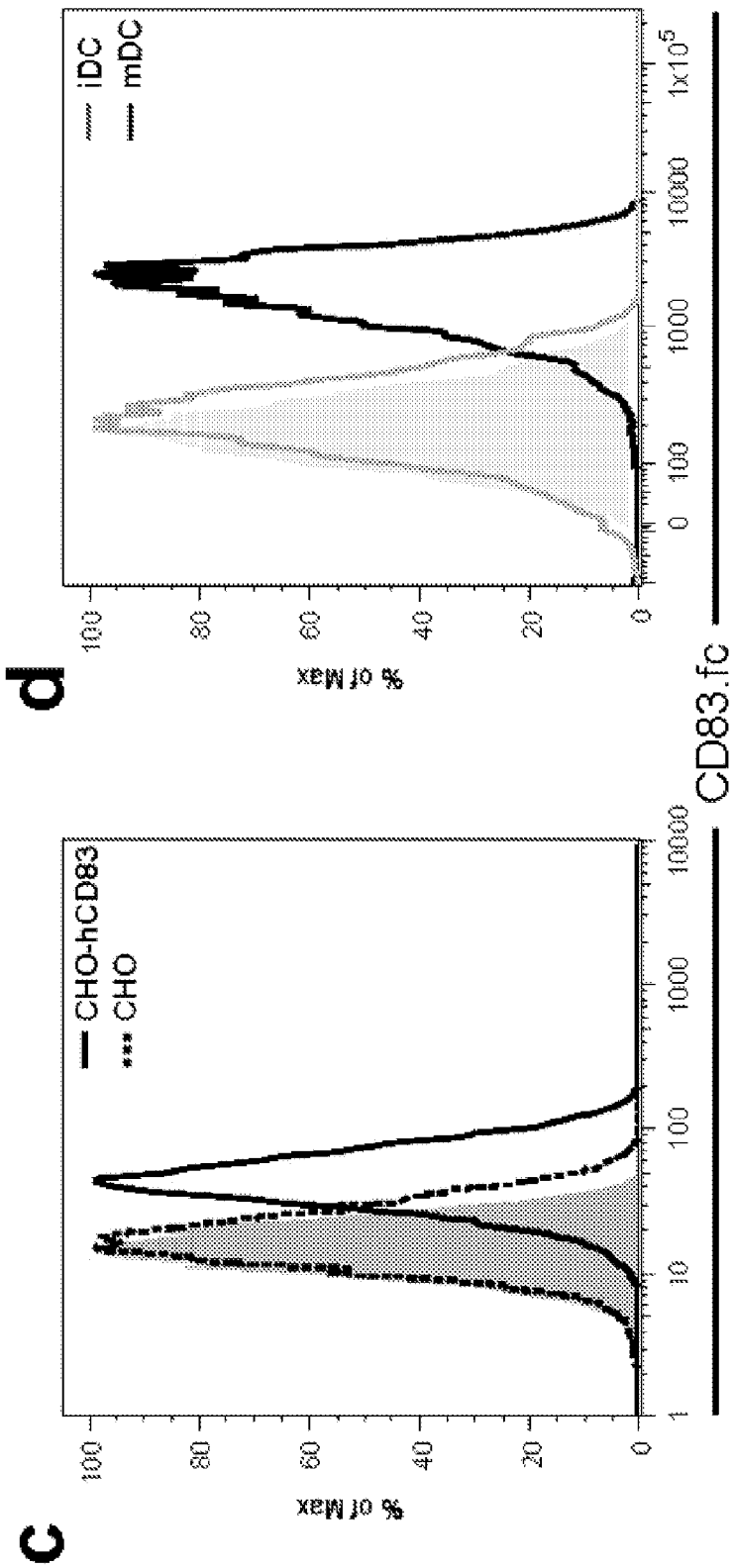

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3rd edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988) *Antibodies, A Laboratory Manual, and Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 1993).

II. Definitions

The term "autoimmune" refers to the process by which immune system components such as antibodies or lymphocytes attack or harm molecules, cells, or tissues of the organism producing them. "Autoimmune disorders" refers to diseases where damage, such as tissue damage, or pathogenesis is, at least partially, a result of an autoimmune process. By way of example, "autoimmune disease" includes rheumatoid arthritis, juvenile rheumatoid arthritis, systemic lupus erythematosus (SLE), lupus nephritis, ulcerative colitis, Wegener's disease, inflammatory bowel disease, idiopathic thrombocytopenic purpura (ITP), thrombotic thrombocytopenic purpura (TTP), autoimmune thrombocytopenia, multiple sclerosis, psoriasis, IgA nephropathy, IgM polyneuropathies, myasthenia gravis, vasculitis, diabetes mellitus, Reynaud's syndrome, Sjorgen's syndrome and glomerulonephritis. In some embodiments, the autoimmune disorder is associated with myeloid cell activation (dendritic cell and macrophage), such as multiple sclerosis and inflammatory bowel disease.

"Inflammatory bowel disease" or "IBD" refers to the group of disorders that cause the intestines to become inflamed, generally manifested with symptoms including abdominal cramps and pain, diarrhea, weight loss and intestinal bleeding. IBD includes ulcerative colitis (UC), Crohn's disease, and indeterminate colitis.

"Ulcerative colitis" or "UC" is a chronic, episodic, inflammatory disease of the large intestine and rectum characterized by bloody diarrhea. Ulcerative colitis is characterized by chronic inflammation in the colonic mucosa and can be categorized according to location: "proctitis" involves only the rectum; "proctosigmoiditis" affects the rectum and sigmoid colon; "left-sided colitis" encompasses the entire left side of the large intestine; and "pancolitis" inflames the entire colon.

"Crohn's disease," also called "regional enteritis," is a chronic autoimmune disease that can affect any part of the gastrointestinal tract but most commonly occurs in the ileum (the area where the small and large intestine meet). Crohn's disease, in contrast to ulcerative colitis, is characterized by chronic inflammation extending through all layers of the intestinal wall and involving the mesentery as well as regional lymph nodes. Whether or not the small bowel or colon is involved, the basic pathologic process is the same.

Ulcerative Colitis and Crohn's disease can be distinguished from each other clinically, endoscopically, pathologically, and serologically in more than 90% of cases; the remainder are considered to be indeterminate IBD (Harrison's Principles of Internal medicine, 12$^{th}$ edition, p. 1271 (1991)).

"Indeterminate colitis" refers to an inflammatory bowel disease condition that has overlapping features of ulcerative colitis and Crohn's disease. The diagnosis is given when histology shows acute and chronic inflammation with architectural changes confined to the colon but does not clearly indicate whether an individual has Crohn's disease or ulcerative colitis.

As used herein, the term "treatment" refers to clinical intervention designed to alter the natural course of the individual or cell being treated during the course of clinical pathology. Desirable effects of treatment include decreasing the rate of disease progression, ameliorating or palliating the disease state, and remission or improved prognosis. An individual is successfully "treated", for example, if one or more symptoms associated with an autoimmune disease (such as inflammatory bowel disease) are mitigated or eliminated.

As used herein, the term "prevention" includes providing prophylaxis with respect to occurrence or recurrence of a disease in an individual. An individual may be predisposed to, susceptible to an autoimmune disease, or at risk of developing an autoimmune disease, but has not yet been diagnosed with the disease.

As used herein, an individual "at risk" of developing an autoimmune disease may or may not have detectable disease or symptoms of disease, and may or may not have displayed detectable disease or symptoms of disease prior to the treatment methods described herein. "At risk" denotes that an individual has one or more risk factors, which are measurable parameters that correlate with development of the autoimmune disease, as known in the art. An individual having one or more of these risk factors has a higher probability of developing the disease than an individual without one or more of these risk factors.

An "effective amount" refers to at least an amount effective, at dosages and for periods of time necessary, to achieve the desired therapeutic or prophylactic result. An effective amount can be provided in one or more administrations.

A "therapeutically effective amount" is at least the minimum concentration required to effect a measurable improvement of a particular disorder (e.g., an autoimmune disease). A therapeutically effective amount herein may vary according to factors such as the disease state, age, sex, and weight of the patient, and the ability of the anti-CD83 agonist antibody to elicit a desired response in the individual. A therapeutically effective amount is also one in which any toxic or detrimental effects of the anti-CD83 agonist antibody are outweighed by the therapeutically beneficial effects. A "prophylactically effective amount" refers to an amount effective, at the dosages and for periods of time necessary, to achieve the desired prophylactic result. Typically but not necessarily, since a prophylactic dose is used in subjects prior to or at an earlier stage of disease, a prophylactically effective amount may be less than a therapeutically effective amount.

"Chronic" administration refers to administration of the medicament(s) in a continuous as opposed to acute mode, so as to maintain the initial therapeutic effect (activity) for an extended period of time. "Intermittent" administration refers to treatment that is not consecutively done without interruption, but rather is cyclic in nature.

As used herein, administration "in conjunction" with another compound or composition includes simultaneous administration and/or administration at different times. Administration in conjunction also encompasses administration as a co-formulation or administration as separate compositions, including at different dosing frequencies or intervals, and using the same route of administration or different routes of administration.

An "individual" for purposes of treatment or prevention refers to any animal classified as a mammal, including humans, domestic and farm animals, and zoo, sport, or pet animals, such as dogs, horses, rabbits, cattle, pigs, hamsters, gerbils, mice, ferrets, rats, cats, and the like. In some embodiments, the individual is human.

As used herein, the term "cytokine" refers generically to proteins released by one cell population that act on another cell as intercellular mediators or have an autocrine effect on the cells producing the proteins. Examples of such cytokines include lymphokines, monokines; interleukins ("ILs") such as IL-1, IL-1α, IL-2, IL-3, IL-4, IL-5, IL-6, IL-7, IL-8, IL-9, IL-11, IL-12, IL-13, IL-15, IL-17A-F, IL-18 to IL-29 (such as IL-23), IL-31, including PROLEUKIN® rIL-2; a tumor-necrosis factor such as TNF-α or TNF-β, TGF-β1-3; and other polypeptide factors including leukemia inhibitory factor ("LIF"), ciliary neurotrophic factor ("CNTF"), CNTF-like cytokine ("CLC"), cardiotrophin ("CT"), and kit ligand ("KL").

As used herein, the term "CD83" encompasses native sequence CD83 and naturally occurring variants of CD83. CD83 may be isolated from a variety of sources, such as from mammalian (including human) tissue types or from another source, or prepared by recombinant and/or synthetic methods.

As used herein, the term "anti-CD83 agonist antibody" refers to an antibody that binds CD83 expressed on a cell surface and activates the signal transduction of CD83 after binding to the CD83 expressed on the cell surface.

The term "immunoglobulin" (Ig) is used interchangeably with "antibody" herein. The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity.

The basic 4-chain antibody unit is a heterotetrameric glycoprotein composed of two identical light (L) chains and two identical heavy (H) chains. The pairing of a $V_H$ and $V_L$ together forms a single antigen-binding site. For the structure and properties of the different classes of antibodies, see, e.g., *Basic and Clinical Immunology*, 8th Ed., Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa ("κ") and lambda ("λ"), based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG and IgM, having heavy chains designated alpha ("α"), delta ("δ"), epsilon ("ε"), gamma ("γ") and mu ("μ"), respectively. The γ and α classes are further divided into subclasses (isotypes) on the basis of relatively minor differences in the CH sequence and function, e.g., humans express the following subclasses: IgG1, IgG2, IgG3, IgG4, IgA1 and IgA2. The subunit structures and three dimensional configurations of different classes of immunoglobulins are well known and described generally in, for example, Abbas et al., Cellular and Molecular Immunology, 4th ed. (W.B. Saunders Co., 2000).

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

An "isolated" antibody is one that has been identified, separated and/or recovered from a component of its production environment (e.g., naturally or recombinantly). Preferably, the isolated polypeptide is free of association with all other contaminant components from its production environment. Contaminant components from its production environment, such as those resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant T-cells since at least one component of the antibody's natural environment will not be present. Ordinarily, however, an isolated polypeptide or antibody will be prepared by at least one purification step.

The "variable region" or "variable domain" of an antibody refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen binding site of antibodies (see Kabat et al., *Sequences of Immunological Interest*, Fifth Edition, National Institute of Health, Bethesda, Md. (1991)). The constant domains are not involved directly in the binding of antibody to an antigen, but exhibit various effector functions, such as participation of the antibody in antibody-dependent-cellular toxicity.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein., *Nature,* 256:495-97 (1975); Hongo et al., *Hybridoma,* 14 (3):253-260 (1995), Harlow et al., *Antibodies: A Laboratory Manual,* (Cold Spring Harbor Laboratory Press, 2d ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature,* 352:624-628 (1991); Marks et al., *J. Mol. Biol.* 222:581-597 (1992); Sidhu et al., *J. Mol. Biol.* 338(2): 299-310 (2004); Lee et al., *J. Mol. Biol.* 340(5):1073-1093 (2004); Fellouse, *Proc. Nat'l Acad. Sci. USA* 101(34):12467-472 (2004); and Lee et al., *J. Immunol. Methods* 284(1-2):119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Nat'l Acad. Sci. USA* 90:2551 (1993); Jakobovits et al., *Nature* 362:255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10:779-783 (1992); Lonberg et al., *Nature* 368:856-859 (1994); Morrison, *Nature* 368:812-813 (1994); Fishwild et al., *Nature Biotechnol.* 14:845-851 (1996); Neuberger, *Nature Biotechnol.* 14:826 (1996); and Lonberg and Huszar, *Intern. Rev. Immunol.* 13:65-93 (1995).

The term "naked antibody" refers to an antibody that is not conjugated to a cytotoxic moiety or radiolabel.

The terms "full-length antibody," "intact antibody" or "whole antibody" are used interchangeably to refer to an antibody in its substantially intact form, as opposed to an antibody fragment. Specifically whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, preferably the antigen binding and/or the variable region of the intact antibody. Examples of antibody fragments include Fab, Fab', F(ab')$_2$ and Fv fragments; diabodies; linear antibodies (see U.S. Pat. No. 5,641,870, Example 2; Zapata et al., *Protein Eng.* 8(10):1057-1062 (1995)); single-chain antibody molecules and multispecific antibodies formed from antibody fragments.

Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site.

Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the C$_H$1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the V$_H$ and V$_L$ domains which enables the sFv to form the desired structure for antigen binding. For a review of the sFv, see Pluckthun in *The Pharmacology of Monoclonal Antibodies*, vol. 113, Rosenburg and Moore eds., Springer-Verlag, New York, pp. 269-315 (1994).

"Functional fragments" of the antibodies of the invention comprise a portion of an intact antibody, generally including the antigen binding or variable region of the intact antibody or the F region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the V$_H$ and V$_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the V$_H$ and V$_L$ domains of the two antibodies are present on different polypeptide chains. Diabodies are described in greater detail in, for example, EP 404,097; WO 93/11161; Hollinger et al., *Proc. Nat'l Acad. Sci. USA* 90:6444-48 (1993).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Nat'l Acad. Sci. USA*, 81:6851-55 (1984)). Chimeric antibodies of interest herein include PRIMATIZED® antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from an HVR of the recipient are replaced by residues from an HVR of a non-human species (donor antibody) such as mouse, rat, rabbit or non-human primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, and the like. The number of these amino acid substitutions in the FR is typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, for example, Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is one that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.*, 227: 381 (1991); Marks et al., *J. Mol. Biol.*, 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.*, 147(1):86-95 (1991). See also van Dijk and van de Winkel, *Curr. Opin. Pharmacol.* 5:368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Nat'l Acad.*

Sci. USA, 103:3557-3562 (2006) regarding human antibodies generated via a human B-cell hybridoma technology.

The term "hypervariable region," "HVR," or "HV," when used herein refers to the regions of an antibody-variable domain that are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu in *Methods in Molecular Biology* 248:1-25 (Lo, ed., Human Press, Totowa, N.J., 2003)). Indeed, naturally occurring camelid antibodies consisting of a heavy chain only are functional and stable in the absence of light chain. See, e.g., Hamers-Casterman et al., *Nature* 363:446-448 (1993) and Sheriff et al., *Nature Struct. Biol.* 3:733-736 (1996).

A number of HVR delineations are in use and are encompassed herein. The HVRs that are Kabat complementarity-determining regions (CDRs) are based on sequence variability and are the most commonly used (Kabat et al., supra). Chothia refers instead to the location of the structural loops (Chothia and Lesk *J. Mol. Biol.* 196:901-917 (1987)). The AbM HVRs represent a compromise between the Kabat CDRs and Chothia structural loops, and are used by Oxford Molecular's AbM antibody-modeling software. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |
| | | (Kabat Numbering) | | |
| H1 | H31-H35 | H26-H35 | H26-H32 | H30-H35 |
| | | (Chothia Numbering) | | |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2), and 89-97 or 89-96 (L3) in the VL, and 26-35 (H1), 50-65 or 49-65 (a preferred embodiment) (H2), and 93-102, 94-102, or 95-102 (H3) in the VH. The variable-domain residues are numbered according to Kabat et al., supra, for each of these extended-HVR definitions.

"Framework" or "FR" residues are those variable-domain residues other than the HVR residues as herein defined.

The phrase "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al., Sequences of Immunological Interest. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system (e.g., see U.S. Provisional Application No. 60/640,323, Figures for EU numbering).

An "acceptor human framework" as used herein is a framework comprising the amino acid sequence of a VL or VH framework derived from a human immunoglobulin framework or a human consensus framework. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less. Where pre-existing amino acid changes are present in a VH, preferable those changes occur at only three, two, or one of positions 71H, 73H and 78H; for instance, the amino acid residues at those positions may by 71A, 73T and/or 78A. In one embodiment, the VL acceptor human framework is identical in sequence to the VL human immunoglobulin framework sequence or human consensus framework sequence.

A "human consensus framework" is a framework that represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest,* 5th Ed. Public Health Service, National Institutes of Health, Bethesda, Md. (1991). Examples include for the VL, the subgroup may be subgroup kappa I, kappa II, kappa III or kappa IV as in Kabat et al., supra. Additionally, for the VH, the subgroup may be subgroup I, subgroup II, or subgroup III as in Kabat et al., supra.

A "VH subgroup III consensus framework" comprises the consensus sequence obtained from the amino acid sequences in variable heavy subgroup III of Kabat et al., supra.

A "VL subgroup I consensus framework" comprises the consensus sequence obtained from the amino acid sequences in variable light kappa subgroup I of Kabat et al., supra.

An "amino-acid modification" at a specified position, e.g., of the Fc region, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

An "affinity-matured" antibody is one with one or more alterations in one or more HVRs thereof that result in an improvement in the affinity of the antibody for antigen, compared to a parent antibody that does not possess those alteration(s). In one embodiment, an affinity-matured antibody has nanomolar or even picomolar affinities for the target antigen. Affinity-matured antibodies are produced by procedures known in the art. For example, Marks et al., *Bio/Technology* 10:779-783 (1992) describes affinity maturation by VH- and VL-domain shuffling. Random mutagenesis of HVR and/or framework residues is described by, for example: Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

As use herein, the term "specifically binds to" or is "specific for" refers to measurable and reproducible interactions such as binding between a target and an antibody, that is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant (Kd) of ≤1 μM, ≤100 nM, ≤10 nM, ≤1 nM, or ≤0.1 nM. In certain embodiments, an antibody specifically binds to an epitope on a protein that is conserved among the protein from different species. In another embodiment, specific binding can include, but does not require exclusive binding.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the invention include human IgG1, IgG2, IgG3 and IgG4.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity that reflects a 1:1 interaction between members of a binding pair (e.g., antibody and antigen). The affinity of a molecule X for its partner Y can generally be represented by the dissociation constant ("Kd," see below). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative and exemplary embodiments for measuring binding affinity are described in the following.

In one embodiment, the "Kd" or "Kd value" according to this invention is measured by a radiolabeled antigen-binding assay (RIA) performed with the Fab version of an antibody of interest and its antigen as described by the following assay. Solution-binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)). To establish conditions for the assay, microtiter plates (DYNEX Technologies, Inc., Chantilly, Va.) are coated overnight with 5 μg/ml of a capturing anti-Fab antibody (Cappel Labs, Cochranville, Pa.) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620, Nalge Nunc International, Rochester, N.Y.), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% TWEEN-20™ surfactant in PBS. When the plates have dried, 150 μl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another embodiment, the Kd is measured by using surface-plasmon resonance assays using a BIA-CORE®-2000 or a BIACORE®-3000 instrument (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% TWEEN 20™ surfactant (PBST) at 25° C. at a flow rate of approximately 25 µl/min. Association rates ($k_{on}$) and dissociation rates ($k_{off}$) are calculated using a simple one-to-one Langmuir binding model (BIAcore® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface-plasmon resonance assay above, then the on-rate can be determined by using a fluorescent quenching technique that measures the increase or decrease in fluorescence-emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow-equipped spectrophotometer (Aviv Instruments) or a 8000-series SLM-AMINCO™ spectrophotometer (ThermoSpectronic, Madison, Wis.) with a stirred cuvette.

An "on-rate," "rate of association," "association rate," or "$k_{on}$," according to this invention can also be determined as described above using a BIACORE®-2000 or a BIACORE®-3000 system (BIAcore, Inc., Piscataway, N.J.).

An "isolated" nucleic acid molecule encoding the antibodies herein is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR2 ("amidate"), P(O)R, P(O)OR', CO, or CH2 ("formacetal"), in which each R or R' is independently H or substituted or unsubstituted alkyl (1-20C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single-stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

A "package insert" refers to instructions customarily included in commercial packages of medicaments that contain information about the indications customarily included in commercial packages of medicaments that contain information about the indications, usage, dosage, administration, contraindications, other medicaments to be combined with the packaged product, and/or warnings concerning the use of such medicaments, etc.

A "pharmaceutically acceptable acid" includes inorganic and organic acids which are non toxic at the concentration and manner in which they are formulated. For example, suitable inorganic acids include hydrochloric, perchloric, hydrobromic, hydroiodic, nitric, sulfuric, sulfonic, sulfinic, sulfanilic, phosphoric, carbonic, etc. Suitable organic acids include straight and branched-chain alkyl, aromatic, cyclic, cycloaliphatic, arylaliphatic, heterocyclic, saturated, unsaturated, mono, di- and tri-carboxylic, including for example, formic, acetic, 2-hydroxyacetic, trifluoroacetic, phenylacetic, trimethylacetic, t-butyl acetic, anthranilic, propanoic, 2-hydroxypropanoic, 2-oxopropanoic, propandioic, cyclopentanepropionic, cyclopentane propionic, 3-phenylpropionic, butanoic, butandioic, benzoic, 3-(4-hydroxybenzoyl)benzoic, 2-acetoxy-benzoic, ascorbic, cinnamic, lauryl sulfuric, stearic, muconic, mandelic, succinic, embonic, fumaric, malic, maleic, hydroxymaleic, malonic, lactic, citric, tartaric, glycolic, glyconic, gluconic, pyruvic, glyoxalic, oxalic, mesylic, succinic, salicylic, phthalic, palmoic, palmeic, thiocyanic, methanesulphonic, ethanesulphonic, 1,2-ethanedisulfonic, 2-hydroxyethanesulfonic, benzenesulphonic, 4-chorobenzenesulfonic, napthalene-2-sulphonic, p-toluenesulphonic, camphorsulphonic, 4-methylbicyclo [2.2.2]-oct-2-ene-1-carboxylic, glucoheptonic, 4,4'-methylenebis-3-(hydroxy-2-ene-1-carboxylic acid), hydroxynapthoic.

"Pharmaceutically-acceptable bases" include inorganic and organic bases which are non-toxic at the concentration and manner in which they are formulated. For example, suitable bases include those formed from inorganic base forming metals such as lithium, sodium, potassium, magnesium, calcium, ammonium, iron, zinc, copper, manganese, aluminum, N-methylglucamine, morpholine, piperidine and organic nontoxic bases including, primary, secondary and tertiary amines, substituted amines, cyclic amines and basic ion exchange resins, [e.g., $N(R')_4^+$ (where R' is independently H or $C_{1-4}$ alkyl, e.g., ammonium, Tris)], for example, isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, trimethamine, dicyclohexylamine, choline, and caffeine.

Additional pharmaceutically acceptable acids and bases useable with the present invention include those which are derived from the amino acids, for example, histidine, glycine, phenylalanine, aspartic acid, glutamic acid, lysine and asparagine.

"Pharmaceutically acceptable" buffers and salts include those derived from both acid and base addition salts of the above indicated acids and bases. Specific buffers and/or salts include histidine, succinate and acetate.

A "pharmaceutically acceptable sugar" is a molecule which, when combined with a protein of interest, significantly prevents or reduces chemical and/or physical instability of the protein upon storage. When the formulation is intended to be lyophilized and then reconstituted, "pharmaceutically acceptable sugars" may also be known as a "lyoprotectant". Exemplary sugars and their corresponding sugar alcohols include: an amino acid such as monosodium glutamate or histidine; a methylamine such as betaine; a lyotropic salt such as magnesium sulfate; a polyol such as trihydric or higher molecular weight sugar alcohols, e.g. glycerin, dextran, erythritol, glycerol, arabitol, xylitol, sorbitol, and mannitol; propylene glycol; polyethylene glycol; PLURONICS®; and combinations thereof. Additional exemplary lyoprotectants include glycerin and gelatin, and the sugars mellibiose, melezitose, raffinose, mannotriose and stachyose. Examples of reducing sugars include glucose, maltose, lactose, maltulose, iso-maltulose and lactulose. Examples of non-reducing sugars include non-reducing glycosides of polyhydroxy compounds selected from sugar alcohols and other straight chain polyalcohols. Preferred sugar alcohols are monoglycosides, especially those compounds obtained by reduction of disaccharides such as lactose, maltose, lactulose and maltulose. The glycosidic side group can be either glucosidic or galactosidic. Additional examples of sugar alcohols are glucitol, maltitol, lactitol and iso-maltulose. The preferred pharmaceutically-acceptable sugars are the non-reducing sugars trehalose or sucrose. Pharmaceutically acceptable sugars are added to the formulation in a "protecting amount" (e.g. pre-lyophilization) which means that the protein essentially retains its physical and chemical stability and integrity during storage (e.g., after reconstitution and storage).

The "diluent" of interest herein is one which is pharmaceutically acceptable (safe and non-toxic for administration to a human) and is useful for the preparation of a liquid formulation, such as a formulation reconstituted after lyophilization. Exemplary diluents include sterile water, bacteriostatic water for injection (BWFI), a pH buffered solution (e.g. phosphate-buffered saline), sterile saline solution, Ringer's solution or dextrose solution. In an alternative embodiment, diluents can include aqueous solutions of salts and/or buffers.

A "preservative" is a compound which can be added to the formulations herein to reduce bacterial activity. The addition of a preservative may, for example, facilitate the production of a multi-use (multiple-dose) formulation. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. The most preferred preservative herein is benzyl alcohol.

The term "pharmaceutical formulation" refers to a preparation that is in such form as to permit the biological activity of the active ingredient to be effective, and that contains no additional components that are unacceptably toxic to a subject to which the formulation would be administered. Such formulations are sterile.

A "sterile" formulation is aseptic or free from all living microorganisms and their spores.

The term "about" as used herein refers to the usual error range for the respective value readily known to the skilled person in this technical field. Reference to "about" a value or parameter herein includes (and describes) embodiments that are directed to that value or parameter per se.

As used herein and in the appended claims, the singular forms "a," "an," and "the" include plural reference unless the context clearly indicates otherwise. For example, reference to an "antibody" is a reference to from one to many antibodies, such as molar amounts, and includes equivalents thereof known to those skilled in the art, and so forth.

It is understood that aspect and embodiments of the invention described herein include "comprising," "consisting," and "consisting essentially of" aspects and embodiments.

III. Compositions and Methods of the Invention

The invention provides methods for treating or preventing an autoimmune disease (such as inflammatory bowel disease) in an individual comprising administering to the individual an effective amount of an anti-CD83 agonist antibody described herein. In some embodiments, an effective amount of an anti-CD83 agonist antibody is administered to an individual for treating or preventing ulcerative colitis in the individual. In some embodiments, an effective amount of an anti-CD83 agonist antibody is administered to an individual for treating or preventing Crohn's disease in the individual. In some embodiments, an effective amount of an anti-CD83 agonist antibody is administered to an individual for treating or preventing indeterminate colitis in the individual.

With respect to all methods described herein, reference to an anti-CD83 agonist antibody also includes compositions comprising one or more of those agents. Such compositions may further comprise suitable excipients, such as pharmaceutically acceptable excipients (carriers) including buffers, acids, bases, sugars, diluents, preservatives, and the like, which are well known in the art and are described herein. The present methods can be used alone or in combination with other conventional methods of treatment.

A. Anti-CD83 Agonist Antibodies

The methods of the invention use an anti-CD83 agonist antibody, which term refers to an anti-CD83 antibody that binds to CD83 expressed on a cell surface and activates signal transductions mediated by CD83 after binding to the CD83 expressed on the cell surface (such as CD83 expressed on the cell surface of mature dendritic cells). The anti-CD83 agonist antibodies described herein may have one or more of the following characteristics: (a) inhibit activation of MAPK signaling in mature dendritic cells (such as causing a decrease in phosphorylation of p38 and CREB proteins in mature dendritic cells); (b) inhibit activation of mTOR signaling in mature dendritic cells (such as causing a decrease in phosphorylation of the mTOR protein in mature dendritic cells); (c) inhibit release of one or more pro-inflammatory cytokines (such as, MCP-1, IL-12p40) from mature dendritic cells; (d) induce release of one or more anti-inflammatory cytokines from mature dendritic cells (such as IL-1ra); (e) induce a decrease of cell surface expression of mature dendritic cell activation markers (such as CD83, HLA-DR); (f) upregulate expression of one or more wound healing genes (such as, vcan, spock2, and fbn2) in mature dendritic cells; and (g) treat and/or prevent an autoimmune disease (such as IBD). The activities of anti-CD83 agonist antibodies may be measured in vitro and/or in vivo.

Anti-CD83 antibodies may be generated using methods known in the art, and screened for one or more of the agonist activities described herein. See, e.g., methods described in Example 9.

In some embodiment, the anti-CD83 antibody specifically binds to the extracellular region of human CD83. In some embodiments, the human CD83 comprises the mature amino acid sequence from

```
                                           (SEQ ID NO: 1)
MSRGLQLLLLSCAYSLAPATPEVKVACSEDVDLPCTAPWDPQVPYTVSWVK

LLEGGEERMETPQEDHLRGQHYHQKGQNGSFDAPNERPYSLKIRNTTSCNS

GTYRCTLQDPDGQRNLSGKVILRVTGCPAQRKEETFKKYRAEIVLLLALVI

FYLTLIEFTCKFARLQSIFPDFSKAGMERAFLPVTSPNKHLGLVTPHKTEL

V.
```

In some embodiments, the anti-CD83 antibody specifically binds to a polypeptide comprising the amino acid sequence of

```
                                           (SEQ ID NO: 2)
TPEVKVACSEDVDLPCTAPWDPQVPYTVSWVKLLEGGEERMETPQEDHLR

GQHYHQKGQNGSFDAPNERPYSLKIRNTTSCNSGTYRCTLQDPDGQRNLS

GKVILRVTGCPAQRKEETFKK.
```

In some embodiments, the antibody is a monoclonal antibody. In some embodiments, the antibody is an isolated antibody. In some embodiments, the antibody is a chimeric antibody, a humanized antibody, or a human antibody. In some embodiments, the antibody is an antibody fragment, such as a Fab, Fab'-SH, Fv, scFv, or (Fab')$_2$.

In some embodiments, the anti-CD83 antibody comprises at least one, two, three, four, five, or six HVRs selected from (a) HVR-H1 comprising the amino acid sequence of SEQ ID NO:31; (b) HVR-H2 comprising the amino acid sequence of SEQ ID NO:32; (c) HVR-H3 comprising the amino acid sequence of SEQ ID NO:33; (d) HVR-L1 comprising the amino acid sequence of SEQ ID NO:37; (e) HVR-L2 comprising the amino acid sequence of SEQ ID NO:38; and (f) HVR-L3 comprising the amino acid sequence of SEQ ID NO:39.

In some embodiments, the anti-CD83 antibody comprises six HVRs comprising (a) HVR-H1 comprising the amino acid sequence of SEQ ID NO:31; (b) HVR-H2 comprising the amino acid sequence of SEQ ID NO:32; (c) HVR-H3 comprising the amino acid sequence of SEQ ID NO:33; (d) HVR-L1 comprising the amino acid sequence of SEQ ID NO:37; (e) HVR-L2 comprising the amino acid sequence of SEQ ID NO:38; and (f) HVR-L3 comprising the amino acid sequence of SEQ ID NO:39.

In some embodiments, the anti-CD83 antibody comprises at least one, at least two, or all three VH HVR sequences selected from (a) HVR-H1 comprising the amino acid sequence of SEQ ID NO:31; (b) HVR-H2 comprising the amino acid sequence of SEQ ID NO:32; and (c) HVR-H3 comprising the amino acid sequence of SEQ ID NO:33. In one embodiment, the antibody comprises HVR-H3 comprising the amino acid sequence of SEQ ID NO:33. In another embodiment, the antibody comprises HVR-H3 comprising the amino acid sequence of SEQ ID NO:33 and HVR-L3 comprising the amino acid sequence of SEQ ID NO:39. In a further embodiment, the antibody comprises HVR-H3 comprising the amino acid sequence of SEQ ID NO:33, HVR-L3 comprising the amino acid sequence of SEQ ID NO:39, and HVR-H2 comprising the amino acid sequence of SEQ ID NO:32. In a further embodiment, the antibody comprises (a) HVR-H1 comprising the amino acid sequence of SEQ ID NO:31; (b) HVR-H2 comprising the amino acid sequence of SEQ ID NO:32; and (c) HVR-H3 comprising the amino acid sequence of SEQ ID NO:33.

In some embodiments, the anti-CD83 antibody comprises at least one, at least two, or all three VL HVR sequences selected from (a) HVR-L1 comprising the amino acid sequence of SEQ ID NO:37; (b) HVR-L2 comprising the amino acid sequence of SEQ ID NO:38; and (c) HVR-L3 comprising the amino acid sequence of SEQ ID NO:39. In one embodiment, the antibody comprises (a) HVR-L1 comprising the amino acid sequence of SEQ ID NO:37; (b) HVR-L2 comprising the amino acid sequence of SEQ ID NO:38; and (c) HVR-L3 comprising the amino acid sequence of SEQ ID NO:39.

In some embodiments, the anti-CD83 antibody comprises (a) a VH domain comprising at least one, at least two, or all three VH HVR sequences selected from (i) HVR-H1 comprising the amino acid sequence of SEQ ID NO:31, (ii) HVR-H2 comprising the amino acid sequence of SEQ ID NO:32, and (iii) HVR-H3 comprising an amino acid sequence selected from SEQ ID NO:33; and (b) a VL domain comprising at least one, at least two, or all three VL HVR sequences selected from (i) HVR-L1 comprising the amino acid sequence of SEQ ID NO:37, (ii) HVR-L2 comprising the amino acid sequence of SEQ ID NO:38, and (c) HVR-L3 comprising the amino acid sequence of SEQ ID NO:39.

In some embodiments, the anti-CD83 antibody comprises (a) HVR-H1 comprising the amino acid sequence of SEQ ID NO:31; (b) HVR-H2 comprising the amino acid sequence of SEQ ID NO:32; (c) HVR-H3 comprising the amino acid sequence of SEQ ID NO:33; (d) HVR-L1 comprising the amino acid sequence of SEQ ID NO:37; (e) HVR-L2 comprising the amino acid sequence of SEQ ID NO:38; and (f) HVR-L3 comprising an amino acid sequence of SEQ ID NO:39.

In some embodiments, the anti-CD83 antibody is humanized. In one embodiment, an anti-CD83 antibody comprises HVRs as in any of the above embodiments, and further comprises an acceptor human framework, e.g., a human immunoglobulin framework or a human consensus framework.

In some embodiments, an anti-CD83 antibody is provided, wherein the antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:30. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-CD83 antibody comprising that sequence retains the ability to bind to CD83. In certain embodiments, a total of 1 to 10 amino acids have been substituted, inserted and/or deleted in SEQ ID NO:30. In certain embodiments, substitutions, insertions, or deletions occur in regions outside the HVRs (i.e., in the FRs). Optionally, the anti-CD83 antibody comprises the VH sequence in SEQ ID NO:30, including post-translational modifications of that sequence. In a particular embodiment, the VH comprises one, two or three HVRs selected from: (a) HVR-H1 comprising the amino acid sequence of SEQ ID NO:31, (b) HVR-H2 comprising the amino acid sequence of SEQ ID NO:32, and (c) HVR-H3 comprising the amino acid sequence of SEQ ID NO:33.

In some embodiments, an anti-CD83 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:36. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-CD83 antibody comprising that sequence retains the ability to bind to CD83. In certain embodiments, a total of 1 to 10 amino acids have been substituted, inserted and/or deleted in SEQ ID NO:36. In certain embodiments, the substitutions, insertions, or deletions occur in regions outside the HVRs (i.e., in the FRs). Optionally, the anti-CD83 antibody comprises the VL sequence in SEQ ID NO:36, including post-translational modifications of that sequence. In a particular embodiment, the VL comprises one, two or three HVRs selected from (a) HVR-L1 comprising the amino acid sequence of SEQ ID NO:37; (b) HVR-L2 comprising the amino acid sequence of SEQ ID NO:38; and (c) HVR-L3 comprising the amino acid sequence of SEQ ID NO:39.

In some embodiments, an anti-CD83 antibody is provided, wherein the antibody comprises a VH as in any of the embodiments provided above, and a VL as in any of the embodiments provided above. In one embodiment, the antibody comprises the VH and VL sequences in SEQ ID NO:30 and SEQ ID NO:36, respectively, including post-translational modifications of those sequences. In one embodiment, the antibody comprises the heavy chain amino acid sequence shown in SEQ ID NO:29 and the light chain amino acid sequence shown in SEQ ID NO:35, including post-translational modifications of those sequences.

In one embodiment, provided herein is an anti-CD83 antibody that binds to human CD83 competitively with any one of the antibodies described herein. In certain embodiments, competitive binding may be determined using an ELISA assay. For example, in certain embodiments, an antibody is provided that binds to human CD83 competitively with an anti-CD83 antibody comprising a VH sequence of SEQ ID NO:30 and a VL sequence of SEQ ID NO:36. In certain embodiments, an antibody is provided that binds to human CD83 competitively with an anti-CD83 antibody comprising the heavy chain amino acid sequence shown in SEQ ID NO:29 and the light chain amino acid sequence shown in SEQ ID NO:35.

The antibody may have nanomolar or even picomolar affinities for target antigen CD83. In certain embodiments, the Kd of the antibody is about 0.05 to about 100 nM. For example, Kd of the antibody is any of about 100 nM, about 50 nM, about 10 nM, about 1 nM, about 500 pM, about 100 pM, or about 50 pM to any of about 2 pM, about 5 pM, about 10 pM, about 15 pM, about 20 pM, or about 40 pM.

B. Recombinant Preparation of Anti-CD83 Agonist Antibodies

The invention also provides methods of producing anti-CD83 agonist antibodies using recombinant techniques. For example, polypeptides can be prepared using isolated nucleic acids encoding such antibodies or fragments thereof, vectors and host-cells comprising such nucleic acids. Although the methods described under Section B generally refer to production of antibodies, these methods may also be used to produce any polypeptides described herein.

For recombinant production of antibodies or fragments thereof, nucleic acids encoding the desired antibodies or antibody fragments are isolated and inserted into a replicable vector for further cloning (amplification of the DNA) or for expression. DNA encoding the polyclonal or monoclonal antibodies is readily isolated (e.g., with oligonucleotide probes that specifically bind to genes encoding the heavy and light chains of the antibody) and sequenced using conventional procedures. Many cloning and/or expression vectors are commercially available. Vector components generally include, but are not limited to, one or more of the following, a signal sequence, an origin of replication, one or more marker genes, a multiple cloning site containing recognition sequences for numerous restriction endonucleases, an enhancer element, a promoter, and a transcription termination sequence.

(1) Signal Sequence Component

The antibodies or fragments thereof may be produced recombinantly not only directly, but also as a fusion protein, where the antibody is fused to a heterologous polypeptide, preferably a signal sequence or other polypeptide having a specific cleavage site at the N-terminus of the mature protein or polypeptide. The heterologous signal sequence selected preferably is one that is recognized and processed (i.e., cleaved by a signal peptidase) by eukaryotic host-cells. For prokaryotic host-cells that do not recognize and process native mammalian signal sequences, the eukaryotic (i.e., mammalian) signal sequence is replaced by a prokaryotic signal sequence selected, for example, from the group consisting of leader sequences from alkaline phosphatase, penicillinase, 1pp, or heat-stable enterotoxin II genes. For yeast secretion the native signal sequence may be substituted by, e.g., the yeast invertase leader, factor leader (including *Saccharomyces* and *Kluyveromyces*-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex virus gD signal, are available.

The DNA for such precursor region is ligated in reading frame to the DNA encoding the antibodies or fragments thereof.

(2) Origin of Replication

Both expression and cloning vectors contain a nucleic acid sequence that enables the vector to replicate in one or more selected host-cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, vesicular stomatitis virus ("VSV") or bovine papilloma virus ("BPV") are useful for cloning vectors in mammalian cells. Generally, the origin of replication component is not needed for mammalian expression vectors (the SV40 origin may typically be used only because it contains the early promoter).

(3) Selection Gene Component

Expression and cloning vectors may also contain a selection gene, known as a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

One example of a selection scheme utilizes a drug to arrest growth of a host-cell. Those cells that are successfully transformed with a heterologous gene produce a protein conferring drug resistance and thus survive the selection regimen. Examples of such dominant selection strategies use the drugs neomycin, mycophenolic acid and hygromycin.

Another example of suitable selectable markers for mammalian cells are those that enable the identification of cells competent to take up the antibody- or antibody fragment-encoding nucleic acids, such as dihydrofolate reductase ("DHFR"), thymidine kinase, metallothionein-I and -II, preferably primate metallothionein genes, adenosine deaminase, ornithine decarboxylase, and the like.

For example, cells transformed with the DHFR selection gene are first identified by culturing all of the transformants in a culture medium that contains methotrexate (Mtx), a competitive antagonist of DHFR. An exemplary host-cell strain for use with wild-type DHFR is the Chinese hamster ovary ("CHO") cell line lacking DHFR activity (e.g., ATCC CRL-9096).

Another example of suitable selectable markers for mammalian cells are those that enable the identification of cells competent to take up the antibody- or antibody fragment-encoding nucleic acids, such as dihydrofolate reductase ("DHFR"), glutamine synthetase (GS), thymidine kinase, metallothionein-I and -II, preferably primate metallothionein genes, adenosine deaminase, ornithine decarboxylase, and the like.

Alternatively, cells transformed with the GS (glutamine synthetase) gene are identified by culturing the transformants in a culture medium containing L-methionine sulfoximine (Msx), an inhibitor of GS. Under these conditions, the GS gene is amplified along with any other co-transformed nucleic acid. The GS selection/amplification system may be used in combination with the DHFR selection/amplification system described above.

Alternatively, host-cells (particularly wild-type hosts that contain endogenous DHFR) transformed or co-transformed with DNA sequences encoding anti-CD83 agonist antibodies or fragments thereof, wild-type DHFR protein, and another selectable marker such as aminoglycoside 3'-phosphotransferase ("APH") can be selected by cell growth in medium containing a selection agent for the appropriate selectable marker, such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature*, 282:39 (1979)). The trp1 gene provides a selection marker for a mutant strain of yeast lacking the ability to grow medium containing tryptophan (e.g., ATCC No. 44076 or PEP4-1). Jones, *Genetics*, 85:12 (1977). The presence of the trp1 lesion in the yeast host-cell genome then provides an effective environment for detecting transformation by growth in the absence of tryptophan. Similarly, Leu2-deficient yeast strains (e.g., ATCC 20,622 or 38,626) can be complemented by known plasmids bearing the Leu2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis*. Van den Berg, *Bio/Technology*, 8:135 (1990). Stable multi-copy expression vectors for secretion of mature recombinant human serum albumin by industrial strains of *Kluyveromyces* have also been disclosed. Fleer et al., *Bio/Technology*, 9:968-975 (1991).

(4) Promoter Component

Expression and cloning vectors usually contain a promoter that is recognized by the host organism and is operably linked to the nucleic acid encoding the anti-CD83 agonist antibodies or fragments thereof. Promoters suitable for use with prokaryotic hosts include the phoA promoter, lactamase and lactose promoter systems, alkaline phosphatase promoter, a tryptophan promoter system, and hybrid promoters such as the tac promoter, although other known bacterial promoters are also suitable. Promoters for use in bacterial systems also will contain a Shine-Dalgarno (S.D.) sequence operably linked to the DNA encoding the antibodies and antibody fragments.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the polyA tail to the 3' end of the coding sequence. All of these sequences may be inserted into eukaryotic expression vectors.

Examples of suitable promoter sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phospho-fructokinase, glucose-6-phosphate isomerase, 3-phosphoglycerate mutase, pyruvate kinase, triosephosphate isomerase, phosphoglucose isomerase, and glucokinase.

Inducible promoters in yeast have the additional advantage of permitting transcription controlled by growth conditions. Exemplary inducible promoters include the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Transcription of nucleic acids encoding antibodies or fragments thereof from vectors in mammalian host-cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), by heterologous mammalian promoters, e.g., the actin promoter or an immunoglobulin promoter, and by heat-shock gene promoters, provided such promoters are compatible with the desired host-cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., *Nature* 297:598-601 (1982), regarding methods for expression of human interferon cDNA in mouse cells under the control of a thymidine kinase promoter from herpes simplex virus. Alternatively, the Rous Sarcoma Virus long terminal repeat can be used as the promoter.

(5) Enhancer Element Component

Transcription of a DNA encoding the antibodies or fragments thereof by higher eukaryotes is often increased by inserting an enhancer sequence into the vector. Many enhancer sequences are now known from mammalian genes (globin, elastase, albumin, α-fetoprotein, and insulin). Typically, however, one of ordinary skill in the art will use an enhancer from a eukaryotic virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature* 297:17-18 (1982) on enhancing elements for activation of eukaryotic promoters. The enhancer may be spliced into the vector at a position 5' or 3' to the antibody- or antibody-fragment encoding sequences, but is preferably located at a site 5' of the promoter.

(6) Transcription Termination Component

Expression vectors used in eukaryotic host-cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding antibodies or fragments thereof. One useful transcription termination component is the bovine growth hormone polyadenylation region. See WO94/11026 and the expression vector disclosed therein.

(7) Selection and Transformation of Host-Cells

Suitable host-cells for cloning or expressing the DNA encoding anti-CD83 agonist antibodies or fragments thereof in the vectors described herein include the prokaryotic, yeast, or higher eukaryotic cells described above. Suitable prokaryotes for this purpose include eubacteria, such as Gram-negative or Gram-positive organisms, for example, Enterobacteriaceae such as *Escherichia*, e.g., *E. coli*, *Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr., 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are also suitable. These examples are illustrative rather than limiting.

Full length antibodies, antibody fragments, and antibody fusion proteins can be produced in bacteria, in particular when glycosylation and Fc effector function are not needed, such as when the therapeutic antibody is conjugated to a cytotoxic agent (e.g., a toxin). Full length antibodies have greater half life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789,199 (Joly et al.), and U.S. Pat. No. 5,840,523 (Simmons et al.) which describes translation initiation region (TIR) and signal sequences for optimizing expression and secretion. After expression, antibodies or antibody fragments are isolated from the *E. coli* cell paste in a soluble fraction and can be purified through, e.g., a protein A or G column depending on the isotype. Final purification can be carried out by the same process used to purify antibodies or antibody fragments expressed, e.g., in CHO cells.

In addition to prokaryotes, eukaryotic microbes such as filamentous fungi or yeast are also suitable cloning or expression hosts for antibody- or antibody-fragment encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* spp., such as *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*. For a review discussing the use of yeasts and filamentous fungi for the production of therapeutic proteins, see, e.g., Gerngross, *Nat. Biotech.* 22: 1409-1414 (2004).

Certain fungi and yeast strains may be selected in which glycosylation pathways have been "humanized," resulting in the production of an antibody with a partially or fully human glycosylation pattern. See, e.g., Li et al., *Nat. Biotech.* 24:210-215 (2006) (describing humanization of the glycosylation pathway in *Pichia pastoris*); and Gerngross et al., supra.

Suitable host-cells for the expression of glycosylated antibodies or antibody fragments are derived from multicellular organisms. Examples of invertebrate cells include plant and insect-cells. Numerous baculoviral strains and variants and corresponding permissive insect host-cells from hosts such as *Spodoptera frugiperda* (caterpillar), *Aedes aegypti* (mosquito), *Aedes albopictus* (mosquito), *Drosophila melanogaster* (fruitfly), and *Bombyx mori* (moth) have been identified. A variety of viral strains for transfection are publicly available, e.g., the L-1 variant of *Autographa californica* NPV and the Bm-5 strain of *Bombyx mori* NPV. Such viruses may be used as the virus herein according to the present invention, particularly for transfection of *Spodoptera frugiperda* cells.

Plant-cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host-cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Nat'l Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2). Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J., 2003), pp. 255-268.

Host-cells are transformed with the above-described expression or cloning vectors for antibody or antibody fragment production and cultured in conventional nutrient media modified as appropriate for inducing promoters, selecting transformants, or amplifying the genes encoding the desired sequences.

(8) Culturing the Host-Cells

The host-cells used to produce the anti-CD83 agonist antibodies or antibody fragments described herein may be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host-cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WIPO Publication Nos. WO 90/03430; WO 87/00195; or U.S. Pat. Re. 30,985 may be used as culture media for the host-cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host-cell selected for expression, and will be apparent to the ordinarily skilled artisan.

(9) Purification of Antibody

When using recombinant techniques, the anti-CD83 agonist antibodies or antibody fragments can be produced intracellularly, in the periplasmic space, or secreted directly into the medium. If the antibodies are produced intracellularly, as a first step, the particulate debris from either host-cells or lysed fragments is removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 minutes. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody or antibody fragment compositions prepared from such cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies or antibody fragments that are based on human 1, 2, or 4 heavy chains (Lindmark et al., *J. Immunol. Meth.* 62:1-13 (1983)). Protein G is recommended for all mouse isotypes and for human 3 heavy chain antibodies or antibody fragments (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibodies or antibody fragments comprise a $C_H3$ domain, the Bakerbond ABX™resin (J. T. Baker, Phillipsburg, N.J.) is useful for purification. Other techniques for protein purification, such as fractionation on an ion-exchange column, ethanol precipitation, Reverse Phase HPLC, chromatography on silica, heparin, SEPHAROSE™, or anion or cation exchange resins (such as a polyaspartic acid column), as well as chromatofocusing, SDS-PAGE, and ammonium sulfate precipitation are also available depending on the antibody or antibody fragment to be recovered.

Following any preliminary purification step or steps, the mixture comprising the antibody or antibody fragment of interest and contaminants may be subjected to low pH hydrophobic interaction chromatography using an elution buffer at a pH between about 2.5-4.5, preferably performed at low salt concentrations (e.g., from about 0-0.25 M salt).

In general, various methodologies for preparing antibodies for use in research, testing, and clinical applications are well-established in the art, consistent with the above-described methodologies and/or as deemed appropriate by one skilled in the art for a particular antibody of interest.

C. Antibody Preparation

The antibodies useful in the present invention can encompass monoclonal antibodies, polyclonal antibodies, antibody fragments (e.g., Fab, Fab'-SH, Fv, scFv, and F(ab')$_2$), chimeric antibodies, bispecific antibodies, multivalent antibodies, heteroconjugate antibodies, fusion proteins comprising an antibody portion, humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or of any other origin (including chimeric or humanized antibodies).

(1) Polyclonal Antibodies

Polyclonal antibodies are generally raised in animals by multiple subcutaneous (sc) or intraperitoneal (ip) injections of the relevant antigen and an adjuvant. It may be useful to conjugate the relevant antigen (e.g., purified or recombinant CD83) to a protein that is immunogenic in the species to be immunized, e.g., keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are independently lower alkyl groups. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The animals are immunized against the desired antigen, immunogenic conjugates, or derivatives by combining, e.g., 100 μg (for rabbits) or 5 μg (for mice) of the protein or conjugate with 3 volumes of Freund's complete adjuvant and injecting the solution intradermally at multiple sites. One month later, the animals are boosted with 1/5 to 1/10 the original amount of peptide or conjugate in Freund's complete adjuvant by subcutaneous injection at multiple sites. Seven to fourteen days later, the animals are bled and the serum is assayed for antibody titer. Animals are boosted until the titer plateaus. Conjugates also can be made in recombinant-cell culture as protein fusions. Also, aggregating agents such as alum are suitable to enhance the immune response.

(2) Monoclonal Antibodies

Monoclonal antibodies are obtained from a population of substantially homogeneous antibodies, i.e., the individual antibodies comprising the population are identical except for possible naturally occurring mutations and/or post-translational modifications (e.g., isomerizations, amidations) that may be present in minor amounts. Thus, the modifier "monoclonal" indicates the character of the antibody as not being a mixture of discrete antibodies.

For example, the monoclonal antibodies may be made using the hybridoma method first described by Kohler et al., *Nature,* 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization (e.g., purified or recombinant CD83). Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice,* pp. 59-103 (Academic Press, 1986)).

The immunizing agent will typically include the antigenic protein (e.g., purified or recombinant CD83) or a fusion variant thereof. Generally peripheral blood lymphocytes ("PBLs") are used if cells of human origin are desired, while spleen or lymph node cells are used if non-human mammalian sources are desired. The lymphoctyes are then fused with an immortalized cell line using a suitable fusing agent, such as polyethylene glycol, to form a hybridoma cell. Goding, *Monoclonal Antibodies: Principles and Practice,* Academic Press (1986), pp. 59-103.

Immortalized cell lines are usually transformed mammalian cells, particularly myeloma cells of rodent, bovine or human origin. Usually, rat or mouse myeloma cell lines are employed. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which are substances that prevent the growth of HGPRT-deficient-cells.

Preferred immortalized myeloma cells are those that fuse efficiently, support stable high-level production of antibody by the selected antibody-producing cells, and are sensitive to a medium such as HAT medium. Among these, preferred are murine myeloma lines, such as those derived from MOPC-21 and MPC-11 mouse tumors (available from the Salk Institute Cell Distribution Center, San Diego, Calif. USA), as well as SP-2 cells and derivatives thereof (e.g., X63-Ag8-653) (available from the American Type Culture Collection, Manassas, Va. USA). Human myeloma and mouse-human heteromyeloma cell lines have also been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen (e.g., CD83). Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The culture medium in which the hybridoma cells are cultured can be assayed for the presence of monoclonal antibodies directed against the desired antigen (e.g., CD83). Preferably, the binding affinity and specificity of the monoclonal antibody can be determined by immunoprecipitation or by an in vitro binding assay, such as radioimmunoassay (RIA) or enzyme-linked assay (ELISA). Such techniques and assays are known in the in art. For example, binding affinity may be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as tumors in a mammal.

The monoclonal antibodies secreted by the subclones are suitably separated from the culture medium, ascites fluid, or serum by conventional immunoglobulin purification procedures such as, for example, protein A-Sepharose chromatography, hydroxylapatite chromatography, gel electrophoresis, dialysis, affinity chromatography, and other methods as described above.

Monoclonal antibodies may also be made by recombinant DNA methods, such as those disclosed in U.S. Pat. No. 4,816,567, and as described above. DNA encoding the monoclonal antibodies is readily isolated and sequenced using conventional procedures (e.g., by using oligonucleotide probes that specifically bind to genes encoding the heavy and light chains of murine antibodies). The hybridoma cells serve as a preferred source of such DNA. Once isolated, the DNA may be placed into expression vectors, which are then transfected into host-cells such as *E. coli* cells, simian COS cells, Chinese hamster ovary (CHO) cells, or myeloma cells that do not otherwise produce immunoglobulin protein, in order to synthesize monoclonal antibodies in such recombinant host-cells. Review articles on recombinant expression in bacteria of DNA encoding the antibody include Skerra et al., *Curr. Opin. Immunol.*, 5:256-262 (1993) and Plückthun, *Immunol. Rev.* 130:151-188 (1992).

In certain embodiments, antibodies can be isolated from antibody phage libraries generated using the techniques described in McCafferty et al., *Nature*, 348:552-554 (1990). Clackson et al., *Nature*, 352:624-628 (1991) and Marks et al., *J. Mol. Biol.*, 222:581-597 (1991) described the isolation of murine and human antibodies, respectively, from phage libraries. Subsequent publications describe the production of high affinity (nanomolar ("nM") range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nucl. Acids Res.*, 21:2265-2266 (1993)). Thus, these techniques are viable alternatives to traditional monoclonal antibody hybridoma techniques for isolation of monoclonal antibodies of desired specificity (e.g., those that bind CD83).

The DNA encoding antibodies or fragments thereof may also be modified, for example, by substituting the coding sequence for human heavy- and light-chain constant domains in place of the homologous murine sequences (U.S. Pat. No. 4,816,567; Morrison, et al., *Proc. Natl Acad. Sci. USA*, 81:6851 (1984)), or by covalently joining to the immunoglobulin coding sequence all or part of the coding sequence for a non-immunoglobulin polypeptide. Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

The monoclonal antibodies described herein (e.g., anti-CD83 agonist antibodies or fragments thereof) may by monovalent, the preparation of which is well known in the art. For example, one method involves recombinant expression of immunoglobulin light chain and a modified heavy chain. The heavy chain is truncated generally at any point in the Fc region so as to prevent heavy chain crosslinking. Alternatively, the relevant cysteine residues may be substituted with another amino acid residue or are deleted so as to prevent crosslinking. In vitro methods are also suitable for preparing monovalent antibodies. Digestion of antibodies to produce fragments thereof, particularly Fab fragments, can be accomplished using routine techniques known in the art.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

(3) Humanized Antibodies.

The antibodies (such as anti-CD83 agonist antibodies) or antibody fragments of the invention may further comprise humanized or human antibodies. Humanized forms of non-human (e.g., murine) antibodies are chimeric immunoglobulins, immunoglobulin chains or fragments thereof (such as Fab, Fab'-SH, Fv, scFv, F(ab')$_2$ or other antigen-binding subsequences of antibodies) which contain minimal sequence derived from non-human immunoglobulin. Humanized antibodies include human immunoglobulins (recipient antibody) in which residues from a complementarity determining region (CDR) of the recipient are replaced by residues from a CDR of a non-human species (donor antibody) such as mouse, rat, hamster, or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally will also comprise at least a portion of an immunoglobulin constant region (Fc), typically that of a human immunoglobulin. Jones et al., *Nature* 321: 522-525 (1986); Riechmann et al., *Nature* 332: 323-329 (1988) and Presta, *Curr. Opin. Struct. Biol.* 2: 593-596 (1992).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers, Jones et al., *Nature* 321:522-525 (1986); Riechmann et al., *Nature* 332:323-327 (1988); Verhoeyen et al., *Science* 239:1534-1536 (1988), or through substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody. Sims et al., *J. Immunol.*, 151:2296 (1993); Chothia et al., *J. Mol. Biol.,* 196:901 (1987). Another method uses a particular framework derived from the consensus sequence of all human antibodies of a particular subgroup of light or heavy chains. The same framework may be used for several different humanized antibodies. Carter et al., *Proc. Nat'l Acad. Sci. USA* 89:4285 (1992); Presta et al., *J. Immunol.* 151:2623 (1993).

Furthermore, it is important that antibodies be humanized with retention of high affinity for the antigen and other favorable biological properties. To achieve this goal, according to a preferred method, humanized antibodies are prepared by a process of analyzing the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen or antigens (e.g., CD83), is achieved. In general, the CDR residues are directly and most substantially involved in influencing antigen binding.

Various forms of the humanized antibody are contemplated. For example, the humanized antibody may be an antibody fragment, such as an Fab, which is optionally conjugated with one or more cytotoxic agent(s) in order to generate an immunoconjugate. Alternatively, the humanized antibody may be an intact antibody, such as an intact IgG1 antibody.

(4) Human Antibodies

Alternatively, human antibodies can be generated. For example, it is now possible to produce transgenic animals (e.g., mice) that are capable, upon immunization, of producing a full repertoire of human antibodies in the absence of endogenous immunoglobulin production. The homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Nat'l Acad. Sci. USA,* 90:2551 (1993); Jakobovits et al., *Nature,* 362:255-258 (1993); Bruggermann et al., *Year in Immunol.,* 7:33 (1993); U.S. Pat. No. 5,591,669 and WO 97/17852.

Alternatively, phage display technology can be used to produce human antibodies and antibody fragments in vitro, from immunoglobulin variable (V) domain gene repertoires from unimmunized donors. McCafferty et al., *Nature* 348: 552-553 (1990); Hoogenboom and Winter, *J. Mol. Biol.* 227: 381 (1991). According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., *Curr. Opin Struct. Biol.* 3:564-571 (1993). Several sources of V-gene segments can be used for phage display. Clackson et al., Nature 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See also U.S. Pat. Nos. 5,565,332 and 5,573,905.

The techniques of Cole et al., and Boerner et al., are also available for the preparation of human monoclonal antibodies (Cole et al., Monoclonal Antibodies and Cancer Therapy, Alan R. Liss, p. 77 (1985) and Boerner et al., *J. Immunol.* 147(1): 86-95 (1991). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly and antibody repertoire. This approach is described, for example, in U.S. Pat. Nos. 5,545,807; 5,545,806, 5,569,825, 5,625,126, 5,633,425, 5,661,016 and in the following scientific publications: Marks et al., *Bio/Technology* 10: 779-783 (1992); Lonberg et al., *Nature* 368: 856-859 (1994); Morrison, *Nature* 368: 812-13 (1994), Fishwild et al., *Nature Biotechnology* 14: 845-51 (1996), Neuberger, *Nature Biotechnology* 14: 826 (1996) and Lonberg and Huszar, *Intern. Rev. Immunol.* 13: 65-93 (1995).

Finally, human antibodies may also be generated in vitro by activated B-cells (see U.S. Pat. Nos. 5,567,610 and 5,229,275).

(5) Antibody Fragments

In certain circumstances there are advantages to using antibody fragments, rather than whole antibodies. Smaller fragment sizes allow for rapid clearance, and may lead to improved access to solid tumors.

Various techniques have been developed for the production of antibody fragments. Traditionally, these fragments were derived via proteolytic digestion of intact antibodies (see, e.g., Morimoto et al., *J. Biochem. Biophys. Method.* 24:107-117 (1992); and Brennan et al., *Science* 229:81 (1985)). However, these fragments can now be produced directly by recombinant host-cells, for example, using nucleic acids encoding antibodies to CD83 as discussed above. Fab, Fv and scFv antibody fragments can all be expressed in and secreted from *E. coli*, thus allowing the straightforward production of large amounts of these fragments. Antibody fragments can also be isolated from the antibody phage libraries as discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host-cell culture. Production of Fab and F(ab')$_2$ antibody fragments with increased in vivo half-lives are described in U.S. Pat. No. 5,869,046. In other embodiments, the antibody of choice is a single chain Fv fragment (scFv). See WO 93/16185; U.S. Pat. No. 5,571,894 and U.S. Pat. No. 5,587,458. The antibody fragment may also be a "linear antibody," e.g., as described in U.S. Pat. No. 5,641,870. Such linear antibody fragments may be monospecific or bispecific.

(6) Bispecific and Polyspecific Antibodies

Bispecific antibodies (BsAbs) are antibodies that have binding specificities for at least two different epitopes, including those on the same or another protein (e.g., CD83). Such antibodies can be derived from full length antibodies or antibody fragments (e.g., F(ab')$_2$ bispecific antibodies).

Methods for making bispecific antibodies are known in the art. Traditional production of full length bispecific antibodies is based on the coexpression of two immunoglobulin heavy-chain/light chain pairs, where the two chains have different specificities. Millstein et al., *Nature,* 305:537-539 (1983). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829 and in Traunecker et al., *EMBO J.,* 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, $C_H2$, and $C_H3$ regions. It is preferred to have the first heavy-chain constant region ($C_H1$) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only half of the bispecific molecules provides for an easy way of separation. This approach is disclosed in WO 94/04690. For further details of generating bispecific antibodies, see, for example, Suresh et al., *Methods in Enzymology* 121: 210 (1986).

According to another approach described in WO 96/27011 or U.S. Pat. No. 5,731,168, the interface between a pair of antibody molecules can be engineered to maximize the percentage of heterodimers which are recovered from recombinant-cell culture. The preferred interface comprises at least a part of the $C_H3$ region of an antibody constant domain. In this method, one or more small amino acid side chains from the interface of the first antibody molecule are replaced with larger side chains (e.g., tyrosine or tryptophan). Compensatory "cavities" of identical or similar size to the large side chains(s) are created on the interface of the second antibody molecule by replacing large amino acid side chains with smaller ones (e.g., alanine or threonine). This provides a mechanism for increasing the yield of the heterodimer over other unwanted end-products such as homodimers.

Techniques for generating bispecific antibodies from antibody fragments have been described in the literature. For example, bispecific antibodies can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., *J. Exp. Med.* 175: 217-225 (1992) describes the production of fully humanized bispecific antibody F(ab')$_2$ molecules. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T-cells, as well as trigger the lytic activity of human cytotoxic lymphocytes against human breast tumor targets.

Various techniques for making and isolating bivalent antibody fragments directly from recombinant-cell culture have also been described. For example, bivalent heterodimers have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. The "diabody" technology described by Hollinger et al., *Proc. Nat'l Acad. Sci. USA*, 90: 6444-6448 (1993) has provided an alternative mechanism for making bispecific/bivalent antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific/bivalent antibody fragments by the use of single-chain Fv (sFv) dimers has also been reported. See Gruber et al., *J. Immunol.*, 152:5368 (1994).

Antibodies with more than two valencies are also contemplated. For example, trispecific antibodies can be prepared. Tutt et al., *J. Immunol.* 147:60 (1991). Exemplary bispecific antibodies may bind to two different epitopes on a given molecule (e.g., CD83).

(7) Multivalent Antibodies

A multivalent antibody may be internalized (and/or catabolized) faster than a bivalent antibody by a cell expressing an antigen to which the antibodies bind. The anti-CD83 antibodies or antibody fragments of the present invention can be multivalent antibodies (which are other than of the IgM class) with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises an Fc region or a hinge region. In this scenario, the antibody will comprise an Fc region and three or more antigen binding sites amino-terminal to the Fc region. The preferred multivalent antibody herein comprises three to about eight, but preferably four, antigen binding sites. The multivalent antibody comprises at least one polypeptide chain (and preferably two polypeptide chains), wherein the polypeptide chain or chains comprise two or more variable domains. For instance, the polypeptide chain or chains may comprise VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or polypeptide, and n is 0 or 1. Similarly, the polypeptide chain or chains may comprise $V_H$-$C_H$1-flexible linker-$V_H$-$C_H$1-Fc region chain; or $V_H$-$C_H$1-$V_H$-$C_H$1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

(8) Heteroconjugate Antibodies

Heteroconjugate antibodies are also within the scope of the present invention. Heteroconjugate antibodies are composed of two covalently joined antibodies. For example, one of the antibodies in the heteroconjugate can be coupled to avidin, the other to biotin. Such antibodies have, for example, been proposed to target immune system cells to unwanted cells, U.S. Pat. No. 4,676,980, and have been used to treat HIV infection. International Publication Nos. WO 91/00360, WO 92/200373 and EP 0308936. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980. Heteroconjugate antibodies may be made using any convenient cross-linking methods. Suitable cross-linking agents are well known in the art, and are disclosed in U.S. Pat. No. 4,676,980, along with a number of cross-linking techniques.

(9) Effector Function Engineering

It may be desirable to modify the antibody of the invention to modify effector function and/or to increase serum half life of the antibody. For example, the Fc receptor binding site on the constant region may be modified or mutated to remove or reduce binding affinity to certain Fc receptors, such as FcγRI, FcγRII, and/or FcγRIII. In some embodiments, the effector function is impaired by removing N-glycosylation of the Fc region (e.g., in the CH 2 domain of IgG) of the antibody. In some embodiments, the effector function is impaired by modifying regions such as 233-236, 297, and/or 327-331 of human IgG as described in PCT WO 99/58572 and Armour et al., *Molecular Immunology* 40: 585-593 (2003); Reddy et al., *J. Immunology* 164:1925-1933 (2000).

To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG$_1$, IgG$_2$, IgG$_3$, or IgG$_4$) that is responsible for increasing the in vivo serum half-life of the IgG molecule.

(10) Other Amino Acid Sequence Modifications

Amino acid sequence modifications of the antibodies described herein are contemplated. For example, it may be desirable to improve the binding affinity and/or other biological properties of the antibodies or antibody fragments. Amino acid sequence variants of the antibodies or antibody fragments are prepared by introducing appropriate nucleotide changes into the nucleic acid encoding the antibodies or antibody fragments, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics (i.e., the ability to bind or physically interact with CD83). The amino acid changes also may alter post-translational processes of the antibody, such as changing the number or position of glycosylation sites.

A useful method for identification of certain residues or regions of the antibody that are preferred locations for mutagenesis is called "alanine scanning mutagenesis" as described by Cunningham and Wells in *Science*, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with the target antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Amino acid sequence insertions include amino- ("N") and/or carboxy- ("C") terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in the Table A below under the heading of "preferred substitutions". If such substitutions result in a change in biological activity, then more substantial changes, denominated "exemplary substitutions" in Table A, or as further described below in reference to amino acid classes, may be introduced and the products screened.

TABLE A

Amino Acid Substitutions

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; asp; lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | Ala | ala |
| Ser (S) | Thr | thr |
| Thr (T) | Ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment, such as an Fv fragment).

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and the antigen CD83. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-IgE antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibodies or antibody fragments.

(10) Other Antibody Modifications

The antibodies or antibody fragments of the present invention can be further modified to contain additional nonproteinaceous moieties that are known in the art and readily available. Preferably, the moieties suitable for derivatization of the antibody are water-soluble polymers. Non-limiting examples of water-soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, polypropylene glycol homopolymers, polypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc. Such techniques and other suitable formulations are disclosed in *Remington: The Science and Practice of Pharmacy,* 20th Ed., Alfonso Gennaro, Ed., Philadelphia College of Pharmacy and Science (2000).

D. Pharmaceutical Compositions and Formulations

Therapeutic compositions and formulations of anti-CD83 agonist antibodies described here can be prepared by mixing the active ingredient having the desired degree of purity with optional pharmaceutically acceptable carriers, excipients or stabilizers (*Remington: The Science and Practice of Pharmacy,* 20th Ed., (Gennaro, A. R., ed., Lippincott Williams & Wilkins, Publishers, Philadelphia, Pa. 2000). Acceptable carriers, excipients, or stabilizers are nontoxic to recipients at the dosages and concentrations employed, and include buffers, antioxidants including ascorbic acid, methionine, Vitamin E, sodium metabisulfite; preservatives, isotonicifiers, stabilizers, metal complexes (e.g., Zn-protein complexes), chelating agents such as EDTA and/or non-ionic surfactants, and the like.

Buffers are used to control the pH in a range which optimizes the therapeutic effectiveness, especially if stability is pH dependent. Buffers are preferably present at concentrations ranging from about 50 mM to about 250 mM. Suitable buffering agents for use with the present invention include both organic and inorganic acids and salts thereof, such as citrate, phosphate, succinate, tartrate, fumarate, gluconate, oxalate, lactate, acetate. Additionally, buffers may comprise histidine and trimethylamine salts such as Tris.

Preservatives are added to retard microbial growth, and are typically present in a range from 0.2%-1.0% (w/v). Suitable preservatives for use with the present invention include octadecyldimethylbenzyl ammonium chloride; hexamethonium chloride; benzalkonium halides (e.g., chloride, bromide, iodide), benzethonium chloride; thimerosal, phenol, butyl or benzyl alcohol; alkyl parabens such as methyl or propyl paraben; catechol; resorcinol; cyclohexanol, 3-pentanol, and m-cresol.

Tonicity agents, sometimes known as "stabilizers" are present to adjust or maintain the tonicity of liquid in a composition. When used with large, charged biomolecules such as proteins and antibodies, they are often termed "stabilizers" because they can interact with the charged groups of the amino acid side chains, thereby lessening the potential for inter- and intra-molecular interactions. Tonicity agents can be present in any amount between 0.1% to 25% by weight, or more preferably between 1% to 5% by weight, taking into account the relative amounts of the other ingredients. Preferred tonicity agents include polyhydric sugar alcohols, preferably trihydric or higher sugar alcohols, such as glycerin, erythritol, arabitol, xylitol, sorbitol and mannitol.

Additional excipients include agents which can serve as one or more of the following: (1) bulking agents, (2) solubility enhancers, (3) stabilizers and (4) and agents preventing denaturation or adherence to the container wall. Such excipients include: polyhydric sugar alcohols (listed above); amino acids such as alanine, glycine, glutamine, asparagine, histidine, arginine, lysine, ornithine, leucine, 2-phenylalanine, glutamic acid, threonine, and the like; organic sugars or sugar alcohols such as sucrose, lactose, lactitol, trehalose, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, α-monothioglycerol and sodium thio sulfate; low molecular weight proteins such as human serum albumin, bovine serum albumin, gelatin or other immunoglobulins; hydrophilic polymers such as polyvinylpyrrolidone; monosaccharides (e.g., xylose, mannose, fructose, glucose; disaccharides (e.g., lactose, maltose, sucrose); trisaccharides such as raffinose; and polysaccharides such as dextrin or dextran.

Non-ionic surfactants or detergents (also known as "wetting agents") are present to help solubilize the therapeutic agent as well as to protect the therapeutic protein against agitation-induced aggregation, which also permits the formulation to be exposed to shear surface stress without causing denaturation of the active therapeutic protein or antibody. Non-ionic surfactants are present in a range of about 0.05 mg/ml to about 1.0 mg/ml, preferably about 0.07 mg/ml to about 0.2 mg/ml.

Suitable non-ionic surfactants include polysorbates (20, 40, 60, 65, 80, etc.), polyoxamers (184, 188, etc.), PLURONIC® polyols, TRITON®, polyoxyethylene sorbitan monoethers (TWEEN®-20, TWEEN®-80, etc.), lauromacrogol 400, polyoxyl 40 stearate, polyoxyethylene hydrogenated castor oil 10, 50 and 60, glycerol monostearate, sucrose fatty acid ester, methyl cellulose and carboxymethyl cellulose. Anionic detergents that can be used include sodium lauryl sulfate, dioctyle sodium sulfosuccinate and dioctyl sodium sulfonate. Cationic detergents include benzalkonium chloride or benzethonium chloride.

In order for pharmaceutical formulations comprising the anti-CD83 agonist antibodies to be used for in vivo administration, they must be sterile. The formulation may be rendered sterile by filtration through sterile filtration membranes. The therapeutic compositions herein generally are placed into a container having a sterile access port, for example, an intravenous solution bag or vial having a stopper pierceable by a hypodermic injection needle.

The route of administration is in accordance with known and accepted methods, such as by single or multiple bolus or infusion over a long period of time in a suitable manner, e.g., injection or infusion by subcutaneous, intravenous, intraperitoneal, intramuscular, intraarterial, intralesional or intraarticular routes, topical administration, inhalation or by sustained release or extended-release means.

The anti-CD83 agonist antibody compositions and formulations herein may also contain more than one active compound as necessary for the particular indication being treated, preferably those with complementary activities that do not adversely affect each other. Alternatively, or in addition, the composition may comprise a cytotoxic agent, cytokine or growth inhibitory agent. Such molecules are suitably present in combination in amounts that are effective for the purpose intended.

The active ingredients may also be entrapped in microcapsules prepared, for example, by coascervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 20th Edition, supra.

Stability of the proteins and antibodies described herein may be enhanced through the use of non-toxic "water-soluble polyvalent metal salts". Examples include $Ca^{2+}$, $Mg^{2+}$, $Zn^{2+}$, $Fe^{2+}$, $Fe^{3+}$, $Cu^{2+}$, $Sn^{2+}$, $Sn^{4+}$, $Al^{2+}$ and $Al^{3+}$. Exemplary anions that can form water soluble salts with the above polyvalent metal cations include those formed from inorganic acids and/or organic acids. Such water-soluble salts have are soluble in water (at 20° C.) to at least about 20 mg/ml, alternatively at least about 100 mg/ml, alternatively at least about 200 mg/ml.

Suitable inorganic acids that can be used to form the "water soluble polyvalent metal salts" include hydrochloric, acetic, sulfuric, nitric, thiocyanic and phosphoric acid. Suitable organic acids that can be used include aliphatic carboxylic acid and aromatic acids. Aliphatic acids within this definition may be defined as saturated or unsaturated $C_{2-9}$ carboxylic acids (e.g., aliphatic mono-, di- and tri-carboxylic acids). For example, exemplary monocarboxylic acids within this definition include the saturated $C_{2-9}$ monocarboxylic acids acetic, proprionic, butyric, valeric, caproic, enanthic, caprylic pelargonic and capryonic, and the unsaturated $C_{2-9}$ monocarboxylic acids acrylic, propriolic, methacrylic, crotonic and isocrotonic acids. Exemplary dicarboxylic acids include the saturated $C_{2-9}$ dicarboxylic acids malonic, succinic, glutaric, adipic and pimelic, while unsaturated $C_{2-9}$ dicarboxylic acids include maleic, fumaric, citraconic and mesaconic acids. Exemplary tricarboxylic acids include the saturated $C_{2-9}$ tricarboxylic acids tricarballylic and 1,2,3-butanetricarboxylic acid. Additionally, the carboxylic acids of this definition may also contain one or two hydroxyl groups to form hydroxy carboxylic acids. Exemplary hydroxy carboxylic acids include glycolic, lactic, glyceric, tartronic, malic, tartaric and citric acid. Aromatic acids within this definition include benzoic and salicylic acid.

Commonly employed water soluble polyvalent metal salts which may be used to help stabilize the encapsulated polypeptides of this invention include, for example: (1) the inorganic acid metal salts of halides (e.g., zinc chloride, calcium chloride), sulfates, nitrates, phosphates and thiocyanates; (2) the aliphatic carboxylic acid metal salts (e.g., calcium acetate, zinc acetate, calcium propionate, zinc glycolate, calcium lactate, zinc lactate and zinc tartrate); and (3) the aromatic carboxylic acid metal salts of benzoates (e.g., zinc benzoate) and salicylates.

Pharmaceutical formulations of anti-CD83 agonist antibodies can be designed to immediately release an anti-CD83 agonist antibody ("immediate-release" formulations), to gradually release the antibodies over an extended period of time ("sustained-release," "controlled-release," or "extended-release" formulations), or with alternative release profiles. The additional materials used to prepare a pharmaceutical formulation can vary depending on the therapeutic form of the formulation (e.g., whether the system is designed for immediate-release or sustained-, controlled-, or extended-release). In certain variations, a sustained-release formulation can further comprise an immediate-release component to quickly deliver a priming dose following drug delivery, as well as a sustained-release component. Thus, sustained-release formulations can be combined with immediate-release formulations to provide a rapid "burst" of drug into the system as well as a longer, gradual release. For example, a core sustained-release formulation may be coated with a highly soluble layer incorporating the drug. Alternatively, a sustained-release formulation and an immediate-release formulation may be included as alternate layers in a tablet or as separate granule types in a capsule. Other combinations of different types of drug formulations can be used to achieve the desired therapeutic plasma profile.

Exemplary sustained-release dosage formulations (discussed in *Remington's Pharmaceutical Sciences* 20th Edition, supra) can include a wide variety of drug delivery systems, including those that employ: (a) a reservoir system in which the drug is encapsulated in a polymeric membrane, permitting water to diffuse through the membrane to dissolve the drug, which then diffuses out of device; (b) a matrix system (gradient or monolithic) in which the drug is suspended in a polymeric matrix and gradually diffuses out as the matrix dissolves or disintegrates; (c) micro-encapsulation and coated granule systems in which particles of drug (or particles of drug and polymer) as small as 1 micrometer ("μm"; $10^{-6}$ m) in diameter are coated in a polymeric membrane, including embodiments in which particles coated with polymers having different release characteristics (e.g., pH-dependent or non-pH-dependent polymers, compounds with different degrees of water solubility, and the like) are delivered together in a single capsule; (d) solvent-activated systems, including (i) osmotically controlled devices (e.g., OROS®, Alza Corp., Mountain View, Calif.) in which an osmotic agent and a drug are encapsulated in a semi-permeable membrane, such that an osmotic gradient pulls water into the device, and increased pressure drives drug out of device via pores in the membrane; (ii) a hydrogel swelling system in which drug is dispersed in a polymer and/or a polymer is coated onto a particle of drug, wherein the polymer swells on contact with water (in certain embodiments, swelling can be pH-dependent, pH-independent, or dependent on other physical or chemical characteristics), allowing diffusion of drug out of the device; (iii) a microporous membrane system in which drug is encapsulated in a membrane that has a component that dissolves on contact with water (in certain embodiments, swelling can be pH-dependent, pH-independent, or dependent on other physical or chemical characteristics), producing pores in the membrane through which the drug diffuses; and (iv) a wax matrix system in which the drug and an additional soluble component are dispersed in wax, such that, when water dissolves the soluble component, diffusion of drug from the system is allowed; and (e) polymeric degradation systems, including (i) bulk degradation, in which drug is dispersed in a polymeric matrix, and degradation occurs throughout the polymeric structure in a random fashion, allowing drug release; and (ii) surface erosion, in which drug is dispersed in a polymeric matrix and delivered as the surface of the polymer erodes.

E. Methods of Treatment

The invention provides methods for treating or preventing an autoimmune disease (such as inflammatory bowel disease (IBD)) in an individual comprising administering to the individual an effective amount of an anti-CD83 agonist antibody described herein. In some embodiments, the individual is a human. In some embodiments, the autoimmune disease is selected from the group consisting of rheumatoid arthritis, juvenile rheumatoid arthritis, systemic lupus erythematosus (SLE), lupus nephritis, ulcerative colitis, Wegener's disease, inflammatory bowel disease, idiopathic thrombocytopenic purpura (ITP), thrombotic thrombocytopenic purpura (TTP), autoimmune thrombocytopenia, multiple sclerosis, psoriasis, IgA nephropathy, IgM polyneuropathies, myasthenia gravis, vasculitis, diabetes mellitus, Reynaud's syndrome, Sjorgen's syndrome and glomerulonephritis. In some embodiments, the individual has is at risk of developing an autoimmune disease associated with myeloid cell activation (dendritic cell and macrophage) in the disease pathogenesis. In some embodiments, the individual has IBD or is at risk of developing IBD.

The IBD may be ulcerative colitis (UC), Crohn's disease, or indeterminate colitis. In some embodiments, an individual having IBD is one that is experiencing or has experienced one or more signs, symptoms, or other indicators of IBD or has been diagnosed with IBD. An individual having IBD may have steroid-refractory and/or steroid dependent IBD, steroid-refractory and/or steroid dependent UC or steroid-refractory and/or steroid dependent Crohn's disease. "Steroid-refractory" IBD is IBD which progresses, or worsens, even though steroid is being administered to the subject with IBD. An individual with "steroid-dependent" IBD is dependent on steroid use, and cannot taper or withdraw steroid administration without acute exacerbation of clinical symptoms.

The administration of the anti-CD83 antibody may result in a clinical response and/or disease remission. As used herein, "clinical response" refers to an improvement in the symptoms of disease. "Disease remission" indicates substantially no evidence of the symptoms of disease. The clinical response or disease remission may be achieved within a certain time frame, for example, within or at about 8 weeks from the start of treatment with, or from the initial dose of, the antagonist. Clinical response may also be sustained for a period of time; such as for ≥24 weeks, or ≥48 weeks. In some embodiments, weight loss associated with IBD may be reduced and/or eliminated by the treatment with an anti-CD83 agonist antibody. In some embodiments, the treatment with an anti-CD83 agonist antibody described herein prevents mucosal damage and/or aid in epithelial repair of gastrointestinal tissues in an individual having IBD.

Symptoms associated with IBD includes abdominal pain, vomiting, diarrhea, hematochezia (bright red blood in stools), and weight loss. Further tests may be carried out for diagnosing IBD. For example, complete blood cell count, electrolyte panel, liver function tests (LFT), fecal occult blood test, X-rays (including barium enema and upper gastrointestinal series), sigmoidoscopy, colonoscopy, and upper endoscopy may be used. Various scoring system known in the art may be used for quantitatively assessing severity of the disease.

For the prevention or treatment of disease, the appropriate dosage of an active agent (i.e., an anti-CD83 agonist antibody), will depend on the type of disease to be treated, the severity and course of the disease, whether the agent is administered for preventive or therapeutic purposes, previous therapy, the patient's clinical history and response to the agent, and the discretion of the attending physician. The particular dosage regimen, i.e., dose, timing, and repetition, will depend on the particular individual and that individual's medical history as assessed by a physician. Typically the clinician will administer an anti-CD83 agonist antibody until a dosage is reached that achieves the desired result.

Methods of the present invention are useful for treating, ameliorating or palliating the symptoms of an autoimmune disease (such as IBD) in an individual, or for improving the prognosis of an individual suffering from an autoimmune disease. The quality of life in individuals suffering from the disease may be improved, and the symptoms may be reduced or eliminated following treatment with an anti-CD83 agonist antibody. Methods of the present invention are also useful for delaying development of or preventing an autoimmune disease (such as IBD) in an individual at risk of developing the disease. Any anti-CD83 agonist antibodies described herein may be administered to the individual.

F. Combination Therapies

The methods of the invention can be combined with known methods of treatment for an autoimmune disease (such as IBD), either as combined or additional treatment steps or as additional components of a therapeutic formulation. Alternatively, different anti-CD83 agonist antibodies may be administered in combination. The type of combination therapy selected will depend on the clinical manifestations of the disease.

For example, IBD (such as ulcerative colitis, Crohn's disease, or indeterminate colitis) can be treated by combination therapy comprising administration of an anti-CD83 agonist antibody in conjunction with a second medicament for IBD. The type of such second medicament depends on various factors, including the type of IBD, the severity of the IBD, the condition and age of the subject, the type and dose of first medicament employed, etc. In some embodiments, the second medicament includes one or more of an aminosalicylate, a corticosteroid, and an immunosuppressive agent. In some embodiments, the aminosalicylate is one of sulfasalazine, olsalazine, mesalamine, balsalazide, and asacol. In some embodiments, multiple aminosalicylates are co-administered, such as a combination of sulfasalazine and olsalazine. In some embodiments, the corticosteroid is budesonide, prednisone, prednisolone, methylprednisolone, 6-mercaptopurine (6-MP), azathioprine, methotrexate, or cyclosporin. In some embodiments, the second medicament is an antibiotic, such as ciprofloxacin and/or metronidazole; or an antibody-based agent such as infliximab (Remicade®).

All these second medicaments may be used in combination with each other or by themselves with the first medicament, so that the expression "second medicament" as used herein does not mean it is the only medicament besides the first medicament, respectively. Thus, the second medicament need not be one medicament, but may constitute or comprise more than one such drug.

These second medicaments as set forth herein are generally used in the same dosages and with administration routes as used hereinbefore or about from 1 to 99% of the heretofore-employed dosages. If such second medicaments are used at all, optionally, they are used in lower amounts than if the first medicament were not present, especially in subsequent dosings beyond the initial dosing with the first medicament, so as to eliminate or reduce side effects caused thereby.

Combined administration herein includes co-administration, using separate formulations or a single pharmaceutical formulation, and consecutive administration in either order, wherein preferably there is a time period while both (or all) active agents simultaneously exert their biological activities.

G. Pharmaceutical Dosages

Dosages and desired drug concentration of pharmaceutical compositions of the present invention may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles laid down by Mordenti, J. and Chappell, W. "The Use of Interspecies Scaling in Toxicokinetics," In *Toxicokinetics and New Drug Development*, Yacobi et al., Eds, Pergamon Press, New York 1989, pp. 42-46.

For in vivo administration of the polypeptides or antibodies described herein, normal dosage amounts may vary from about 10 ng/kg up to about 100 mg/kg of an individual's body weight or more per day, preferably about 1 mg/kg/day to 10 mg/kg/day, depending upon the route of administration. For repeated administrations over several days or longer, depending on the severity of the disease or disorder to be treated, the treatment is sustained until a desired suppression of symptoms is achieved.

An exemplary dosing regimen comprises administering an initial dose of an anti-CD83 agonist antibody of about 2 mg/kg, followed by a weekly maintenance dose of about 1 mg/kg every other week. Other dosage regimens may be useful, depending on the pattern of pharmacokinetic decay that the physician wishes to achieve. For example, dosing an individual from one to twenty-one times a week is contemplated herein. In certain embodiments, dosing ranging from about 3 µg/kg to about 2 mg/kg (such as about 3 µg/kg, about 10 µg/kg, about 30 µg/kg, about 100 µg/kg, about 300 µg/kg, about 1 mg/kg, and about 2/mg/kg) may be used. In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. Progress of the therapy is easily monitored by conventional techniques and assays. The dosing regimen, including the anti-CD83 agonist antibody administered, can vary over time independently of the dose used.

Dosages for a particular anti-CD83 agonist antibody may be determined empirically in individuals who have been given one or more administrations of anti-CD83 agonist antibody. Individuals are given incremental doses of an anti-CD83 agonist antibody. To assess efficacy of an anti-CD83 agonist antibody, a clinical symptom of an autoimmune disease (such as IBD) can be monitored.

Administration of an anti-CD83 agonist antibody according to the methods of the invention can be continuous or intermittent, depending, for example, on the recipient's physiological condition, whether the purpose of the administration is therapeutic or prophylactic, and other factors known to skilled practitioners. The administration of an anti-CD83 agonist antibody may be essentially continuous over a preselected period of time or may be in a series of spaced doses, e.g., either during or after development of an autoimmune disease (such as ulcerative colitis, and Crohn's disease).

Guidance regarding particular dosages and methods of delivery is provided in the literature; see, for example, U.S. Pat. Nos. 4,657,760; 5,206,344; or 5,225,212. It is within the scope of the invention that different formulations will be effective for different treatments and different disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

H. Administration of the Formulations

The formulations of the present invention (e.g., formulations of anti-CD83 agonist antibodies), including, but are not limited to reconstituted formulations, are administered to an individual in need of treatment with an anti-CD83 agonist antibody, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes.

In preferred embodiments, the formulations are administered to the individual by subcutaneous (i.e. beneath the skin) administration. For such purposes, the formulation may be injected using a syringe. However, other devices for administration of the formulation are available such as injection devices (e.g. the INJECT-EASE™ and GEN-JECT™ devices); injector pens (such as the GENPEN™); auto-injector devices, needleless devices (e.g. MEDIJECTOR™ and BIOJECTOR™); and subcutaneous patch delivery systems.

The appropriate dosage (an "effective amount") of the anti-CD83 agonist antibody will depend, for example, on the condition to be treated, the severity and course of the condition, whether the anti-CD83 agonist antibody is administered for preventive or therapeutic purposes, previous therapy, the patient's clinical history and response to the anti-CD83 agonist antibody, the type of the anti-CD83 agonist antibody used, and the discretion of the attending physician. The anti-CD83 agonist antibody is suitably administered to the patient at one time or over a series of treatments and may be administered to the patient at any time from diagnosis onwards. The anti-CD83 agonist antibody may be administered as the sole treatment or as part of a combination therapy in conjunction with other drugs or therapies useful in treating an autoimmune disease (such as IBD).

For an anti-CD83 agonist antibody, about 0.1 mg/kg to about 20 mg/kg may be an initial candidate dosage for administration to an individual, whether, for example, by one or more separate administrations. However, other dosage regimens may be useful. The progress of this therapy is easily monitored by conventional techniques.

Uses for an anti-CD83 agonist antibody formulation include the treatment or prophylaxis of an autoimmune disease (such as IBD). Depending on the severity of the disease to be treated, a therapeutically effective amount (e.g., from about 1 mg/kg to about 15 mg/kg) of the anti-CD83 agonist antibody is administered to the individual.

I. Articles of Manufacture and Kits

In another aspect, an article of manufacture or kit is provided which contains an anti-CD83 agonist antibody formulation and preferably provides instructions for its use in the methods of the invention. Thus, in certain embodiments, the article of manufacture or kit comprises instructions for the use of an anti-CD83 agonist antibody in methods for treating or preventing autoimmune disease such as IBD (including ulcerative colitis and Crohn's disease) in an individual comprising administering to the individual an effective amount of an anti-CD83 agonist antibody. In certain embodiments, the individual is a human.

The article of manufacture or kit may further comprise a container. Suitable containers include, for example, bottles, vials (e.g., dual chamber vials), syringes (such as single or dual chamber syringes) and test tubes. The container may be formed from a variety of materials such as glass or plastic. The container holds the formulation. The article of manufacture or kit may further comprises a label or a package insert, which is on or associated with the container, may indicate directions for reconstitution and/or use of the formulation. The label or package insert may further indicate that the formulation is useful or intended for subcutaneous or other modes of administration for treating or preventing an autoimmune disease (such as IDB) in an individual. The container holding the formulation may be a single-use vial or a multi-use vial, which allows for repeat administrations (e.g. from 2-6 administrations) of the reconstituted formulation. The article of manufacture or kit may further comprise a second container comprising a suitable diluent (e.g., BWFI). Upon mixing the diluent and the lyophilized formulation, the final protein, polypeptide, or small molecule concentration in the reconstituted formulation will generally be at least 50 mg/ml. The article of manufacture or kit may further include other materials desirable from a commercial, therapeutic, and user standpoint, including other buffers, diluents, filters, needles, syringes, and package inserts with instructions for use.

The article of manufacture or kit herein optionally further comprises a container comprising a second medicament, wherein the anti-CD83 agonist antibody is a first medicament, and which article further comprises instructions on the package insert for treating the subject with the second medicament, in an effective amount. The second medicament may be any of those set forth above, with an exemplary second medicament being an aminosalicylate, an oral corticosteroid, 6-mercaptopurine (6-MP), and azathioprine if the anti-CD83 antibody is used for treating IBD.

In another embodiment, provided herein is an article of manufacture or kit comprising the formulations described herein for administration in an auto-injector device. An auto-injector can be described as an injection device that upon activation, will deliver its contents without additional necessary action from the patient or administrator. They are particularly suited for self-medication of therapeutic formulations when the delivery rate must be constant and the time of delivery is greater than a few moments.

The invention will be more fully understood by reference to the following examples. They should not, however, be construed as limiting the scope of the invention. All citations throughout the disclosure are hereby expressly incorporated by reference.

EXAMPLES

CD83 is a well-conserved type-1 membrane protein of the Ig superfamily found primarily on the surface of mature dendritic cells (DCs). Soluble CD83 has immunosuppressive activity, however, the function of CD83 on DCs and its putative ligand remains unknown. We have identified a CD83 homotypic interaction that elicits anti-inflammatory effects on DCs. Treatment with soluble CD83 or anti-CD83 antibody during DC maturation resulted in decreased expression of surface activation markers and secretion of proinflammatory cytokines, such as IL-12p40. Knockdown of surface CD83 expression, or truncation of the cytoplasmic region, abrogated the response to CD83 treatment demonstrating that CD83 homotypic interaction mediates inhibition of inflammation. MAPK and mTOR signaling function downstream of this repression as CD83 treatment inhibits phosphorylation of mTOR and p38α, which are necessary for surface activation marker expression and IL-12p40 production. CD83 immunosuppression is pivotal in maintaining the balance between tolerance and immunity, as mice overexpressing CD83 at the mucosal surface are more resistant to colitis, leading to weight retention and decreased serum cytokine levels. Thus, a CD83 homotypic interaction regulates DC immune response, preventing inappropriate inflammation and promoting tolerance.

Example 1

CD83 Engages in Homotypic Binding at the Cell Surface

To determine if soluble CD83 bound to CD83 expressed on the cell surface, CD83.fc comprising the amino acid sequence

```
                                        (SEQ ID NO: 3)
TPEVKVACSEDVDLPCTAPWDPQVPYTVSWVKLLEGGEERMETPQEDHLR

GQHYHQKGQNGSFDAPNERPYSLKIRNTTSCNSGTYRCTLQDPDGQRNLS

GKVILRVTGCPAQRKEETFKKYGRAQVTDKAAHYTLCPPCPAPELLGGPS

VFLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISKA

KGQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQK

SLSLSPGK
``` was produced and assayed for its ability to bind either human CD83 stably expressed on CHO cells (CHO-hCD83) or endogenous CD83 expressed on MUTZ-3 derived mature dendritic cells (mDCs). To generate an expression vector for the production of the stable CHO-hCD83 cell line, a DNA fragment encoding an N-terminal HIS-tagged human CD83 (hCD83) was cloned into the neomycin-resistance plasmid, pRKneo (Crowley et al., *Proc Natl Acad Sci USA.*, 90(11): 5021-5025, 1993), at the XbaI and XhoI sites to produce hCD83.pRKneo. CHO cells were transfected with hCD83.pRKneo using Fugene (Roche) and the top 10% of CD83 positive cells were sorted by FACS then selected with G418 (400 ug/ml; GIBCO) to generate the stable CHO-hCD83 cell line. To derive immature DCs (iDCs) from MUTZ-3 cells, cells were cultured in MEMα+glutamax/ 20% heat-inactivated FBS containing 150 ng/ml rhGM-CSF and 50 ng/ml rhIL-4 for 6 days. DCs were matured for surface expression of CD83 with a cytokine cocktail containing 25 ng/ml rhIL-1β, 100 ng/ml rhIL-6, 50 ng/ml rhTNFα and 1 µg/ml PGE-2.

CD83 expression on CHO-hCD83 cells and MUTZ-3 derived mDCs was confirmed by staining cells with fluorochrome conjugated antibodies to CD83 and analyzing the cells by flow cytometry on a LSR II flow cytometry using FACSDiva software (Becton Dickinson). Labeled isotype-matched antibodies were used to determine the level of non-specific staining. Data analysis and construction of histograms showing total binding using FlowJo v.8.4.5 demonstrated that CD83 was expressed on the surface of stably transfected CHO-hCD83 cells (black line) but not on control CHO cells (dashed line) (FIG. 1A). CD83 was expressed on MUTZ-3 derived mDC (black line), but at very low levels on iDC (gray line) (FIG. 1B). Solid histograms represent isotype controls. Following confirmation of cell surface CD83 expression, CHO cells and CHO-hCD83 cells were fixed in 4% PFA for 5 minutes followed by washing with cold 1×PBS. Cells were resuspended in a FACS buffer containing PBS/2% BSA/2 mM EDTA and incubated with 1 µg PE-labeled CD83.Fc or labeled IgG.Fc control protein for 30 minutes on ice in the dark. Cells were washed with FACS buffer and analyzed by flow cytometry. For iDCs and mDCs, cells were labeled with 10 µg/ml PE-labeled CD83.Fc or labeled IgG.Fc control protein prior to fixation and flow cytometry. Data analysis demonstrated that CD83.fc bound to CHO-hCD83 (black line), but did not bind to control CHO cells (dashed line) (FIG. 1C). Furthermore, CD83.fc bound to mature DC (black line) but not to immature DC (gray line) (FIG. 1D). These results demonstrate that soluble CD83.fc specifically binds to cells expressing CD83 on the cell surface.

Figure 2:
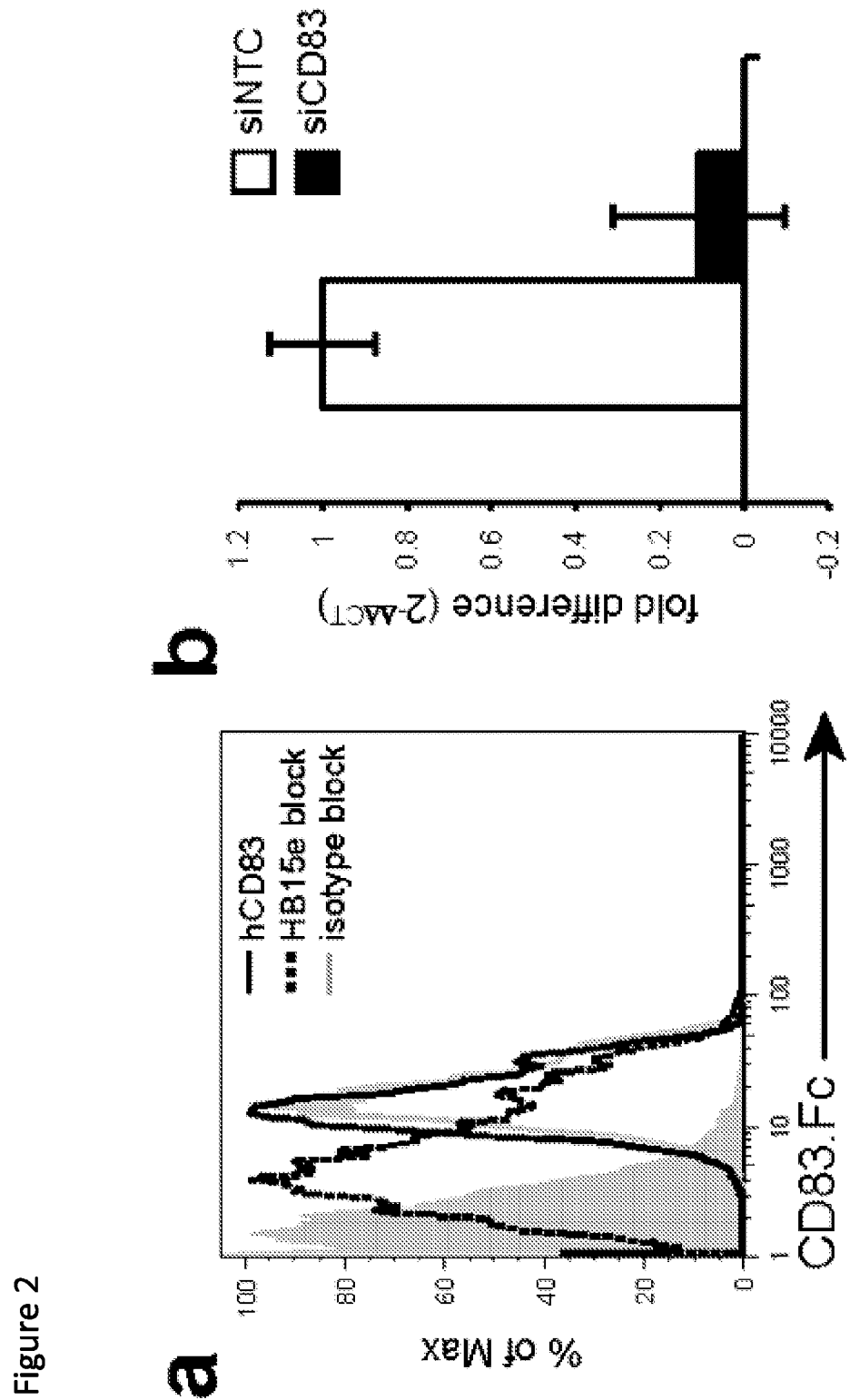
FIG. 2 shows that CD83 was necessary for binding of CD83.fc. (a) CD83.fc bound to CHO-hCD83 cells but binding was blocked by anti-CD83 antibody as quantified by flow cytometry. (b) Efficacy of siRNA specific to CD83 (siCD83) in MUTZ-3 mature DCs as depicted by taqman analysis of total RNA normalized to 18S. (c) CD83 was expressed on the surface of mature DC treated with non-targeting control (siNTC) siRNA, but not on mature DCs treated with siCD83. (d) CD83.fc bound to mDC but binding was abrogated by siCD83 treatment. (e) Knock down of CD83 decreased surface expression of MHCII in mature DCs. (f) Knock down of CD83 did not alter surface expression of CD86 in mature DCs.
Figure 2:
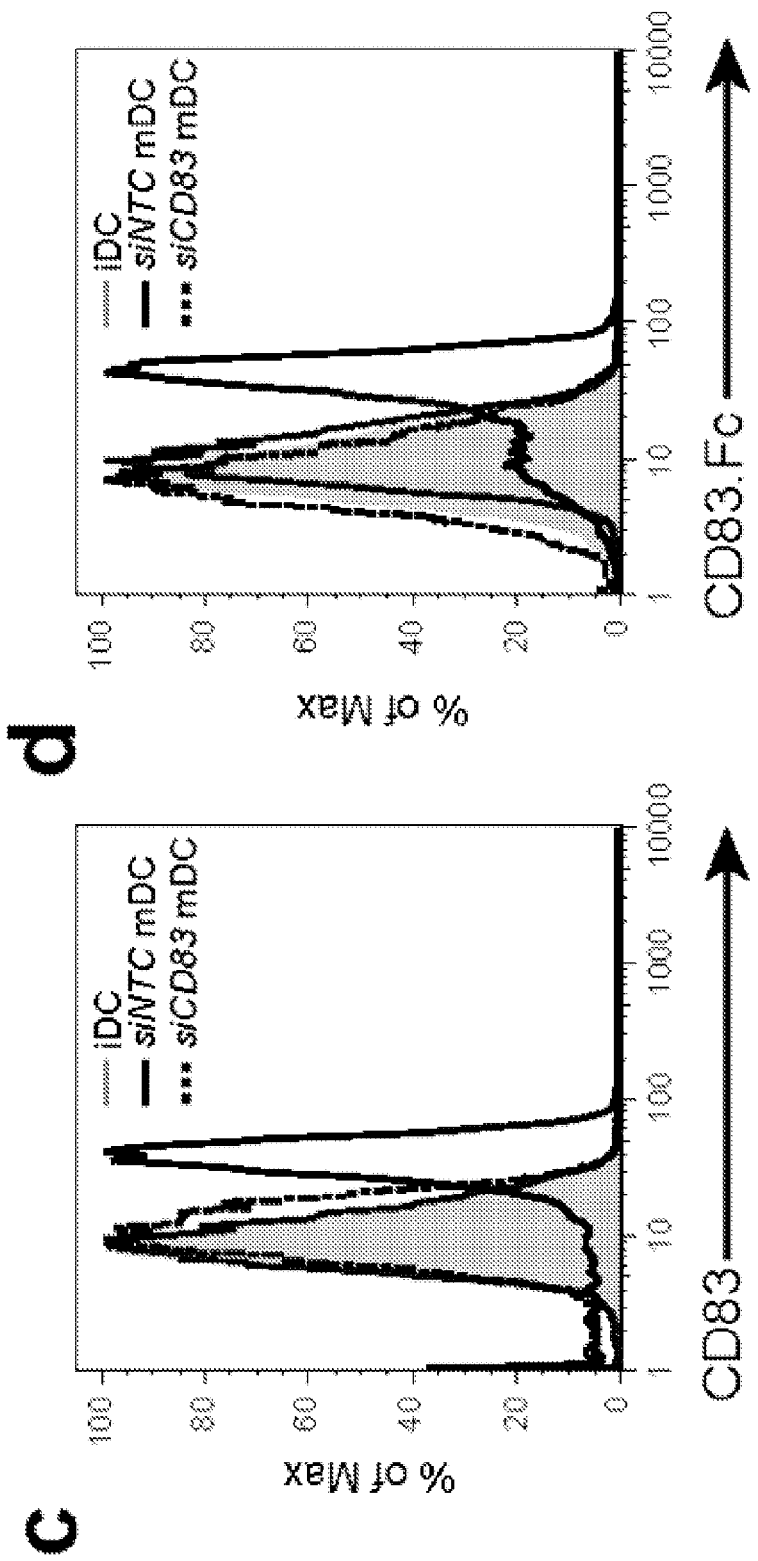
Figure 2:
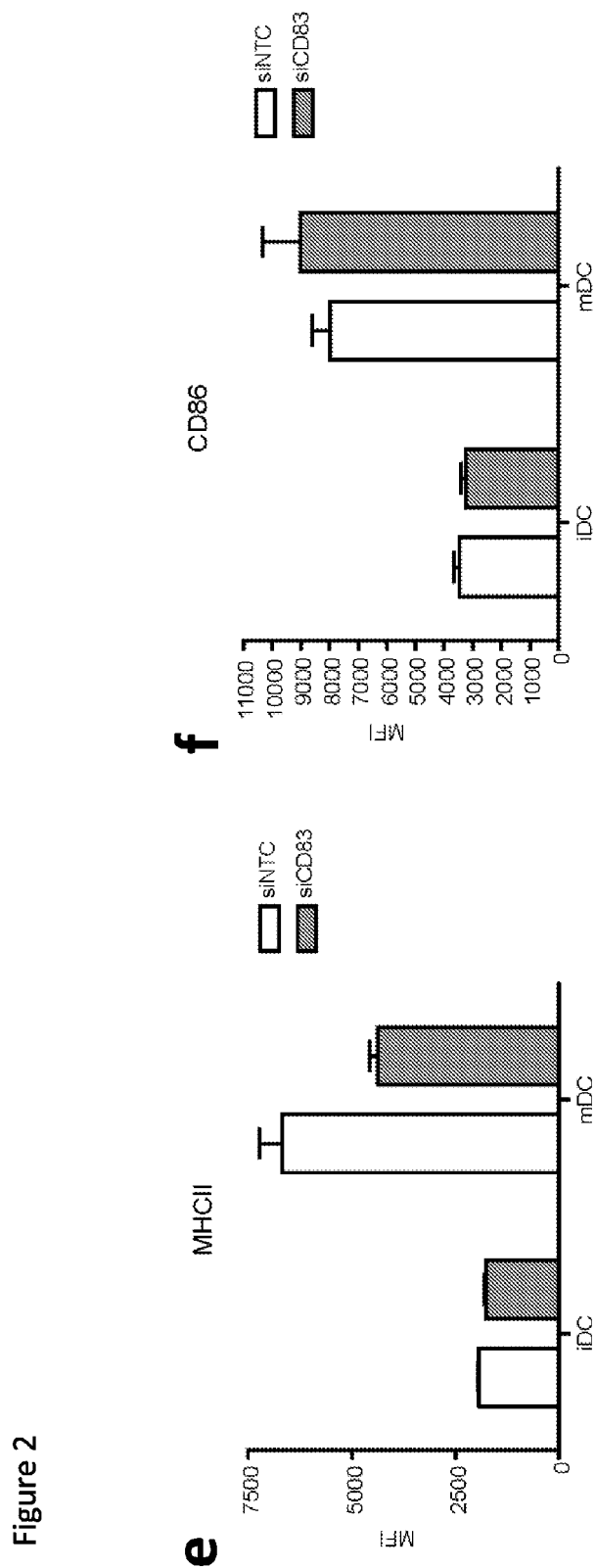

To confirm that cell surface CD83 is necessary for CD83.fc binding, CHO-hCD83 cells were incubated with 1 µg/ml anti-CD83 antibody (HB15e; Santa Cruz Biotechnology) to determine if it blocks CD83.fc binding. Data analysis demonstrated that CD83.fc binds to CHO-hCD83 cells (black line) but binding is blocked by HB15e (dashed line), but not isotype control (gray line) (FIG. 2A). The requirement for CD83 expression in order for CD83.fc binding was further assayed in MUTZ-3 derived DCs not expressing CD83. MUTZ-3 iDCs were transfected with Accell siRNA targeting CD83 (Cat. No. E-012680; Dharmacon) or non-targeting controls (Cat. No. D-001910; Dharmacon) four days after culture in MEMα+ glutamax/20% heat-inactivated FBS containing 150 ng/ml rhGM-CSF and 50 ng/ml rhIL-4 MUTZ-3 iDCs were incubated for 72 hrs at 37° C. with 5% $CO_2$ in Accell delivery media (Cat. No. B-005000; Dharmacon) containing 10 uM siRNAs and supplemented with 3% heat-inactivated FBS, 150 ng/ml GM-CSF and 50 ng/ml IL-4. At day 7, DCs were treated with a maturation stimulus to produce mDCs as described above. Efficacy of siRNA mediated knockdown of CD83 RNA and protein expression, was assessed by taqman qPCR and well as western blot of total cell lysates, respectively. Analysis of total RNA from MUTZ-3 mDCs treated with non-targeting control (siNTC) siRNA or siRNA specific to CD83 (siCD83) normalized to 18S demonstrated that DCs transfected with CD83 siRNA exhibited a significant downregulation of CD83 RNA levels (FIG. 2B). Knockdown of CD83 in MUTZ-3 mDCs was confirmed by staining cells with fluorochrome conjugated antibodies to CD83 and analyzing the cells by flow cytometry. Data analysis and construction of histograms showing total binding demonstrated that CD83 was expressed on the surface of mDC treated with siNTC (black line), but not on iDC (gray line) or mature DCs treated with siCD83 (dashed line) (FIG. 2C). Solid histograms represent isotype controls. After confirming knockdown of CD83 expression, iDC, siNTC mDC, and siCD83 mDC were incubated with PE-labeled CD83.Fc or labeled IgG.Fc control protein as described above, and subjected to flow cytometry. Data analysis demonstrated that CD83.fc bound to siNTC mDC but not iDC or siCD83 mDC, signifying that CD83.fc binding to mature DCs requires CD83 expression (FIG. 2D). Knock down of CD83 also resulted in decreased expression of MHCII, but no changes in other activation markers such as CD86 (FIGS. 2E and F).

Figure 3:
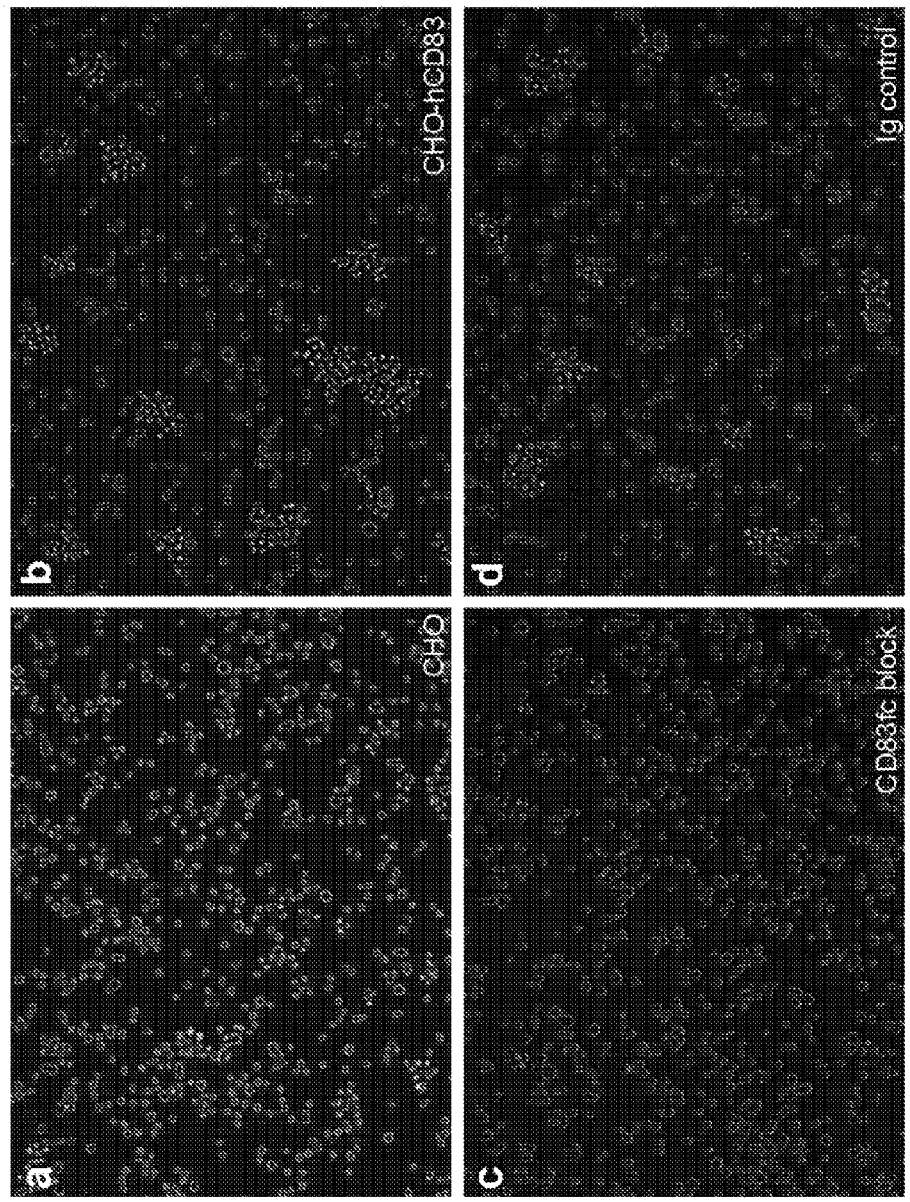
FIG. 3 provides microscopy images at 10× showing that CD83 expression resulted in cell aggregation in suspension culture. (a) Control CHO cells did not aggregate. (b) Cells expressing CD83 formed clusters while in suspension culture. (c) Pre-treatment of CHO-hCD83 cells with CD83.fc protein blocked aggregation. (d) Pre-treatment of CHO-hCD83 cells with Ig control protein did not block aggregation.

To determine if CD83 mediates cell to cell adhesion through homotypic binding, cell aggregation was assayed in CHO cells expressing hCD83. CHO cells and CHO-hCD83 cells were detached from flasks with 2 mM EDTA, washed and resuspended in HBSS medium containing 2% FBS/10 mM EDTA but lacking $Ca^{2+}$ or $Mg^{2+}$. The cells were subsequently resuspended at $10^6$/ml and passed through a 70 µm filter to obtain a single cell suspension for plating on low adhesion 10 cm culture dishes. Following incubation at 37° C. for 90 minutes in an orbital platform shaker, the cells were fixed with 4% PFA to assess for cell aggregation. Microscopic imaging of cells demonstrated that control CHO cells lacking CD83 expression did not aggregate, but CHO-hCD83 cells expressing hCD83 formed clusters while in suspension culture (FIGS. 3A and B) Pre-treatment of CHO-hCD83 cells with 1 µg CD83.fc protein blocked aggregation, while treatment with Ig control did not (FIGS. 3C and D). These results demonstrate that surface expression of CD83 is sufficient for cell to cell adhesion and that this interaction can be blocked by addition of soluble CD83 due to competition for homotypic binding.

Example 2

Figure 4:
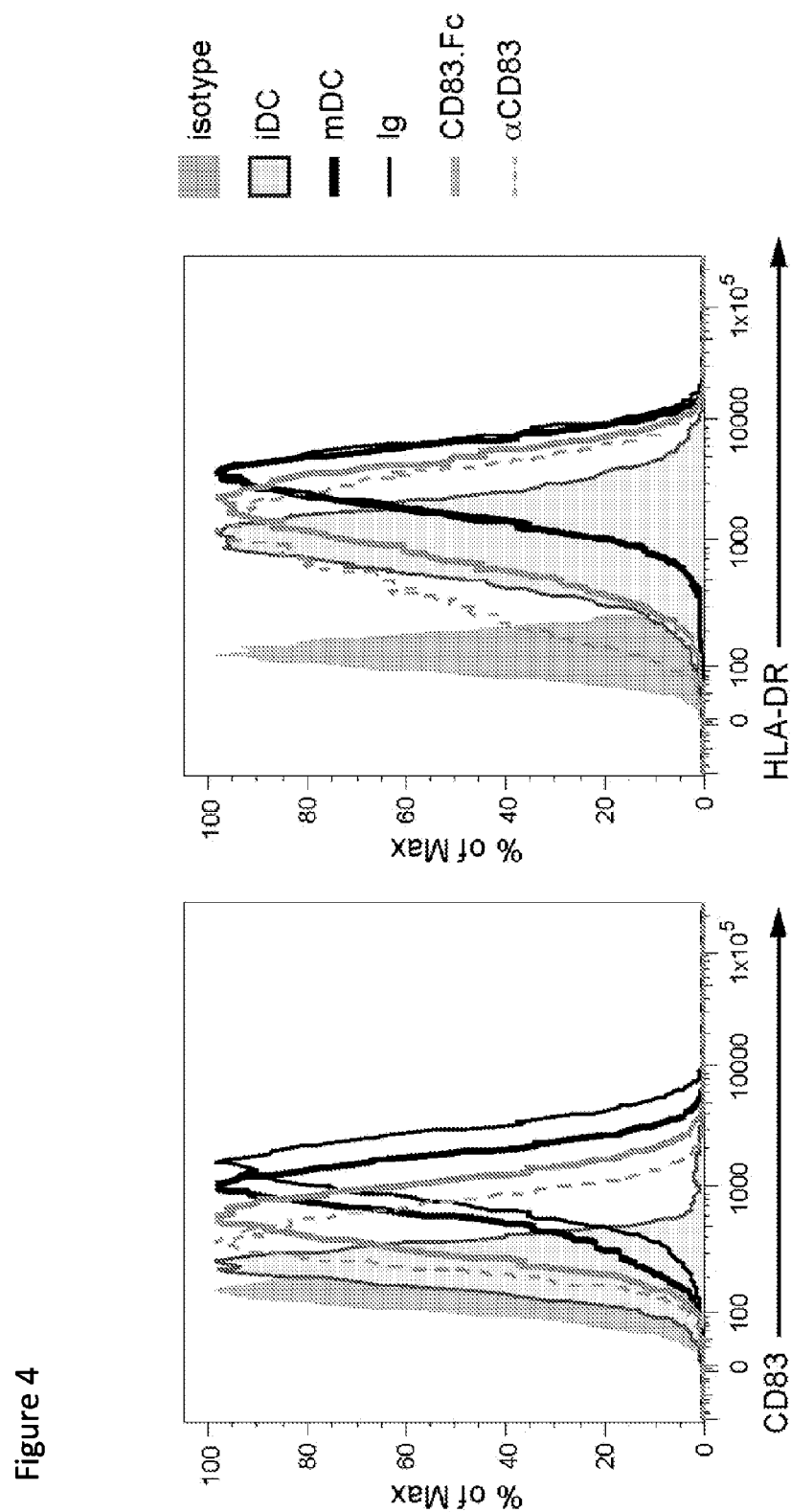
FIG. 4 shows that CD83 treatment in mature DCs with CD83.fc or HB15e antibody decreased expression of the surface activation markers CD83 and HLA-DR.

Soluble CD83 Treatment of DCs Results in an Anti-Inflammatory Phenotype by Inhibiting DC Maturation and Proinflammatory Cytokine Release To characterize the immune response induced in DCs by soluble CD83 treatment, the effect of CD83 treatment on mDC surface activation markers was assessed. To derive iDCs from MUTZ-3 cells, cells were cultured in MEMα+ glutamax/20% heat-inactivated FBS containing 150 ng/ml rhGM-CSF and 50 ng/ml rhIL-4 for 6 days. iDCs were treated with a maturation stimulus cytokine cocktail containing 25 ng/ml rhIL-1β, 100 ng/ml rhIL-6, 50 ng/ml rhTNFα and 1 µg/ml PGE-2. Treatment of mDCs with 10 µg/ml CD83.fc, HB15e, or control IgG.fc was given simultaneously with the maturation stimulus. Expression of cell surface activation markers, CD83 and HLA-DR (MHCII), on MUTZ-3 derived mDCs was examined by staining cells with fluorochrome conjugated antibodies to CD83 or MHCII, and analyzing the cells by flow cytometry. Labeled isotype-matched antibodies were used to determine the level of non-specific staining. Data analysis and construction of histograms showing total binding demonstrated that CD83 and MHCII was expressed on MUTZ-3 derived mDC (black line), but at low levels on iDC (solid lined histogram) (FIG. 4). Solid unlined histograms represent isotype controls. Expression of both CD83 and MHCII was decreased with either CD83.fc (gray line) or HB15e (dashed line) treatment, indicating that CD83 treatment decreases expression of surface activation markers in mDCs.

Figure 5:
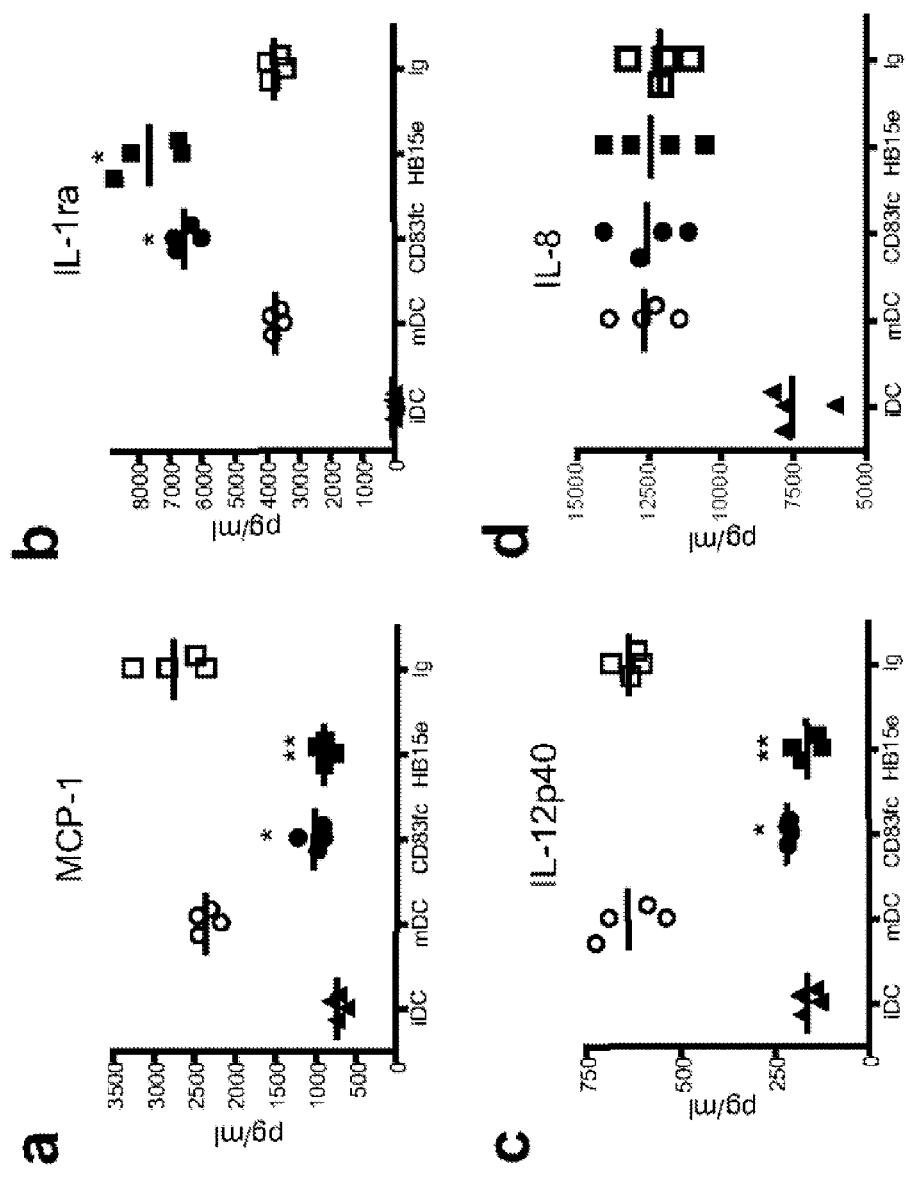
FIG. 5 ELISA data showed altered cytokine release in CD83 treated human monocyte derived DCs. (a and c) Pro-inflammatory cytokines IL12-p40 and MCP-1 were decreased upon CD83.fc or HB15e antibody treatment. (b) Anti-inflammatory cytokine IL-1ra was significantly increased in CD83 treated DCs. (d) IL-8 showed no difference among CD83 treated or control treated DCs. * indicates values are significantly different; * p<0.01, ** p<0.001. Graphs representative of at least four different donors.

As DCs are known to regulate the immune response through the production of cytokines, the effect of soluble CD83 treatment on DCs was assessed by detection of cytokine secretion from treated human monocyte-derived DCs (MDDCs). MDDCs were isolated from whole blood of multiple donors and stimulated with cytokines to drive maturation in the presence or absence of CD83.Fc or HB15e. For isolation and treatment, human whole blood was diluted with PBS, layered on Ficoll histopaque (GE healthcare) and spun at 1500 rpm for 30 minutes. The leukocyte layer was removed and washed with PBS. Monocytes were isolated with Human monocyte isolation kit II (Miltenyi) and cultured for 6 days in RPMI/10% FBS/1× pen/strep containing 125 ng/ml rhIL-4 and 50 ng/ml rhGM-CSF (R&D systems). The media was changed every other day to derive immature DC. All treatments with 10 µg/ml CD83.Fc or 1 µg/ml anti-CD83 antibody (HB15e; Santa Cruz) were given simultaneously with the maturation stimulus. Cell culture supernatants were collected 48 hours after maturation of DCs and secreted cytokines were analyzed by ELISA using kits for MCP-1, IL-12p40 and IL-8 (Invitrogen), as well as IL-1ra (Cell Sciences) detection according to standard manufacturer's instructions. Analysis of cytokines secreted by DCs demonstrated that treatment with CD83.Fc together with the maturation stimulus altered DC cytokine secretion with an increase in interleukin-1 receptor antagonist (IL-1Ra) (FIG. 5B), which binds the IL-1 receptor and blocks downstream inflammatory signaling, and a decrease in the production of pro-inflammatory cytokines monocyte chemotactic protein-1 (MCP-1) and subunit beta of interleukin-12 (IL-12p40) (FIGS. 5A and C). Treatment with CD83.Fc or HB15e had no effect on the production of the inflammatory cytokine IL-8 (FIG. 5D).

Figure 6:
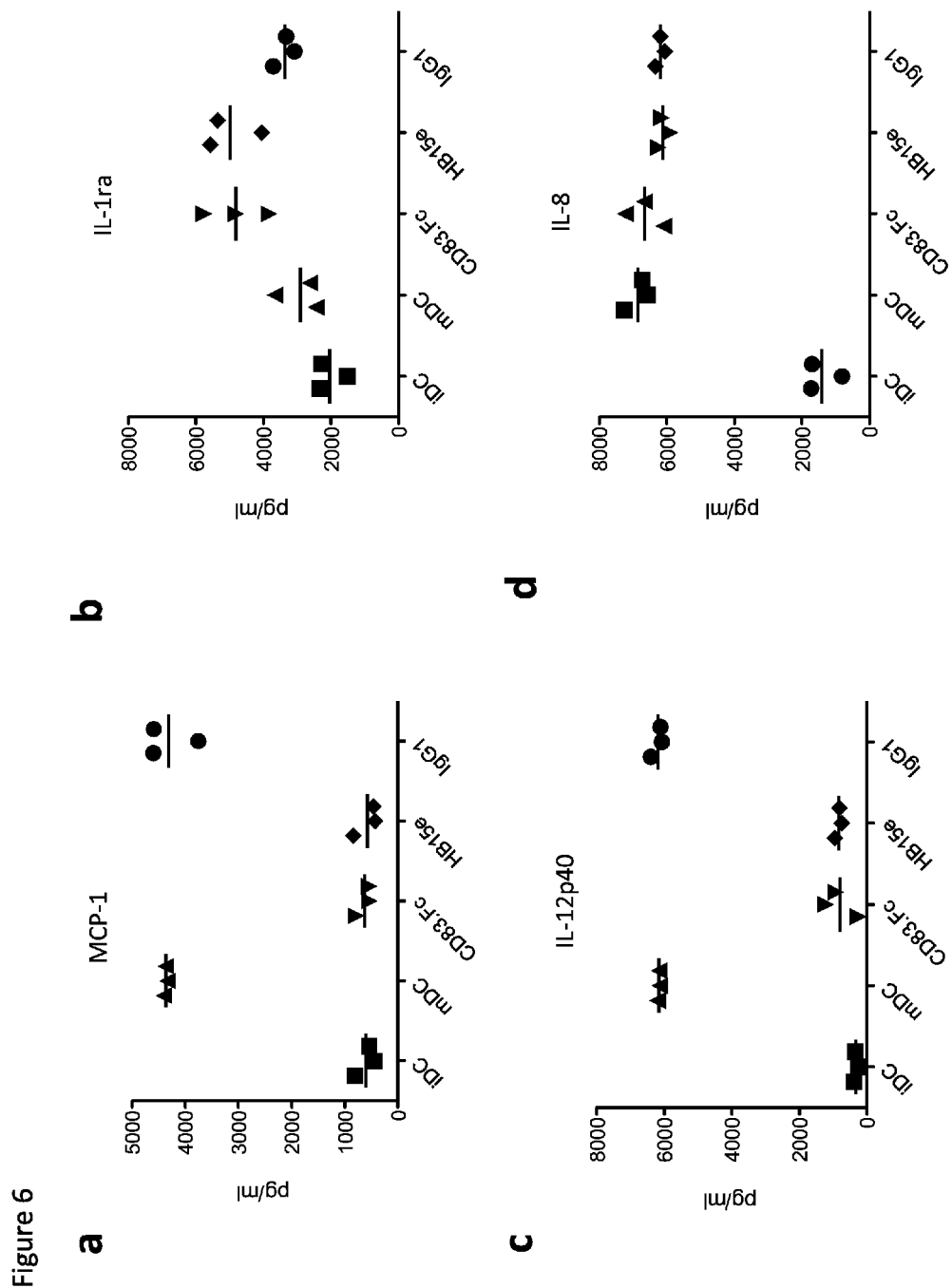
FIG. 6 ELISA data showed altered cytokine release in CD83 treated MUTZ-3 derived DCs. (a and c) Pro-inflammatory cytokines IL12-p40 and MCP-1 were decreased upon CD83.fc or HB15e antibody treatment. (b) Anti-inflammatory cytokine IL-1ra was significantly increased in CD83 treated DCs. (d) IL-8 showed no difference among CD83 treated or control treated DCs. Supernatants from each well were run in triplicate.

To further characterize the immune response induced in DCs by soluble CD83 treatment, the effect of CD83 treatment on pro-inflammatory cytokine secretion by mDCs was assessed. To derive immature DCs from MUTZ-3 cells, cells were cultured in MEMα+glutamax/20% heat-inactivated FBS containing 150 ng/ml rhGM-CSF and 50 ng/ml rhIL-4 for 6 days. DCs were matured for surface expression of CD83 with a cytokine cocktail containing 25 ng/ml rhIL-1β, 100 ng/ml rhIL-6, 50 ng/ml rhTNFα and 1 µg/ml PGE-2. Treatment of mDCs with 10 µg/ml CD83.fc, 1 µg/ml HB15e, or control IgG.fc was given simultaneously with the maturation stimulus. Cell culture supernatants were collected 48 hours after maturation of DCs and secreted cytokines were analyzed by ELISA using MCP-1, IL-12p40 and IL-8 kits (Invitrogen), as well as IL-1ra (Cell Sciences) according to standard manufacturer's instructions. Analysis of cytokines secreted by DCs demonstrated that pro-inflammatory cytokines MCP-1 (FIG. 6A) and IL-12p40 (FIG. 6C) were decreased in mDCs upon CD83.fc or HB15e treatment. In contrast, the anti-inflammatory cytokine IL-1ra was significantly increased in CD83 treated mDCs (FIG. 6B). Levels of released IL-8 demonstrated no difference among CD83 treated or control treated mDCs (FIG. 6D). Supernatants from each well were run in triplicate and * indicates values are significantly different *p<0.01, **p<0.001. Each dot represents the average of an individual well. Graphs are representative of at least three independent experiments.

To further characterize the expression the anti-inflammatory phenotype of DCs treated with CD83.fc or HB15e, microarray analysis was conducted on RNA isolated from DCs after treatment. Statistical analysis of microarrays was done using software from the R project (http://r-project.org) and the Bioconductor project (http://bioconductor.org). Background subtracted microarray data were LOESS normalized within arrays and quantile normalized between arrays. Normalized data were then log 2-transformed, and probes were filtered using the Bioconductor 'genefilter' package such that only probes that mapped to Entrez genes were retained. A non-specific filter that removed the 50% least variable probes was then applied (Bourgon et al., Proc Natl Acad Sci USA., 107(21):9546-51, 2010). To identify differentially expressed genes, the limma package was used (Smyth., Stat Appl Genet Mol Biol., 3:Article 3, 2004), to calculate attenuated t-statistics. The linear model tested for differential expression between the immature and mature DCs, as well as differences between the CD83-ligated samples (CD83fc- and HB15e-treated mature DCs) and control samples (IgG- and untreated mature DCs). The false discovery rate (FDR) was calculated using the Benjamini-Hochberg method. Genes were considered differentially expressed if they had an FDR less than 0.01. Analysis all gene expression changes of DCs from 5 different donors indicated that CD83.fc or HB15e treatment resulted in an anti-inflammatory phenotype. Overall, measurement of DC cytokine release and gene expression upon CD83.fc or HB15e treatment demonstrates that soluble CD83 treatment inhibits secretion of pro-inflammatory cytokines and induces an anti-inflammatory response.

Example 3

Figure 7:
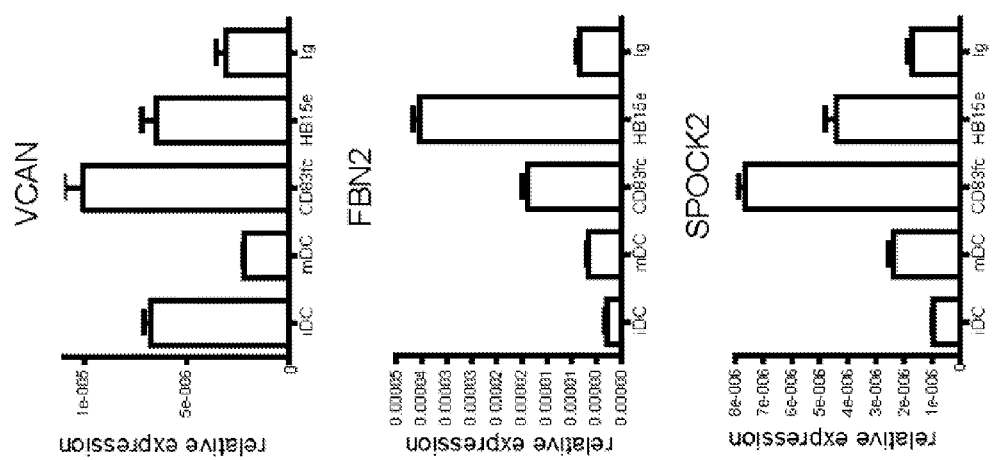
FIG. 7 shows that CD83 treatment in DCs with CD83.fc or HB15e antibody resulted in the upregulation of genes involved in wound healing as provided by Taqman qPCR analysis of vcan, spock2, and fbn2 normalized to gapdh. Average relative expression $(2^{\wedge}\Delta CT)$+SEM.

Soluble CD83 Treatment Results in the Upregulation of Genes Involved in Wound Healing To further characterize alterations in gene expression induced in DCs treated with CD83.fc or HB15e, microarray analysis was conducted on RNA isolated from DCs after treatment. Statistical analysis of microarrays was done using software from the R project (http://r-project.org) and the Bioconductor project (http://bioconductor.org). Background subtracted microarray data were LOESS normalized within arrays and quantile normalized between arrays. Normalized data were then log 2-transformed, and probes were filtered using the Bioconductor 'genefilter' package such that only probes that mapped to Entrez genes were retained. A non-specific filter that removed the 50% least variable probes was then applied (Bourgon et al., Proc Natl Acad Sci USA., 107(21):9546-51, 2010). To identify differentially expressed genes, the limma package was used (Smyth., Stat Appl Genet Mol Biol., 3:Article 3, 2004), to calculate attenuated t-statistics. The linear model tested for differential expression between the immature and mature DCs, as well as differences between the CD83-ligated samples (CD83fc- and HB15e-treated mature DCs) and control samples (IgG- and untreated mature DCs). The false discovery rate (FDR) was calculated using the Benjamini-Hochberg method. Genes were considered differentially expressed if they had an FDR less than 0.01. Analysis of DCs from 5 different donors showed that CD83.fc and HB15e treated cells segregated and clustered independently from untreated mDCs as well as iDCs and indicated that treatment resulted in an upregulation of genes involved in wound healing. The microarray data was confirmed by taqman qPCR analysis of isolated total RNA from mDCs treated with CD83.fc or HB15e (FIG. 7). Gene expression analysis after normalization to gapdh demonstrated that genes involved in wound healing, vcan, spock2, and fbn2, were upregulated. The indicated average relative expression is 2^ΔCT+standard error of the mean (SEM). These in vitro results indicate that soluble CD83 treatment may promote healthy cell proliferation and migration in vivo for healing of tissue damage caused by inflammatory diseases.

Example 4

The CD83 Homotypic Interaction Mediates the Anti-Inflammatory Response

Figure 8:
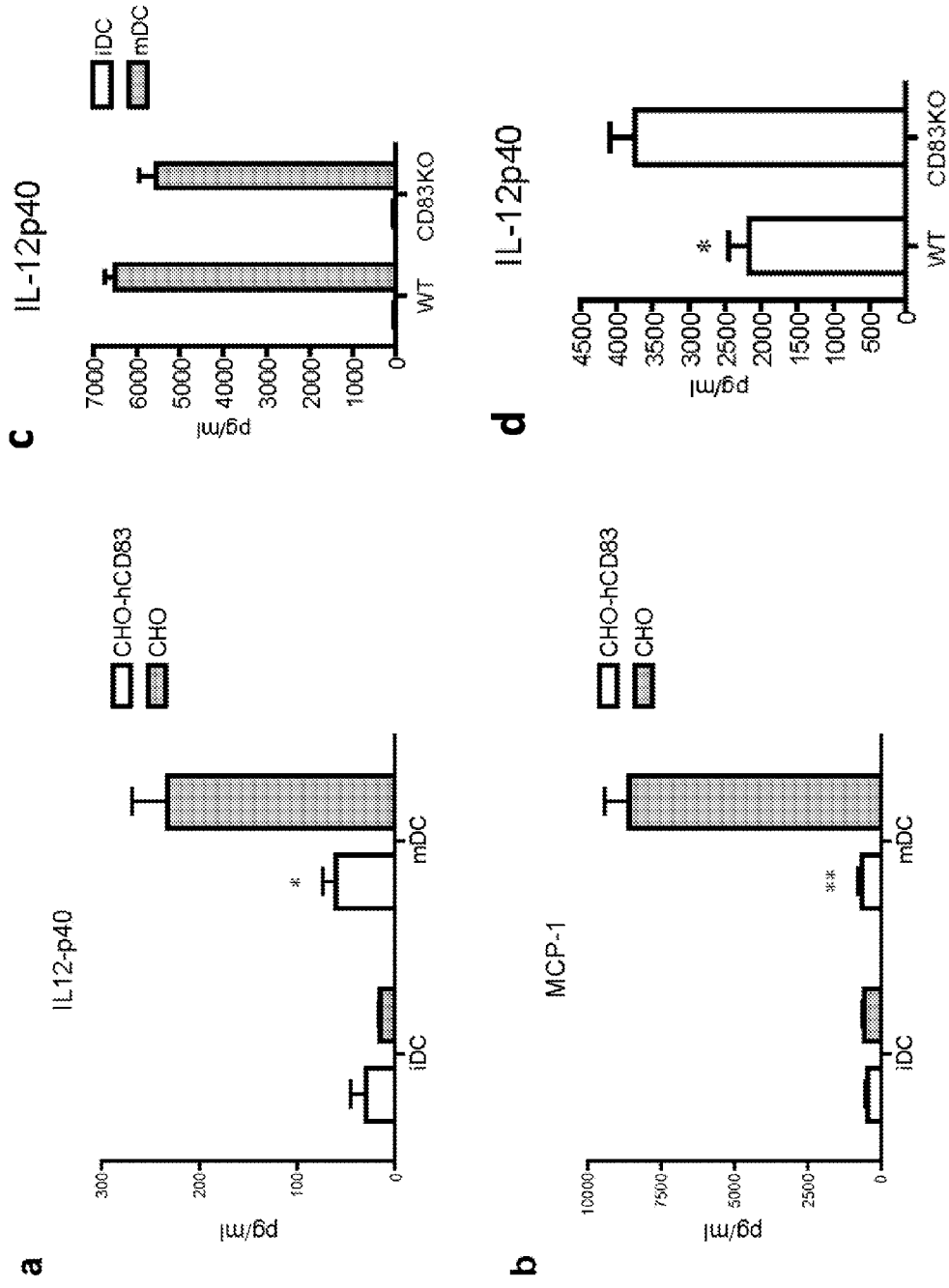
FIG. 8 demonstrates that CD83 homotypic interactions can occur in trans to mediate the anti-inflammatory response in DCs. (a and b) ELISA measurement of cytokine production showed that co-culturing of CHO cells overexpressing CD83 with mDCs inhibited the release of pro-inflammatory cytokines IL12-p40 and MCP-1. (c) Mature mouse bone marrow-derived DCs (BMDCs) (gray bars) generated from CD83 knock-out (CD83KO) and wild type (WT) littermates produced similar levels of IL-12p40 following 24 h LPS stimulation. (d) Immature BMDCs cultured with WT mature BMDCs produced significantly less IL-12p40 than those cultured with CD83 deficient mature BMDCs, p=0.0372.

To further characterize the CD83 interactions that modulate the anti-inflammatory response, DCs were monitored for an anti-inflammatory response when co-cultured with CHO cells overexpressing hCD83. To derive iDCs from MUTZ-3 cells, cells were cultured in MEMα+glutamax/20% heat-inactivated FBS containing 150 ng/ml rhGM-CSF and 50 ng/ml rhIL-4 for 6 days. The generated iDCs were co-cultured with either the control CHO cell line or with CHO cells stably expressing human CD83. The culture of mixed cells was subsequently either untreated or treated with a cytokine cocktail containing 25 ng/ml rhIL-1β, 100 ng/ml rhIL-6, 50 ng/ml rhTNFα and 1 µg/ml PGE-2 to produce mDCs. Cell culture supernatants were collected 48 hours after maturation of DCs and secreted cytokines IL12-p40 and MCP-1 were analyzed by ELISA (Invitrogen) according to standard manufacturer's instructions. Analysis of secreted IL12-p40 and MCP-1 levels showed that release of pro-inflammatory cytokines was significantly reduced in mDCs co-cultured with CHO cells expressing hCD83 as compared to CHO cells lacking CD83 expression (FIGS. 8A and B). This data demonstrates that CD83 can participate in trans homotypic interactions to mediate the anti-inflammatory response. These results were confirmed using human monocyte derived DCs (MDDCs) isolated from whole blood of multiple donors. Following stimulation, DCs cultured with CHO-hCD83 cells produced significantly less IL-12p40 than those cultured with the CHO cells lacking CD83 expression.

The co-culture of immature BMDCs with mature BMDCs from wild type or CD83 deficient animals was investigated and assayed for IL-12p40 production. CD83 knockout mice (CD83$^{-/-}$) were generated using a homologous recombination strategy similar to that used in Fujimoto, Y. et al., Cell 108, 755-767, 2002, which is incorporated herein by reference, that resulted in a loss of half of the immunoglobulin domain and the transmembrane and cytoplasmic domains of CD83. CD83$^{-/-}$ mice had a paucity of CD4 T cells but otherwise thrived, were produced at expected Mendelian frequencies, and reproduced as well as their wild type littermates. Upon stimulation with LPS, BMDCs generated from CD83$^{-/-}$ mice were able to upregulate the surface maturation marker CD86 and produce cytokines at similar levels to those generated from wild type littermates (FIG. 8C). Upregulation of MHCII was also seen upon stimulation with LPS, however BMDCs from CD83$^{-/-}$ mice expressed less MHCII than those generated from wild type mice. Next fresh immature BMDCs were co-cultured with mature cells from wild type or CD83$^{-/-}$ animals simultaneously with an LPS stimulus. Following 24 hrs, culture supernatants were collected and evaluated for IL-12p40 production by ELISA. Immature DCs co-cultured with mature DCs expressing high levels of CD83 produced significantly less IL-12p40 than those cultured with CD83 deficient mature DCs (FIG. 8D).

Figure 9:
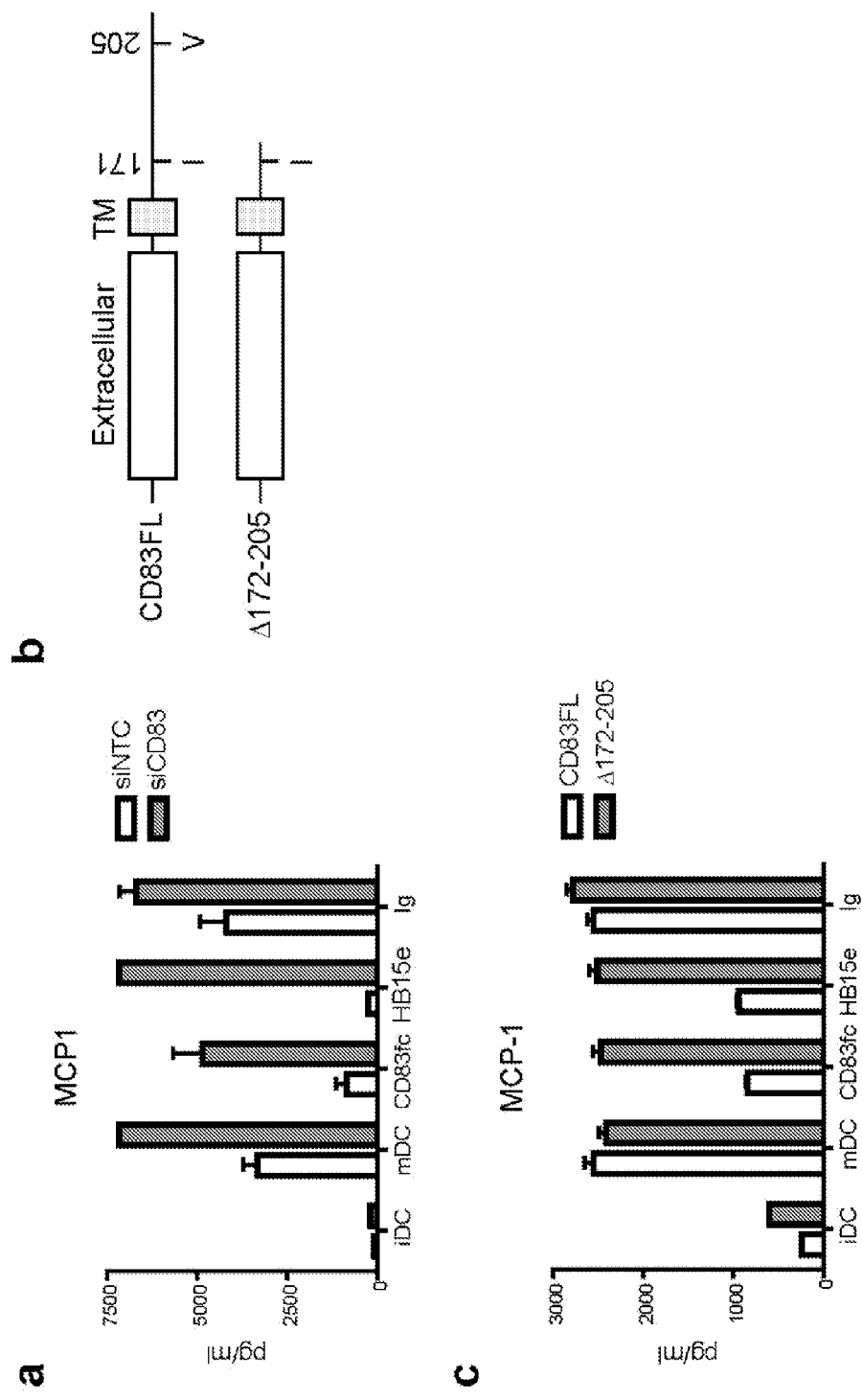
FIG. 9 demonstrates that CD83 homotypic interactions mediated the anti-inflammatory response in DCs. (a) siRNA knockdown of CD83 abrogated the response to CD83.fc or HB15e antibody as demonstrated by ELISA of MCP-1. (b) Diagram of CD83 lentiviral expression constructs for full length CD83 and cytoplasmic truncated CD83. (c) ELISA of MCP-1 production showed that expression of cytoplasmic truncated CD83 blocked the inhibitory effect of CD83.fc protein.

To verify that the anti-inflammatory response mediated by CD83 treatment required an interaction with cell surface CD83, treatment was assayed in DCs not expressing CD83. MUTZ-3 iDCs were transfected with Accell siRNA targeting CD83 (Cat. No. E-012680; Dharmacon) or non-targeting controls (Cat. No. D-001910; Dharmacon) four days after culture in MEMα+glutamax/20% heat-inactivated FBS containing 150 ng/ml rhGM-CSF and 50 ng/ml rhIL-4 MUTZ-3 iDCs were incubated for 72 hrs at 37° C. with 5% $CO_2$ in Accell delivery media (Cat. No. B-005000; Dharmacon) containing 10 uM siRNAs and supplemented with 3% heat-inactivated FBS, 150 ng/ml GM-CSF and 50 ng/ml IL-4. At day 7, iDCs were treated with a cytokine cocktail containing 25 ng/ml rhIL-1β, 100 ng/ml rhIL-6, 50 ng/ml rhTNFα and 1 µg/ml PGE-2 to produce mDCs. Treatment of mDCs with 10 µg/ml CD83.fc, 1 µg/ml HB15e, or control IgG.fc was given simultaneously with the maturation stimulus. Cell culture supernatants were collected 48 hours after maturation of DCs and secreted cytokines were analyzed by ELISA using an MCP-1 kit (Invitrogen) according to standard manufacturer's instructions. Analysis of MCP-1 released by mDCs indicates that siRNA knockdown of CD83 (siCD83) abrogates the response to CD83.fc and HB15e antibody (FIG. 9A). Therefore, this data shows that CD83 is required on the cell surface to mediate the anti-inflammatory response by CD83 treatment. These results were confirmed by detection of secreted IL-12p40. Analysis of IL-12p40 released by mDCs indicated that siRNA knockdown of CD83 (siCD83) abrogated the response to CD83.fc and HB15e antibody.

To determine if the anti-inflammatory response during CD83 treatment requires homotypic binding and downstream signaling through cell surface CD83, treatment was assayed in DCs expressing a cytoplasmic truncated CD83 construct. CD83 lentiviral expression constructs were derived from pGCMV.IRES.eGFP (pGIPZ derivative; Openbiosystems) and were made by PCR amplifying the full-length hCD83 gene (CD83FL) or amplifying a segment of the hCD83 gene which truncates the cytoplasmic region (0172-205) and inserting these fragments into the XhoI/EcoRI cloning sites (FIG. 9B). To generate the lentivirus for infection of DCs, 293T cells were seeded at 1×10$^7$ on gelatinized 10 cm culture dishes and allowed to grow for ~20 h to reach 80-90% confluency. Media was replenished with 5 ml DMEM, 10% FBS, 2 mM L-glutamine and cells were transfected with a DNA mix containing 5 µg expression plasmid, delta 8.9 and VSVG at a molar ratio of 1:2.3:0.2., using Lipofectamine 2000 (Invitrogen) for 6 h at 37° C. Transfection media was replenished with 6 ml normal growth media and cells were incubated an additional 40 hours at 37° C. Supernatants were harvested, cleared by filtering through a 0.45 µm tube top filter (Corning), and concentrated using Lenti-X-concentrator (Clonetech) according to manufacturer's instructions. MUTZ-3 cells were seeded at 0.5×10$^6$/ml in 24-well culture plates in maintenance media containing MEMα+Glutamax/20% heat-inactivated FBS/15% HTB-9 conditioned media. Polybrene and concentrated lentiviral supernatant was added to the cells at a final concentration of 4 µg/ml and an MOI of 10, respectively. Cells were spun at 1800 rpm in an Allegra X-12R tabletop centrifuge for 30 minutes at room temperature then incubated overnight at 37° C. Media containing lentivirus was removed and replaces with fresh maintenance media. After 2-3 days culture, the top 10% of GFP positive cells were sorted and cultured in MEMα+Glutamax/20% heat-inactivated FBS supplemented with 150 ng/ml rhGM-CSF and 50 ng/ml rhIL-4 for 6 days and used as iDC. Cells were treated with a maturation stimulus as well as treated with CD83.Fc, HB15e or isotype control for 48 hours. Supernatants were subsequently collected and MCP-1 release was analyzed by ELISA. Analysis of secreted MCP-1 demonstrated that lentiviral over-expression of full-length CD83 did not inhibit mDC response to CD83.fc or HB15e, however expression of the cytoplasmic truncated CD83 blocked the anti-inflammatory effect of CD83 treatment (FIG. 9C). These results were confirmed by detection of secreted IL-12p40 Analysis of secreted Il-12p40 demonstrated that lentiviral over-expression of full-length CD83 did not inhibit mDC response to CD83.fc or HB15e, however expression of the cytoplasmic truncated CD83 blocked the anti-inflammatory effect of CD83 treatment.

Figure 10:
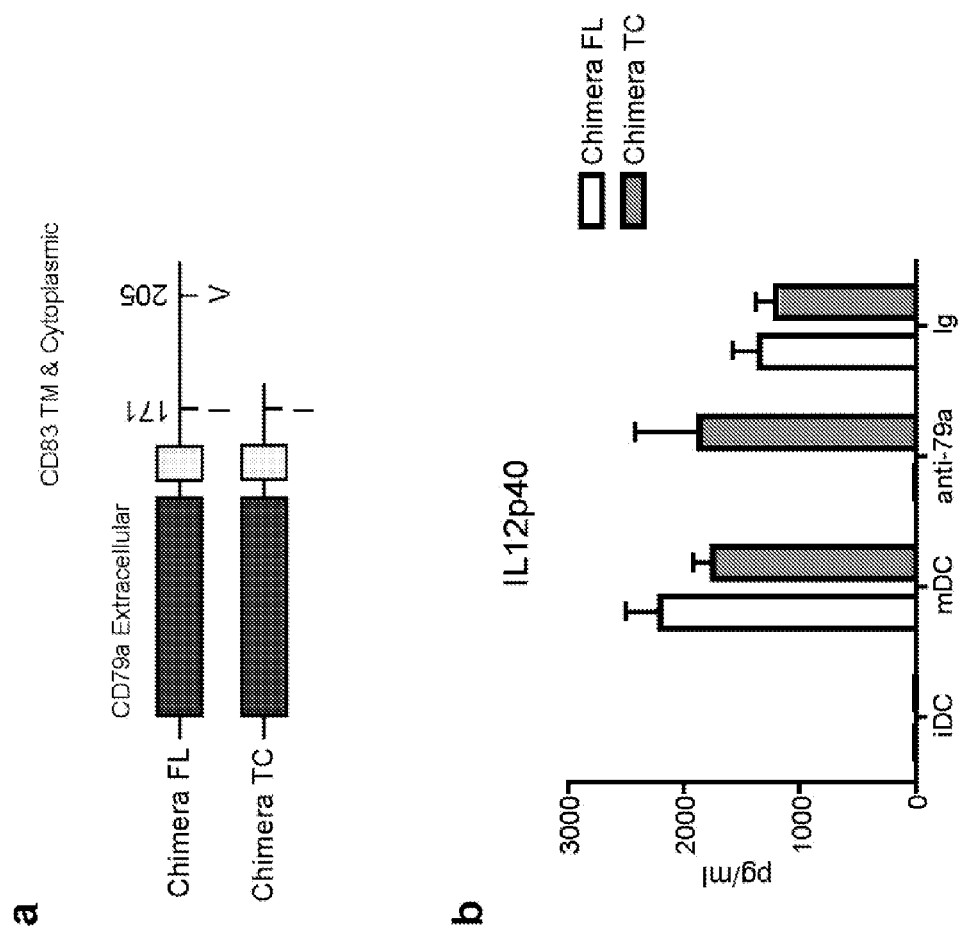
FIG. 10 demonstrates that antibody cross-linking was sufficient to drive an anti-inflammatory response through the CD83 cytoplasmic domain in DCs. (a) Diagram of CD83 chimeric lentiviral expression constructs depicting the extra-cellular domain of CD79a fused to the CD83 transmembrane and full length or truncated cytoplasmic domain. (b) ELISA of IL12-p40 production showed that overexpression of truncated chimera inhibited the DC response to anti-CD79a antibody.

To determine is cross-linking alone is sufficient to drive an anti-inflammatory response through the CD83 cytoplasmic domain, a CD83 chimeric lentiviral expression construct was generated that contained the extracellular region of CD79a fused to the CD83 transmembrane and the full-length or truncated cytoplasmic domain (FIG. 10A). iDCs were infected with the indicated lentiviral constructs as described above and subsequently treated with a maturation stimulus and with 1 µg CD79a antibody (Santa Cruz) or isotype control for 48 hours. Supernatants were collected and IL12-p40 release was analyzed by ELISA. Analysis of secreted IL12-p40 demonstrated that lentiviral overexpression of the full-length CD83 chimera did not inhibit the mDC response to anti-CD79a antibody, however expression of the cytoplasmic truncated CD83 chimera blocked the anti-inflammatory effect of treatment with anti-CD79a (FIG. 10B). Overall, these results demonstrate the novel finding that CD83 homotypic interactions mediate the anti-inflammatory effect due to CD83 treatment.

Example 5

Figure 11:
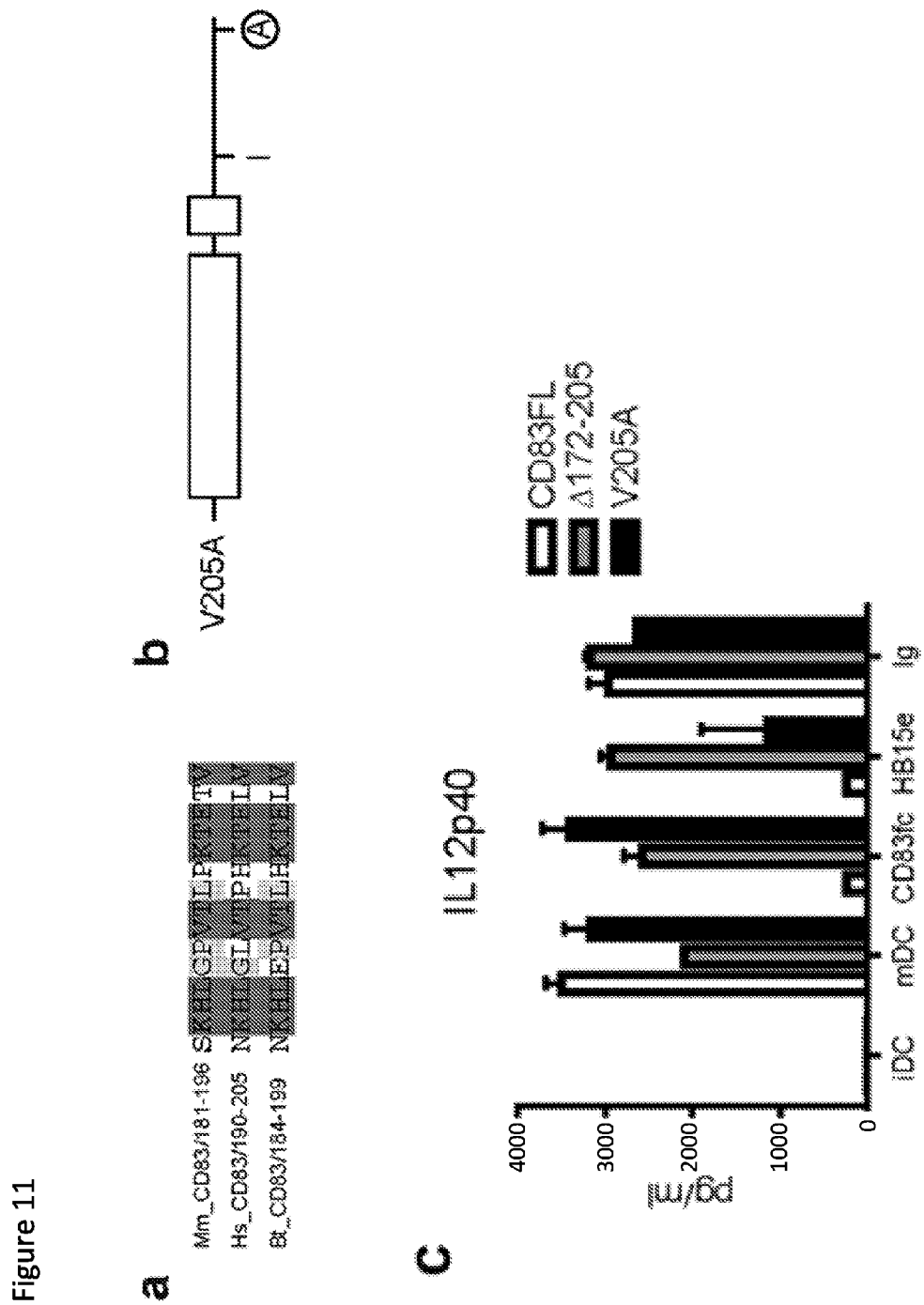
FIG. 11 shows that CD83 contains a class III PDZ ligand motif at the C-terminus that mediates the anti-inflammatory response. (a) Amino acid alignment diagram of the last 15 amino acids of CD83 cytoplasmic domains showed a conserved class III PDZ ligand motif (b) Diagram of a CD83 lentiviral expression construct of the C-terminal PDZ ligand motif V205A mutant. (c) ELISA of MCP-1 production showed that expression of the V205A PDZ ligand motif mutant blocked the inhibitory effect of CD83.fc protein.

CD83 Homotypic Interactions Inhibit Inflammation Through Repression of the MAPK and mTOR Signaling Pathways Due to the novel finding that CD83 homotypic interactions elicits anti-inflammatory effects in DCs, the downstream signaling pathways regulated by the CD83 cytoplasmic domain were investigated. Alignment of the last 15 amino acids of CD83 cytoplasmic domains indicates that a C-terminal class III PDZ ligand motif is conserved in CD83 (FIG. 11A). To determine if this motif mediates the anti-inflammatory response during CD83 treatment, a CD83 lentiviral expression construct was generated that contained full length CD83 with a valine to alanine mutation at position 205 (V205A) in order to abolish the class III PDZ ligand motif (FIG. 11B). iDCs were infected with the indicated lentiviral constructs as described above. Cells were treated with a maturation stimulus as well as treated with CD83.Fc, HB15e or isotype control for 48 hours. Supernatants were subsequently collected and IL12-p40 release was analyzed by ELISA. Analysis of secreted IL12-p40 demonstrated that lentiviral overexpression of full-length CD83 did not inhibit the mDC response to CD83.fc or HB15e, however expression of the CD83 V205A mutant blocked the anti-inflammatory effect of CD83 treatment (FIG. 11C). These results suggest that the class III PDZ ligand motif on the CD83 cytoplasmic domain interacts with proteins that mediate the anti-inflammatory response.

Figure 12:
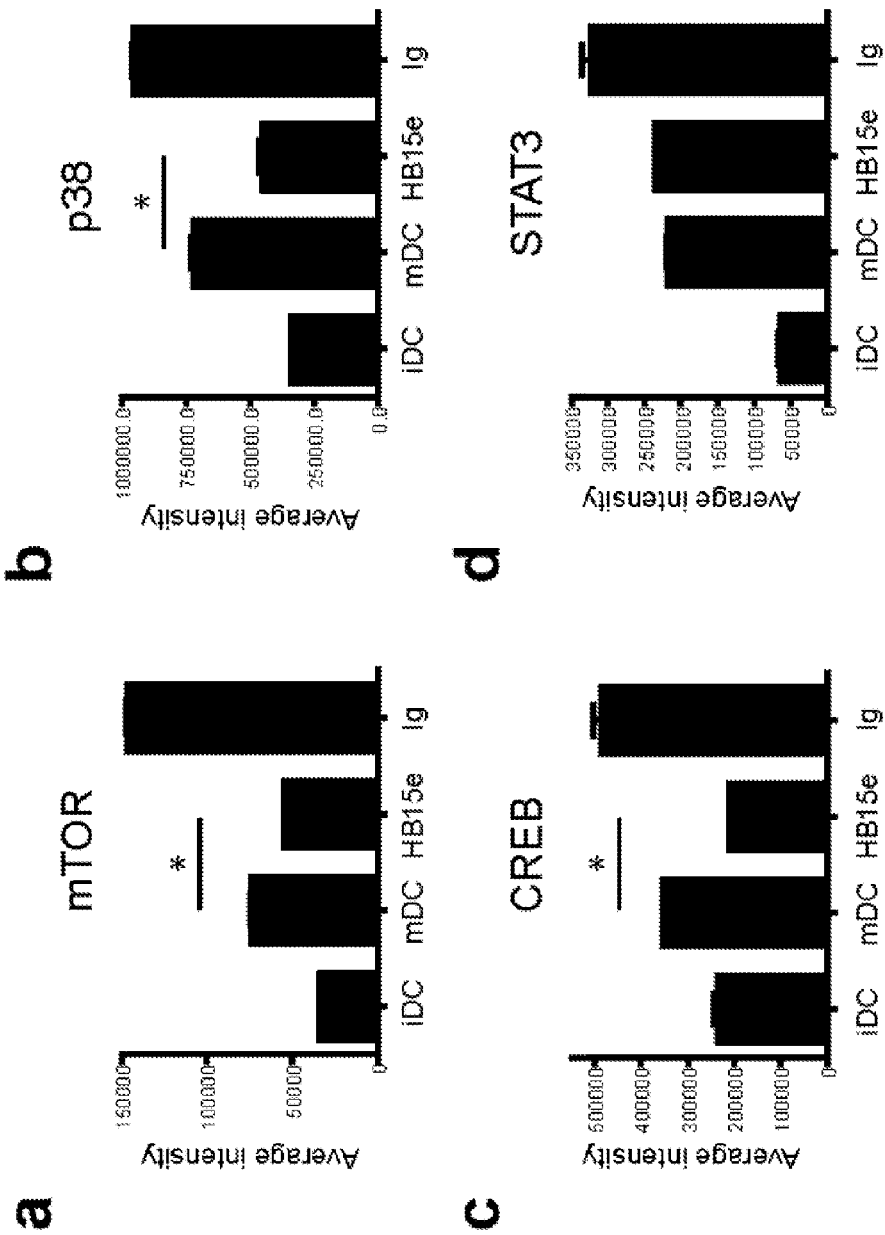
FIG. 12 shows that the immunosuppressive effects of CD83 homotypic interaction were mediated by p38 MAPK and mTOR signaling pathways. (a-c) showed that HB15e antibody treatment resulted in a significant decrease in phosphorylation of mTOR, p38 and CREB. (d) HB15e antibody treatment did not inhibit phosphorylation of STAT3 which is activated by the TNF pathway. (e) Western blot analysis confirmed decrease in p38 phosphorylation upon HB15e antibody treatment. (f) No significant difference seen in phosphorylation of STAT3 upon HB15e antibody treatment. Total p38 and STAT3 were used as loading controls.
Figure 12:
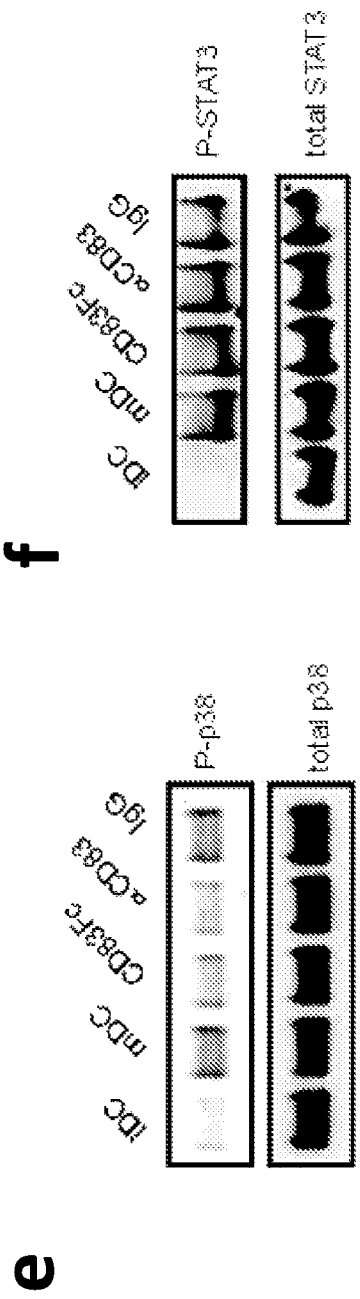

To determine if the immunosuppressive effects of CD83 homotypic interactions were mediated by additional signaling pathways, phospho-kinase arrays were conducted on cell lysates from mDCs treated with CD83.fc or HB15e for 5 minutes. Human phospho-kinase arrays (R&D systems) were performed according to the manufacturer's instructions. Briefly, MUTZ-3 DCs were washed with cold PBS and solubilized in Lysis Buffer 6 and rocked at 4° C. for 30 minutes. Lysates were centrifuged at 14,000×g for 5 minutes and the supernatant was transferred to a new tube for analysis of total protein by Bradford (Bio-Rad). Array membranes containing 46 antibodies spotted in duplicates were blocked for 1 hour at room temperature then incubated with diluted cell-lysate overnight at 4° C. Membranes were washed and then incubated with detection antibodies for 2 hours at room temperature. Following washing, membranes were incubated in Streptavidin-HRP for 30 min at room temperature and washed again prior to detection with ECL Plus reagents (Amersham). Membranes were exposed on FUJI FILM Image Reader LAS-3000 and the average intensity was analyzed by Multi Gauge v3.1 (FUJI FILM). HB15e treatment resulted in a significant decrease in phosphorylation of mTOR, $p=0.046$ (FIG. 12A), p38, $p=0.008$ (FIG. 12B) as well as CREB, $p=0.0104$ (FIG. 12C). In contrast, HB15e antibody treatment did not inhibit phosphorylation of STAT3 which is activated by TNF receptor binding of TNFα, a component in the maturation stimulus (FIG. 12D). Western blot analysis of whole cell lystates from human monocyte-derived DCs (MDDCs) treated with CD83.Fc or αCD83 (HB15e) confirmed a decrease in phospho-p38 MAPK (FIG. 12E) with no significant effect on STAT3 phosphorylation (FIG. 12F). These novel findings indicate that the anti-inflammatory effect of CD83 homotypic interactions was mediated by p38 MAPK as well as mTOR protein signaling.

Example 6

Figure 13:
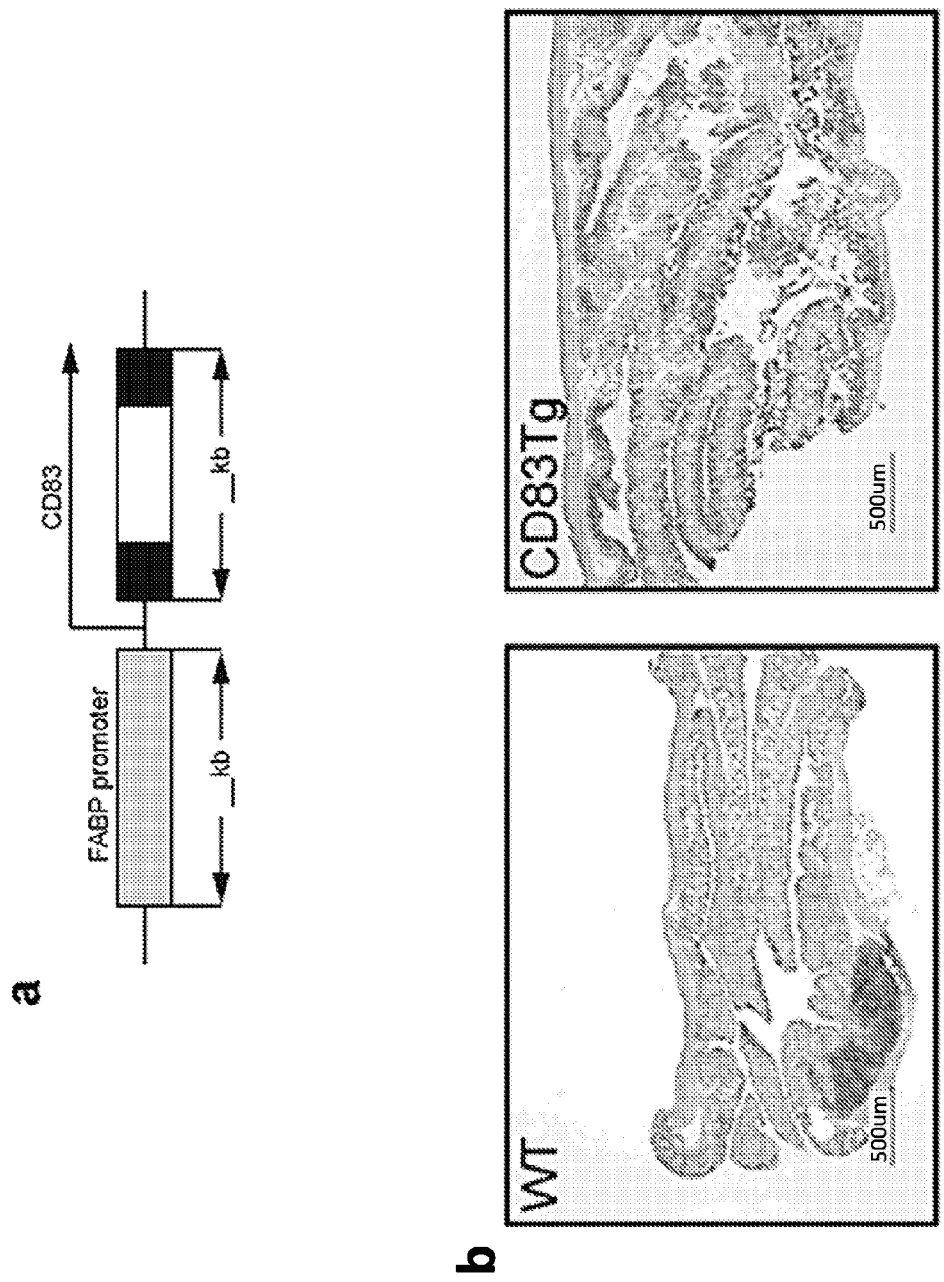
FIG. 13 shows that CD83 overexpression in the colon resulted in downregulation of surface activation markers on DCs in the lamina propia. (a) Diagram of the transgenic construct used to generate the CD83 transgenic mice. (b) Immunohistochemistry staining showed expression of the transgene in the colon epithelia. (c and e) Expression of surface markers on DCs isolated from the colon and spleen of CD83 transgenic mice were quantified by FACS and measured as mean fluorescence intensity (MFI). (d and f) No significant difference in T cell surface activation markers was found in either the colon or spleen of CD83 transgenic mice. (g) Taqman qPCR analysis showed increased wound healing gene expression in DCs isolated from CD83 transgenic mice.
Figure 13:
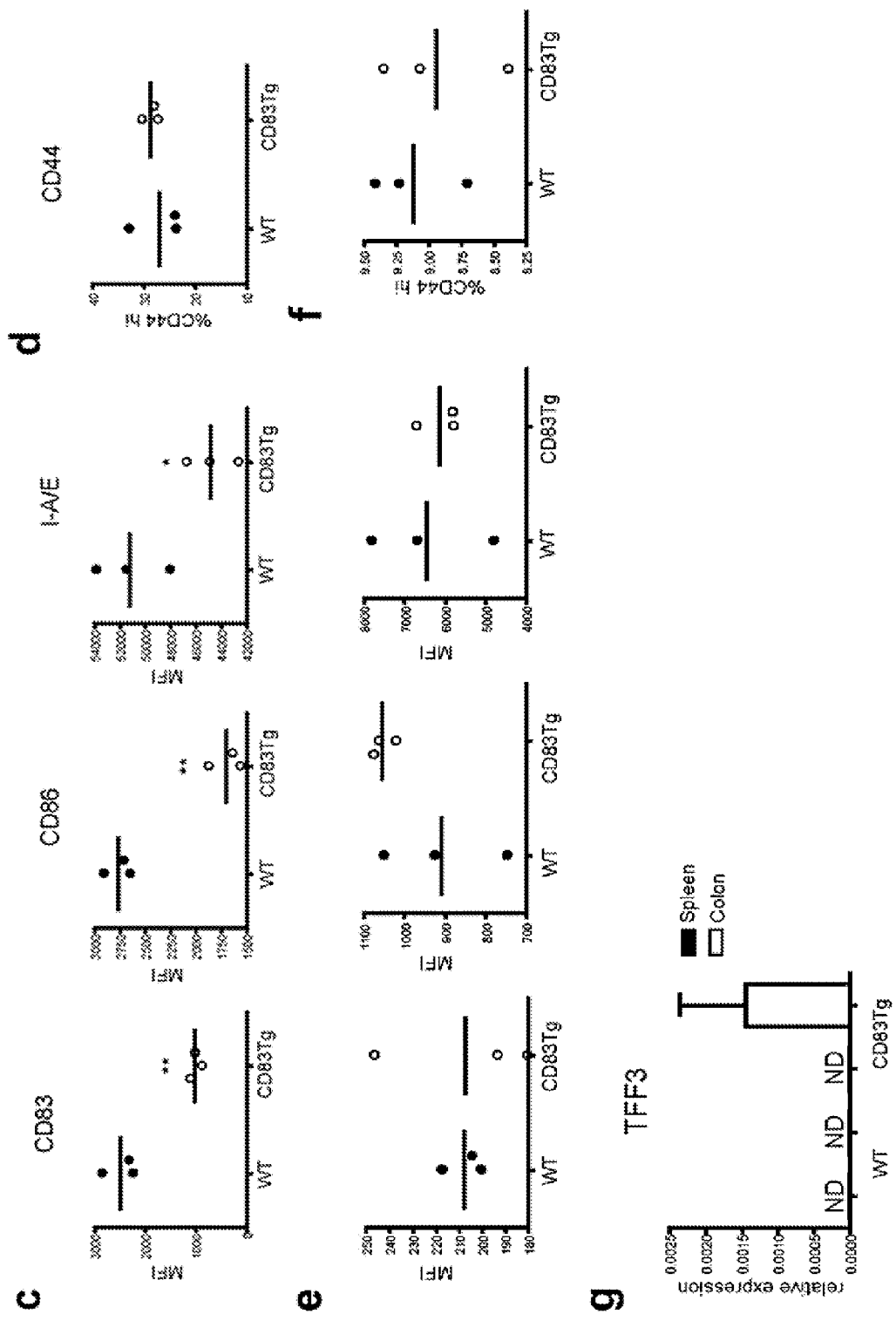

CD83 Overexpression Results in Decreased Expression of Surface Activation Markers on Colon Lamina Propia DCs The novel finding that CD83 homotypic interactions elicit anti-inflammatory effects in DCs in vitro suggests that it may elicit a similar effect in vivo. To investigate the effects of CD83-mediated immunosuppression in vivo, a transgenic mouse line overexpressing CD83 (CD83Tg) at the mucosal surface was generated. To generate the FABP.CD83 targeting vector the Picomax PCR system was used to amplify the full-length mouse CD83 (mCD83) from colon tissue for cloning into the FABP.sup.LacZ vector using the SpeI/SacII sites (FIG. 13A). The primers used for PCR were CD83SPE-Forward primer: 5'-GATCAAACTAGTCCACCATGTCG-CAAGGCCTCCAGCTCCT-3' (SEQ ID NO:40) and CD83SACII-Reverse primer: 5'-CATCATCCGCGGTCAT-ACCGTTTCTGTCTTAGGAAG-3' (SEQ ID NO:41). Following microinjection, 72 founder mice were screened for high expression in the colon and low expression in the kidney. 1 mouse met these criteria and was used to generate the transgenic line by backcrossing to FVB mice (Jackson Labs). Mice were housed in a specific pathogen-free barrier facility. All procedures were approved by the Genentech Animal Care and Use Committee.

Immunohistochemistry staining of the colon for CD83 showed expression of CD83 in wild-type animals was limited to gut-associated lymphoid tissue, but CD83Tg overexpress CD83 in the colon epithelium (FIG. 13B). To determine if CD83 overexpression had an effect on DC subsets, T cell populations and surface markers, colons were harvested and flushed with cold HBSS/2% FBS/10 mM HEPES. Fat and other tissue associated with colon was removed and colons were rinsed with HBSS/2% FBS. Colons were cut longitudinally with scissors and transferred to a 50-ml conical with 30-40 ml HBSS/2% FBS on ice. Colon pieces were then transferred to a sterile baffled flask (Corning) with 10-15 ml pre-warmed HBSS/2% FBS/10 mM HEPES/1 mM EDTA. Flasks were shaken at 200 rpm for 45 minutes at 37° C. Media was poured off and colons were washed in fresh HBSS/2% FBS/10 mM HEPES and remaining epithelia were scraped off using a blade. Colon was diced into 1-2-mm pieces in RPMI containing 10% FCS, 20 mM HEPES, 0.5 mg/ml collagenase/dispase, penicillin, and streptomycin, then incubated for 45-90 min at 37° C., with shaking at 200 rpm. The suspension was pipetted 4-5 times and filtered through a 100 µm filter, followed by 1800 rpm spin for 10 min at 4° C. Cells were washed with RPMI containing 5% FBS, 20 mM HEPES, and 0.1 mg/ml DNAse and filtered through a 70 µm filter. Cells were then washed with FACS buffer and stained with antibodies for analysis of immune cells as well as sorting of DCs for RNA isolation and qPCR.

Figure 14:
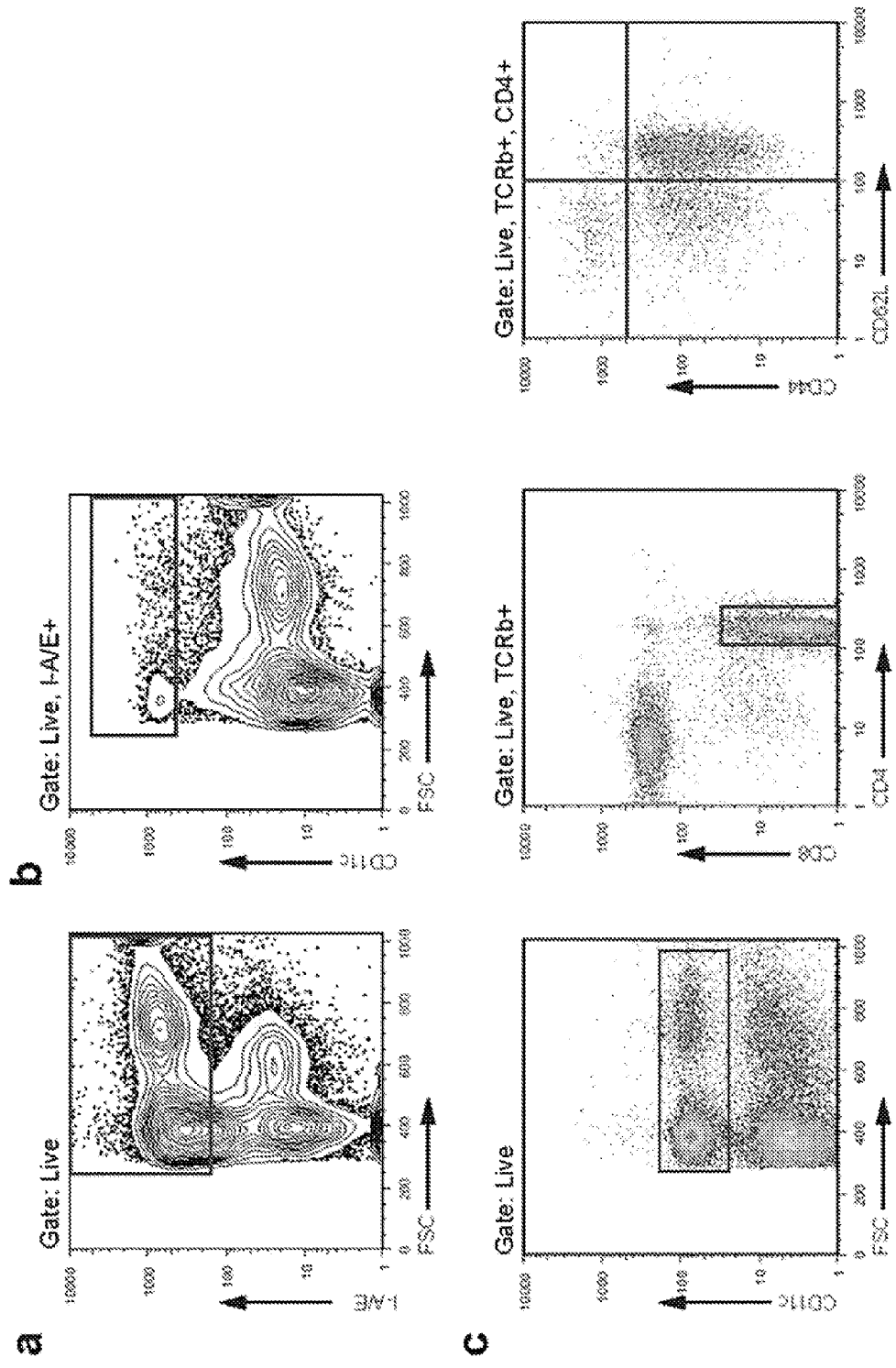
FIG. 14 depicts the FACS gating strategy for analyzing DC subsets isolated from the CD83 transgenic mice, which demonstrated that the CD83 transgene had no effect on DC subset production. (a and b) DCs gated by MHCII+ and CD11c hi expression. (c) Gating of T-cells. (d and e) flow cytometry analysis of DC subsets isolated from the colon and spleen.
Figure 14:
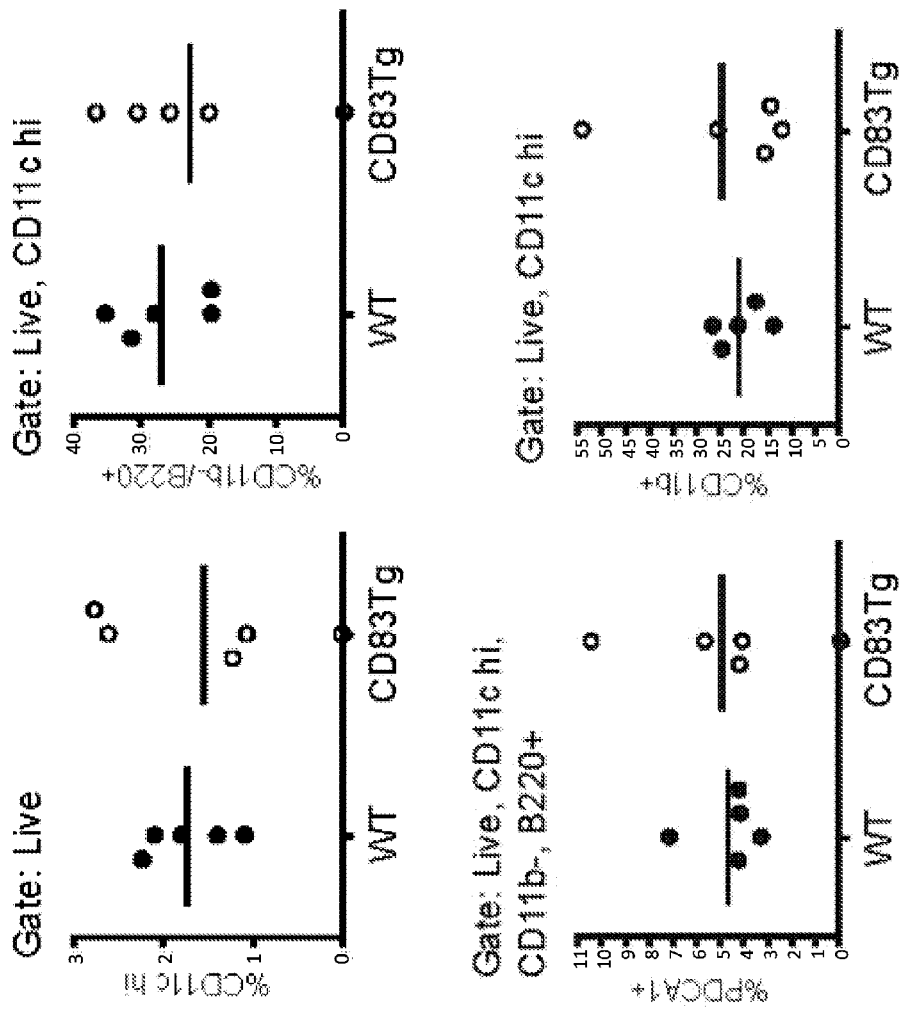
Figure 14:
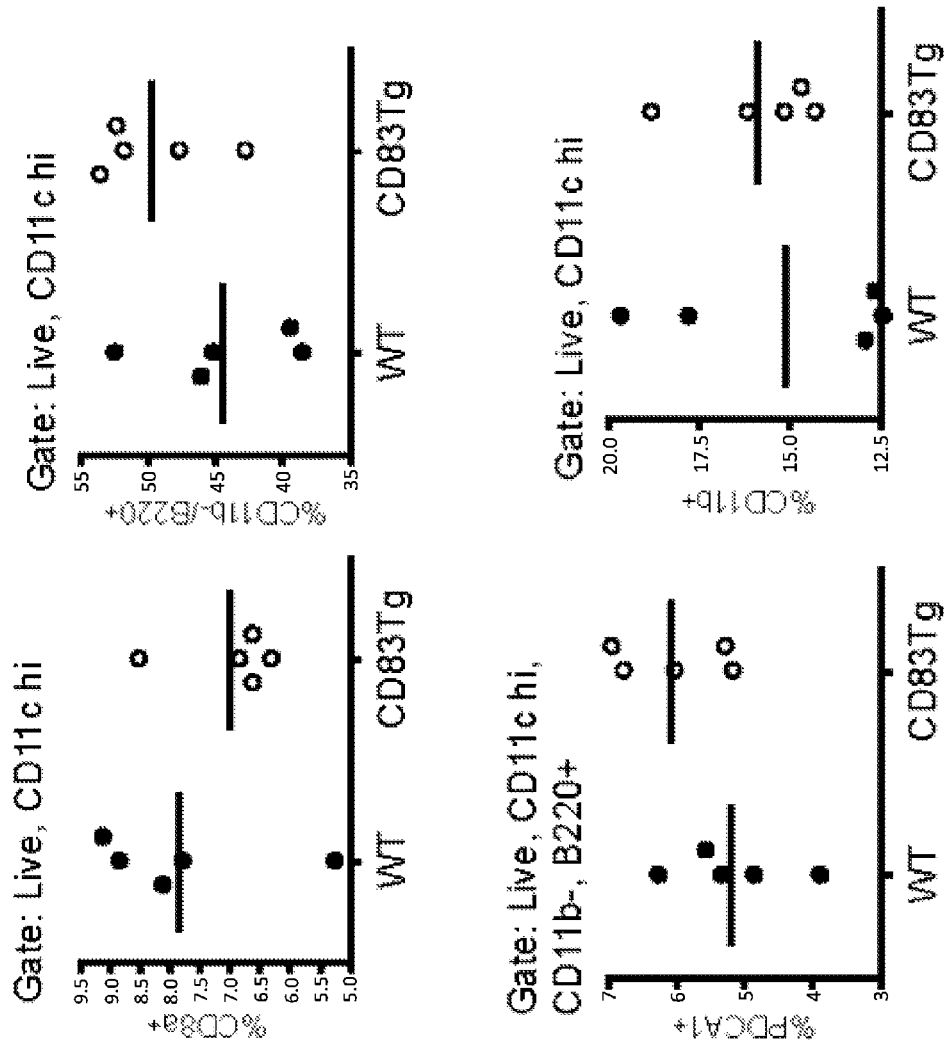

DCs isolated from the colon lamina propia or spleen of the CD83Tg mice were sorted by flow cytometry for MHCII and CD11c hi expression (FIGS. 14A and B) Analysis of DC subsets indicated no significant difference in numbers or percentages of plasmacytoid (CD11b−/B220+), myeloid (CD11b+), or lymphoid (CD11 b−/B220−/CD8a+) DCs isolated from the colon (FIG. 14D) or spleen (FIG. 14E) indicating that CD83 overexpression had no effect on DC subsets within the CD83Tg mice. Analysis of DC surface activation markers CD83, CD86, and MHCII (I-A/E) demonstrated that they were significantly decreased on the surface of DCs isolated from the colon *p<0.05, **p<0.01 (FIG. 13C), while those from the spleen showed no significant difference (FIG. 13E). Each dot represents cells pooled from three animals. Furthermore, analysis of T cells isolated and sorted from the colon lamina propia or spleen of the CD83Tg mice (FIG. 14C), indicated no significant difference in expression of the CD44 surface marker indicative of T cell activation whether isolated from colon (FIG. 13D) or spleen (FIG. 13F). Interestingly, taqman qPCR analysis of total RNA isolated from CD83Tg DCs showed increased wound healing gene expression in the colon but was not detectable (ND) in the colon of wild-type mice (FIG. 13G). Data is representative of three independent experiments, n=6 for each group. Overall, these in vivo results are supported by the in vitro results observed with CD83.fc or HB15e treatment of DCs.

Example 7

CD83 Immunosuppression Protects Mice from DSS Induced Colitis

Figure 15:
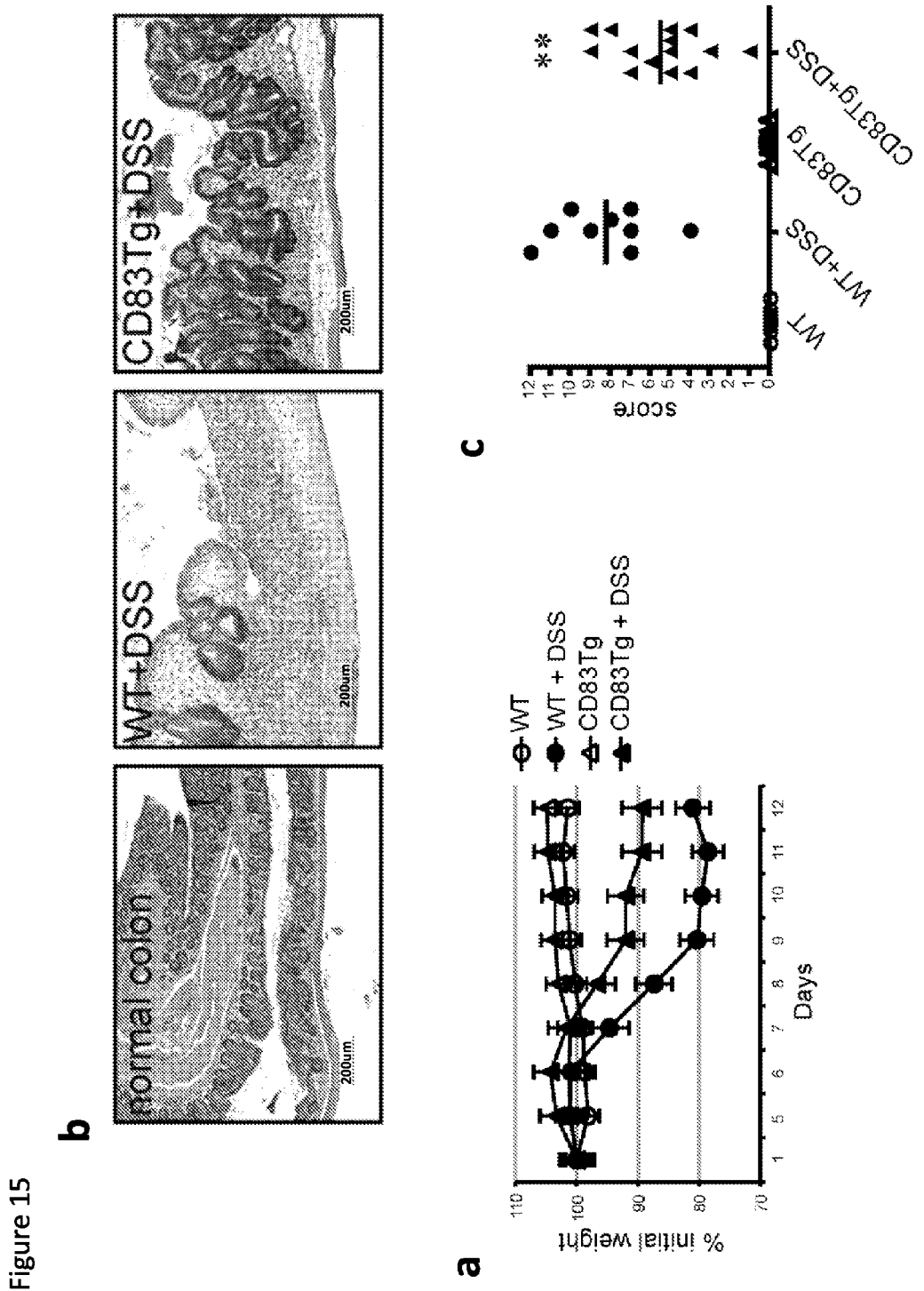
FIG. 15 shows that CD83 overexpression protected mice from dextran sodium sulfate (DSS) induced colitis. (a) depicts less weight loss in CD83 transgenic mice as compared to wild-type mice when treated with DSS. (b) Hematoxylin and eosin staining of colon section of mice with DSS induced colitis. (c) Histology scores of wild-type and CD83 transgenic mice. (d) ELISA of serum cytokine levels in CD83 transgenic mice treated with DSS as compared to wild-type littermates. (e) qPCR for IL-12p40 gene expression in colon lamina propia DCs from CD83Tg mice treated with DSS as compared to wild-type littermates.
Figure 15:
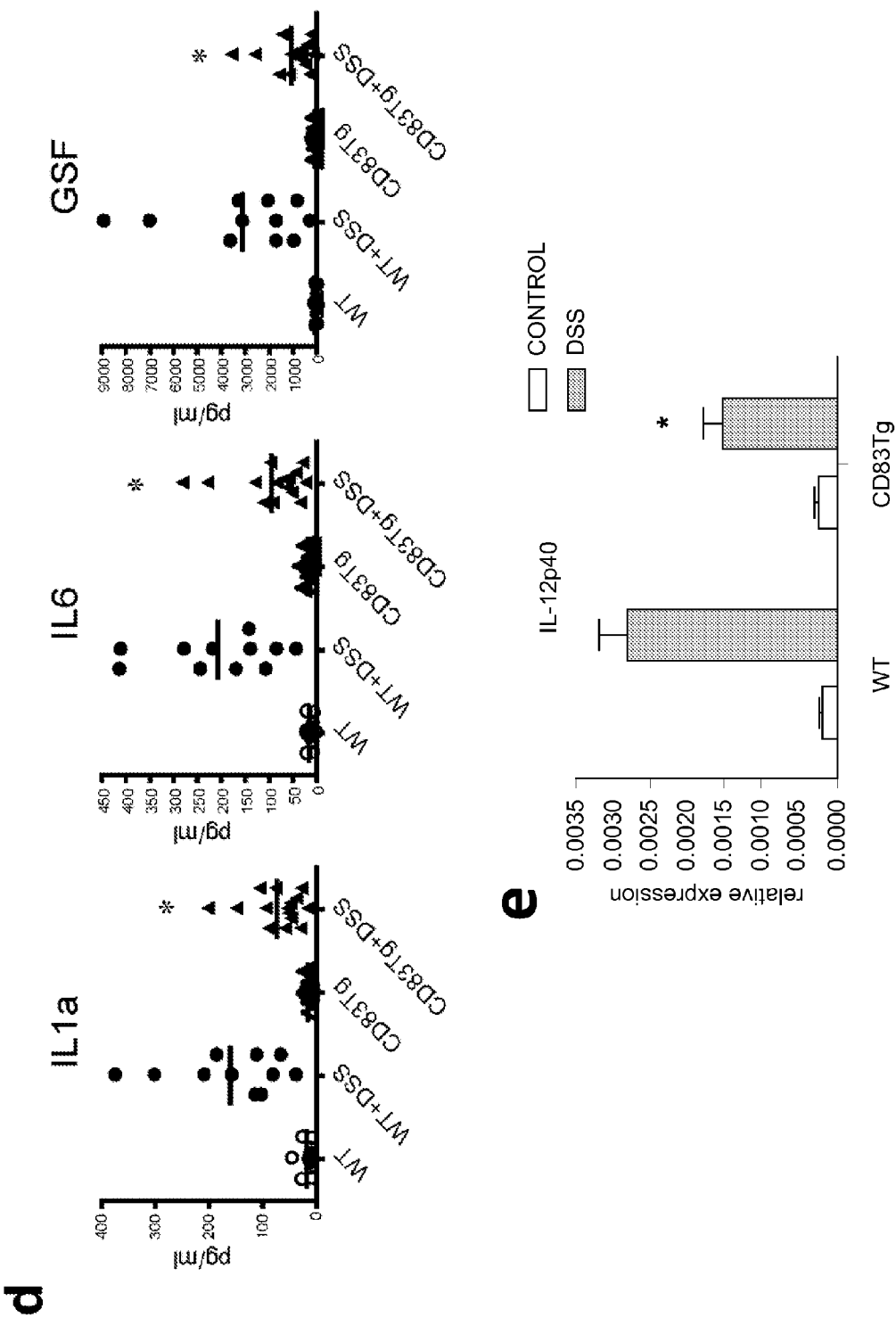

To assess the effect of CD83 overexpression in a mouse model of inflammatory bowel disease, colitis was induced in the CD83Tg mouse line, generated and characterized in the previous example, by treatment with dextran sodium sulfate (DSS). CD83Tg mice at 8-10 weeks of age were given 6% DSS ad libitum in drinking water for 7 days, and at day 7 were switched to normal drinking water until cessation of experiment on day 12. Mice were weighed on day 0 and daily from day 4 onwards, and checked for occult blood, diarrhea, and any other abnormal signs. If weight loss exceeded 20% initial weight on day 0, mice were euthanized. At day 12 mice were bled orbitally under anesthesia to collect 150-200 µl blood, which generated ~150 µl sera. Sera cytokines were evaluated using the Bio-Plex Pro Mouse 23-Plex assay (Cat. No. M60-009RDPD; Bio-Rad) according to manufacturer's instructions. Mice were then euthanized and the small and large intestine was sectioned and stained with H&E for histology analysis. Sections were randomized and scored double-blind. Wild-type mice treated with 6% DSS lost ~20% body weight, while CD83Tg mice retained ~89% initial body weight by day 12 (FIG. 15A). Wild type mice had severe colitis marked by loss of colon architecture and increased inflammatory infiltrates as compared to CD83Tg mice (FIG. 15B). Histology scores of H&E staining of colon sections from wild type and CD83Tg mice demonstrate that wild-type mice had a mean histology score of 8.2, while the histology score of CD83Tg mice was significantly lower (**, P=0.0094) at 5.3 (FIGS. 15B and C). Additionally, serum levels of pro-inflammatory cytokines were measured by ELISA and were found to be significantly decreased in CD83Tg mice treated with 6% DSS as compared to wild-type littermates (*, P<0.05) (FIG. 15D). These results demonstrate that mice overexpressing CD83 at the mucosal surface are more resistant to colitis, leading to weight retention and decreased serum cytokine levels. Thus, a CD83 homotypic interaction regulates the DC-mediated immune response, preventing inappropriate inflammation and promoting tolerance.

To determine if the protection seen during DSS colitis in mice overexpressing CD83 was due to an effect of CD83 on the underlying lamina propria DCs, IL-12p40 expression was assayed in lamina propria DCs from CD83Tg and WT mice undergoing DSS colitis. Following DSS treatment for 7 days, mice were euthanized on day 9, when weight loss was significantly different between CD83Tg and WT siblings. DCs were then sorted from the isolated lamina propria immune cells to evaluate expression of proinflammatory cytokines by qPCR. DSS induced expression of inflammatory cytokines in both CD83Tg and WT mice. However, DCs isolated from CD83Tg mice had significantly decreased IL-12p40 expression compared to wild-type littermates (*, p=0.0315) (FIG. 15E), indicating that increased mucosal CD83 levels modulate the DC immune response to protect during colitis.

Example 8

Loss of CD83 in Dendritic Cells Exacerbates Colitis

Figure 16:
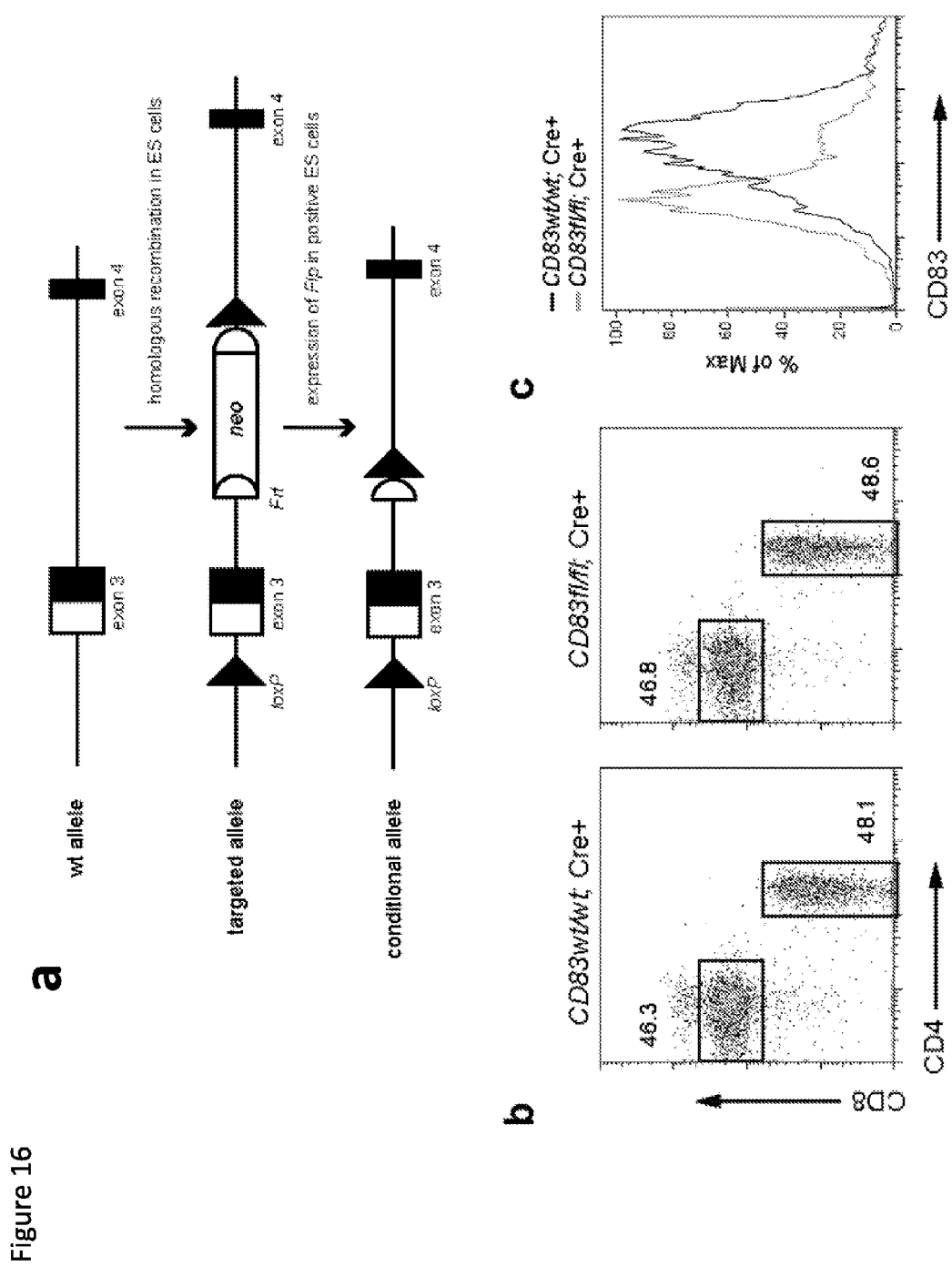
FIG. 16 shows that knock-out of CD83 in DCs exacerbated colitis. (a) Diagram of CD83 conditional knock-out strategy. (b) FACS plots gated on TCRb+ lymphocytes in spleen. $CD83^{fl/fl}$ CD11c-Cre mice had 48.6% CD4 positive T cells, $CD83^{wt/wt}$ CD11c-Cre mice had 48.1% CD4 positive T cells in spleen. (c) Histogram showing relative expression of CD83 on splenic DCs of $CD83^{wt/wt}$ CD11c-Cre (black line) and $CD83^{fl/fl}$ CD11c-Cre (gray line) mice. (d) DSS colitis survival in $CD83^{fl/fl}$ CD11c-Cre and $CD83^{wt/wt}$ CD11c-Cre mice. Conditional knock-out animals had significantly decreased survival (Log rank test, p=0.0186). (e) Body weight at day 8 was significantly lower in $CD83^{fl/fl}$ CD11c-Cre mice compared to $CD83^{wt/wt}$ CD11c-Cre littermates. (f) Incidence of frank blood surrounding anus of animals. 100% of $CD83^{fl/fl}$ CD11c-Cre mice had overt occult blood by day 7. Frank blood was not observed in $CD83^{wt/wt}$ CD11c-Cre littermates.
Figure 16:
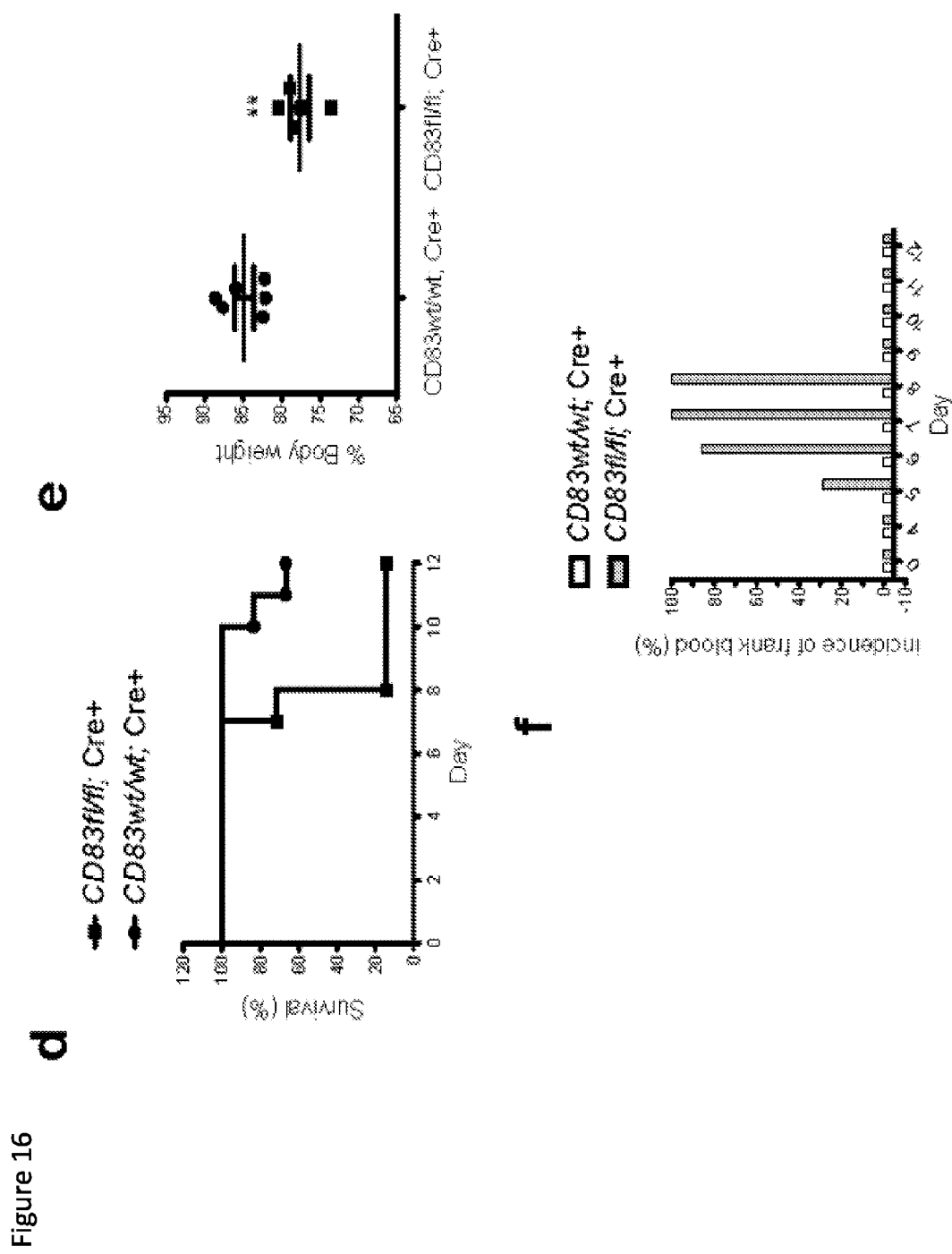

To determine if the loss of CD83 in DCs would exacerbate colitis, mice that specifically lacked CD83 expression in DCs were generated and assayed. CD83$^{fl/fl}$ mice were generated by homologous recombination. First a CD83 genomic fragment was retrieved from a BAC (Cat. No. RPCI23.C, Invitrogen) using a synthesized CD83 retrieval vector with unique restriction sites (SEQ ID NO:42): GCGGCCGC-GAGCAACTGATATTATATATGCCTTGAACATGAAAC-CAGGGGCAGGCTGT GGAATATTTCCAGGCACGCT-GTCTCGAGGCACAGTAGATCCTCAACCCAAGTGGA-TAA GAGATGACAATAGCTTTCCAAGAGAGACAGT-TATGAGGGACC (Blue Heron). The purified retrieved fragment was co-transformed with the first targeting cassette (SEQ ID NO:43): ACAGGTCTCCCAGCCAGT-GTTTCTCTCACCCCTGCAGGGTGAAGGCTGTGTTG-GTTCCT GGTGCTACAATCACAGCATTGCAGTCT-TATCTTGTTTCAAAATAACTTCGTATAATGTA TGCTATACGAAGTTATCTGTTGACAATTAATCATCG-
GCATAGTATATCGGCATAGTAT AATACGACAAGGT-
GAGGAACTAAACCCTTCCTCGTGCTTTACGG-
TATCGCCGCTCCCG
ATTCGCAGCGCATCGCCTTCTATCGCCTTCTTGAC-
GAGTTCTTCTGAATAACTTCGTAT AATGTATGC-
TATACGAAGTTATGCAAACACAGTCT-
CAAGAGTTTTTATAGATTCTCTTC
TTCTCCCCTGGAATCCTCATTTACAGGGA-
TAGGGGGTGGGGGAGCACCCTGTCTTGCT TTAAA
(Blue Heron) inserting a loxP flanked kanamycin selection cassette into the retrieved genomic fragment. Purified targeted plasmids were then transformed into arabinose-induced and electrocompetent SW106 cells to allow for Cre-mediated pop-out of the selection cassette to leave a single loxP site behind. The purified fragment was then co-transformed with a synthesized second targeting cassette (SEQ ID NO:44): CTCAGTGACACATTACACACTTGTGGTG-
CAATGTATGGATTACCTGAATACCCACCTTC CCCA-
GGGAGCAAGCATTTCTCCGTTTTGTGCTTTCTTCA-
GTGAAGTTCCTATTCTCTAG
AAAGTATAGGAACTTCGGTCTGAAGAGGAGTT-
TACGTCCAGCCAAGCTAGCTTGGCTG CAG-
GTCGTCGAAATTCTACCGGGTAGGGGGCTCTATG-
GCTTCTGAGGCGGAAAGAACC
AGCTGGGGCTCGACTAGAGCTTGCGGAAC-
CCGAAGTTCCTATTCTCTAGAAAGTATAG GAACT-
TCATCAGTCAGGTACATATATAACTTCGTATAATG-
TATGCTATACGAAGTTAT
GCACAGTAGATCCTCAACCCAAGTGGATAAGAGAT-
GACAATAGCTTTCCAAGAGAGA CAGTTAT-
GAGGGACCACGCAGAAATGAACAAAGCACAGT-
TGGT (Blue Heron), for the insertion of a PGK-em7-Neo-pA resistance gene flanked by two Frt sites and a single loxP site to create the conditional targeting vector. This selection cassette remained in the conditional targeting vector for positive selection in ES cells and was subsequently removed by transient transfection of cDNA encoding Flp in ES cells to create the conditional CD83$^{fl}$ allele (FIG. 16A). ES cells carrying the CD83$^{fl}$ allele were then injected into mouse blastocysts to generate chimeric mice, which were then used to generate homozygous CD83$^{fl/fl}$ mice. CD83 knockout mice were generated using a strategy similar to that used in Fujimoto, Y. et al., Cell 108, 755-767, 2002, which is incorporated herein by reference. CD83$^{fl/fl}$ mice were bred to mice with transgenic expression of Cre recombinase under control of the CD11c promoter to generate mice deficient for CD83 specifically in DCs (CD83$^{fl/fl}$ CD11c-Cre). CD83$^{fl/fl}$ CD11c-Cre mice showed no gross morphological abnormalities and unlike global CD83 knockout mice, had normal numbers of CD4 T cells in the spleen when compared to CD83$^{wt/wt}$ CD11c-Cre littermates, since CD83 expression on thymic epithelial cells was presumably not affected in these mice (FIG. 16B). DC numbers in the spleen and colon were also similar, but expression of CD83 was lost on most DCs in CD83$^{fl/fl}$ CD11c-Cre mice (FIG. 16C). Loss of CD83 expression in DCs resulted in decreased survival of DSS colitis (FIG. 16D). CD83$^{fl/fl}$ CD11c-Cre DSS treated mice had severe weight loss, retaining significantly less of their initial body weight (77.7%) compared to CD83$^{wt/wt}$ CD11c-Cre littermates (84.9%) by day 8 (FIG. 16E). Furthermore, DSS treatment yielded overt blood around the anus and in stools in 100% of the CD83$^{fl/fl}$ CD11c-Cre mice by day 8 which was not observed in CD83$^{wt/wt}$ CD11c-Cre littermates (FIG. 16F), thus requiring euthanasia for humane reasons. These results indicate that DC CD83 expression was necessary to tolerate DSS induced colitis.

Example 9

Generation and Characterization of Agonist Anti-CD83 Antibodies

Agonist antibodies that specifically bind to an epitope within the extracellular region of human CD83 may be generated by screening an antibody library, such as a phage display library. The antibodies in the library may be human antibodies, humanized antibodies, or chimeric antibodies. The antibodies in the library may also be single chain antibodies or single domain antibodies. Alternatively, peptides from the extracellular region of human CD83 may be used for immunization of mice, and anti-CD83 antibodies are identified for CD83 agonist activity as indicated below.

Binding of Cell Surface CD83 by Agonist Anti-CD83 Antibodies:

To identify antibodies that bind to cell surface CD83 on dendritic cells, the binding ability of generated antibodies are screened by flow cytometry analysis. Briefly, immature dendritic cells (iDCs) are treated with a cytokine cocktail to induce DC maturation and surface expression of CD83. mDCs are treated with the generated antibodies simultaneously with the DC maturation stimulus prior to fixation and flow cytometry. Antibodies that specifically bind to CD83 expressed on the surface of mDCs are identified by analyzing the flow cytometry data. Alternatively, the generated anti-CD83 antibodies are screened using cell aggregation assays. Briefly, CHO cells expressing hCD83 (CHO-hCD83) are detached from flasks with 2 mM EDTA, washed and resuspended in HBSS medium containing 2% FBS/10 mM EDTA but lacking $Ca^{2+}$ or $Mg^{2+}$. The cells are subsequently resuspended at $10^6$/ml and passed through a 70 µm filter to obtain a single cell suspension for plating on low adhesion 10 cm culture dishes. CHO-hCD83 cells are subsequently treated with the generated antibodies and incubated at 37° C. for 90 minutes in an orbital platform shaker prior to fixation with 4% PFA. Antibodies that block cell aggregation of CHO-hCD83 cells due to competition for CD83 homotypic binding are identified by microscopy imaging of cells. These antibodies may be further characterized for their binding to human CD83 and agonist activities.

Changes in Cytokine Release from mDCs with Agonist Anti-CD83 Antibody Treatment:

To identify anti-CD83 antibodies with CD83 agonist activity, the effect of CD83 treatment on pro-inflammatory and anti-inflammatory cytokine secretion by mDCs are assessed. Briefly, iDCs are treated with a cytokine cocktail to induce DC maturation and surface expression of CD83. Treatment of mDCs with the generated antibodies are given simultaneously with the DC maturation stimulus. Cell culture supernatants are collected 48 hours after maturation of DCs and secretion of pro-inflammatory cytokines MCP-1 and IL-12p40 as well as the anti-inflammatory cytokine IL-1ra are analyzed by ELISA. Anti-CD83 antibodies that inhibit release of pro-inflammatory cytokine MCP-1 and IL-12p40 and/or induce release of anti-inflammatory cytokine IL-1ra are identified as antibodies having agonist activities.

Decreased Expression of mDC Cell Surface Activation Markers with Agonist Anti-CD83 Antibody Treatment:

To identify agonist anti-CD83 antibodies that inhibit activation of mDCs, the generated antibodies are screened for the ability to reduce expression of cell surface activation markers. Briefly, immature dendritic cells (iDCs) are treated with a cytokine cocktail to induce DC maturation. mDCs are treated with the generated antibodies simultaneously with the DC maturation stimulus. Expression of cell surface activation markers, CD83 and HLA-DR (MHCII), on mDCs are examined by staining cells with fluorochrome conjugated antibodies to CD83 or MHCII, and analyzing the cells by flow cytometry. Anti-CD83 antibodies that decrease cell surface expression of CD83 and/or HLA-DR on mDC are identified as antibodies having agonist activities.

Inhibition of the MAPK and mTOR Signaling Pathways with Agonist Anti-CD83 Antibody Treatment:

To identify agonist anti-CD83 antibodies that inhibit activation of the MAPK and mTOR (mammalian target of rapamycine) signaling in mDCs, the generated antibodies are screened for the ability to inhibit phosphorylation of downstream signaling proteins. Briefly, immature dendritic cells (iDCs) are treated with a cytokine cocktail to induce DC maturation. mDCs are treated with the generated antibodies simultaneously with the DC maturation stimulus. Cell lysates from treated mDCs are subjected to SDS-PAGE followed by western blot analysis with specific phospho-antibodies. Anti-CD83 antibodies that inhibit the MAPK signaling pathway by decreased phosphorylation of p38 and CREB proteins in mDCs and/or that inhibit the mTOR signaling pathway by decreased phosphorylation of the mTOR protein are identified as antibodies having agonist activities.

Candidate agonist anti-CD83 antibodies identified from the antibody screening methods outlined above are used at various dosages to treat autoimmune disease in animal models, such as the IL-10 knockout mouse model for colitis (Scheinin et al., *Clin Exp Immunol.*, 133:38-43, 2003) and the experimental autoimmune encephalomyelitis mouse model for multiple sclerosis (Miller et al., *Curr Protoc Immunol.*, Chapter 15:Unit 15.1, 2007).

Example 10

Generation of Anti-CD83 Antibodies

Materials and Methods

Media and Antibodies

ClonaCell-HY Medium B (Cat#03802), Medium C (Cat#03803), Medium D (Cat#03804) and Medium E (Cat#03805) were from StemCell Technologies. Cytofusion Medium C (Cat# LCM-C) used for electrofusion was from Cyto Pulse Sciences. Goat anti-hamster IgG (H+L)-HRP conjugated antibody (Cat#127-035-160) was from Jackson ImmunoResearch Laboratories. TMB one component HRP microwell substrate (Cat# TMBW-1000-01) and TMB stop reagent (Cat# BSTP-1000-01) were from BioFx Laboratories.

In Vivo Immunization

Armenian hamsters were immunized with 2 µg per injection per hamster recombinant murine and human CD83 resuspended in monophosphoryl lipid A/trehalose dicorynomycolate adjuvant by intraperitoneal injection at 3 to 4 day intervals for a total of 18 boosts. Three days after the final pre-fusion boost, lymphocytes from immunized hamster spleens were harvested.

Hybridoma Generation and Antibody Screening

Isolated hamster spleen cells were fused with PU-1 myeloma cells (American Type Culture Collection) by using the Cyto Pulse CEEF-50 apparatus (Cyto Pulse Sciences). Briefly, after twice washing with Cytofusion Medium C, the isolated spleen cells and PU-1 cells were mixed at a 1:1 ratio and then resuspended at 10 million cells per ml in Cytofusion Medium C. Electrofusion was performed according to the manufacturer's instructions. Fused cells were cultured in ClonaCell-HY Medium C overnight at 37° C. in a 7% $CO_2$ incubator. The next day, fused cells were centrifuged and then resuspended in 10 ml ClonaCell-HY Medium C followed by gentle mixing with 90 ml Methylcellulose-based ClonaCell-HY Medium D containing HAT components. The cells were plated into 100 mm Petri dishes (Cat#351029, Becton Dickinson) and allowed to grow in 37° C. in a 7% $CO_2$ incubator. After 10 days incubation, single hybridoma clones were picked by ClonePix (Genetix, United Kingdom) and transferred into 96-well cell culture plates (#353075, Becton Dickinson) containing 200 µL per well of ClonaCell-HY Medium E. Hybridoma culture media was changed prior to ELISA screening. Three days after media change, hybridoma supernatants were screened by ELISA against either human CD83 or mouse CD83 for identification of ELISA positive clones.

Hamster Abs Purification

The hybridoma supernatants were purified by Protein A affinity chromatography, then sterile filtered (0.2 µm pore size, Nalge Nunc International, NY, USA) and stored at 4° C. in PBS. The purified mAbs were confirmed by ELISA before further testing using functional assays.

ELISA Assays

ELISA assays was performed according to standard protocol. ELISA 96-well microtiter plates (Greiner, Germany) were coated with 100 µL per well of human or mouse CD83 at a concentration of 2 µg per ml in 0.05 M carbonate buffer (pH 9.6) and incubated at 4° C. overnight. After washing the wells three times with wash buffer (0.05% Tween 20 in PBS, Sigma), plates were blocked with 100 µL ELISA assay diluents with BSA. About 100 µL of cultured supernatants or diluted purified mAbs were added and incubated for 1 h at room temperature. The plates were washed three times and incubated with HRP conjugated goat anti-hamster IgG (H+L) for 1 hour. After washing the wells three times, bound HRP conjugated antibodies were detected by addition of 100 µL per well the TMB substrate (BioFX Laboratories, MD, USA) and the plate was incubated for 5 min. The reactions were stopped by addition of 100 µL per well of stop reagent (BioFX, Laboratories, MD, USA) and color was detected at $A_{630\ nm}$ to identify or confirm antibodies that bound to human or mouse CD83.

FACS Binding Assays

The generated antibodies were assayed for their ability to bind human CD83 or mouse CD83 stably expressed on CHO cells. To generate an expression vector for the production of the stable cell lines, a DNA fragment encoding an N-terminal HIS-tagged human CD83 (hCD83) or an N-terminal HIS-tagged mouse CD83 (mCD83) was cloned into the neomycin-resistance plasmid, pRKneo (Crowley et al., *Proc Natl Acad Sci USA.*, 90(11):5021-5025, 1993), at the XbaI and XhoI sites to produce hCD83.pRKneo or mCD83.pRKneo, respectively. CHO cells were transfected with hCD83.pRKneo or mCD83.pRKneo using Fugene (Roche) and the top 10% of CD83 positive cells were sorted by FACS then selected with G418 (400 mg/ml; GIBCO) to generate the stable CHO-hCD83 or CHO-mCD83 cell line, respectively. CHO-hCD83 and CHO-mCD83 cells were resuspended in a FACS buffer containing PBS/2% BSA/2 mM EDTA and incubated with anti-human CD83 antibodies or anti-mouse CD83 antibodies for 30 minutes on ice. Cells were washed with FACS buffer and then incubated with a fluorochrome conjugated anti-hamster IgG secondary antibody for 30 minutes on ice in the dark. Cells were washed with FACS buffer and analyzed by flow cytometry on a LSR II flow cytometer using FACSDiva software (Becton Dickinson). Data analysis and construction of diagrams was done using FlowJo v.9.4.11.

Subcloning

Hybridoma clones that produced antibodies capable of binding mouse or human CD83 were subjected to at least 1 round of single cell subcloning for production of chimeric antibodies containing the wild type mouse IgG2a constant region together with the hamster variable region. The antibodies were subsequently sequenced.

Results

Figure 17:
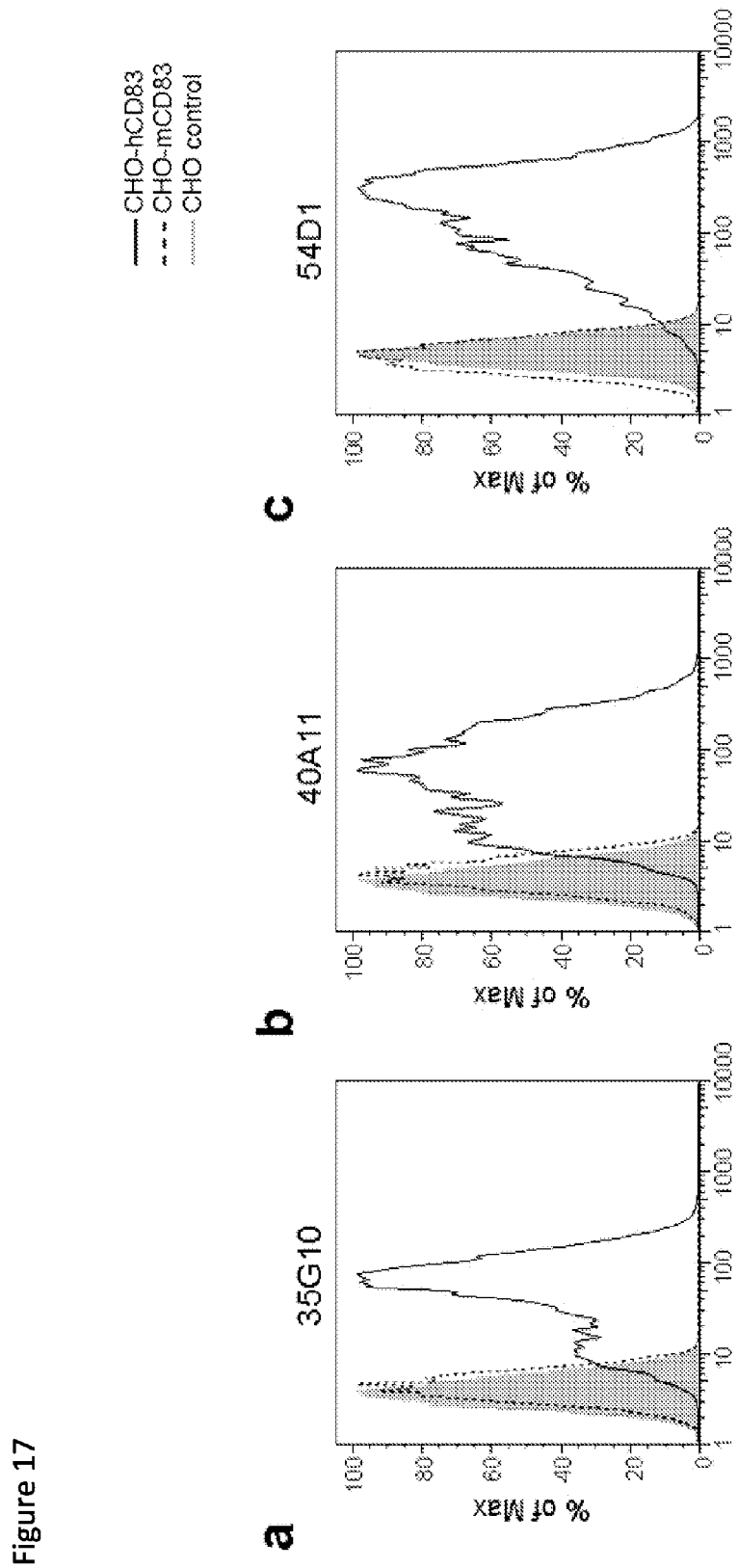
FIG. 17 shows that anti-human CD83 antibodies bound to cells expressing CD83. Quantification by flow cytometry demonstrated specific binding of anti-CD83 antibodies (a) 35G10, (b) 40A11, (c) 54AD1, (d) 59G10, (e) 75A1, and (f) 7C7 to CHO cells expressing human CD83 (black line), but not to cells expressing mouse CD83 (dashed line). (g) Anti-CD83 antibody 60B10 bound to CHO cells expressing human CD83, but also showed cross-reactivity with CHO cells expressing mouse CD83. No binding was seen on the parental CHO cell line (solid gray histogram).
Figure 17:
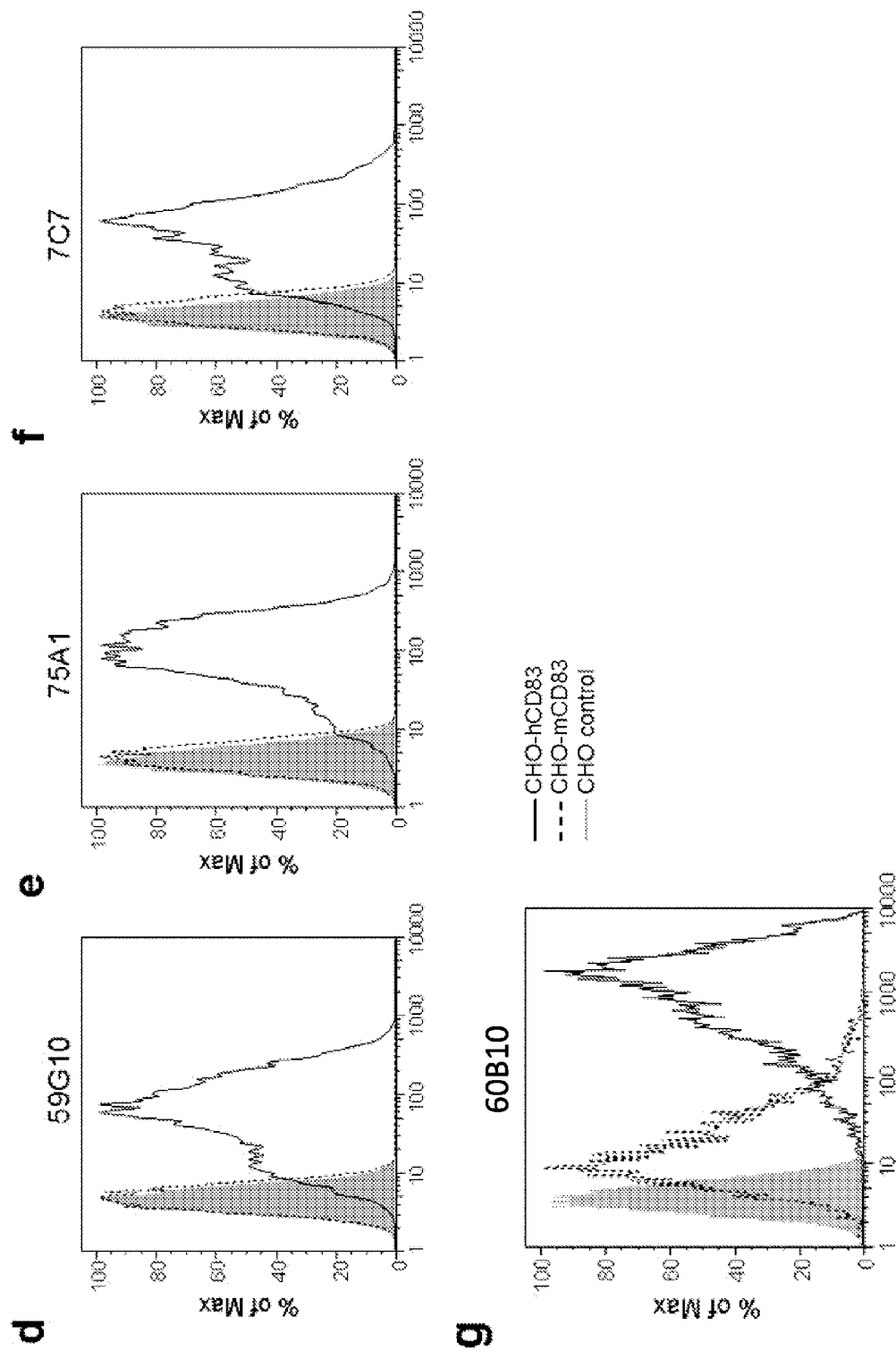
Figure 18:
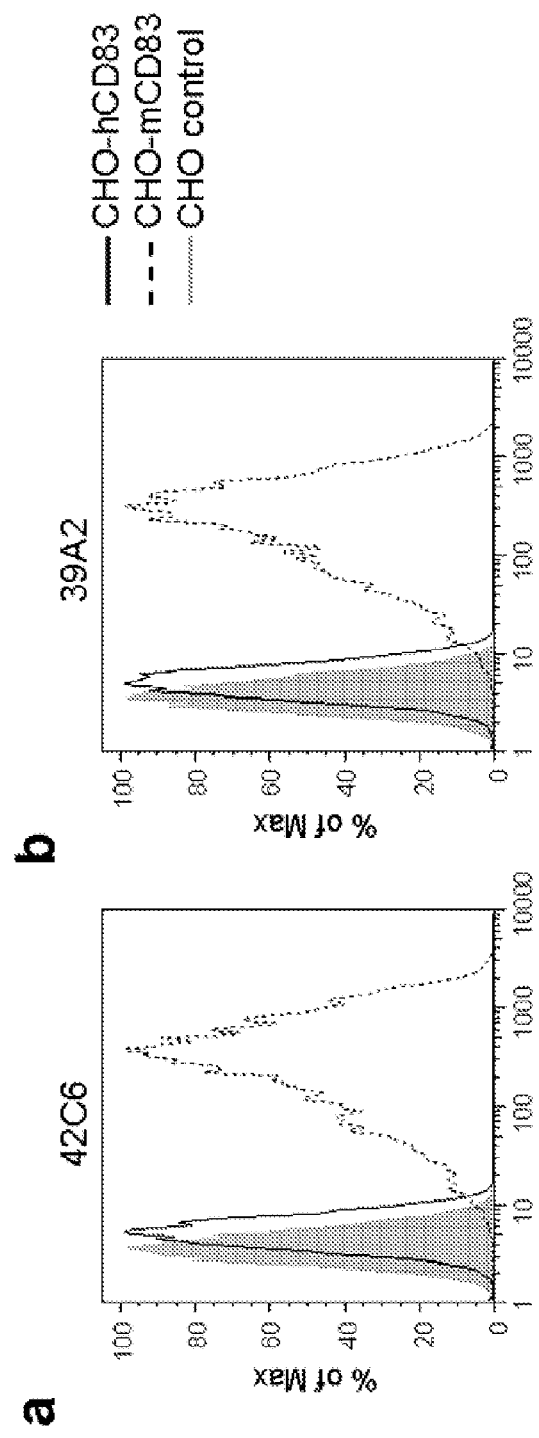
FIG. 18 shows that anti-mouse CD83 antibodies bound to CHO cells expressing mouse CD83. Quantification by flow cytometry demonstrated specific binding of anti-CD83 antibodies (a) 42C6 and (b) 39A2 to CHO cells expressing mouse CD83 (dashed line), but not to CHO cells expressing human CD83 (black line) or the parental CHO cell line (solid gray histogram).

Data analysis of the FACS binding assays identified 9 hybridoma clones that produced antibodies with the ability to bind CD83. Anti-CD83 antibodies 35G10, 40A11, 54D11, 59G10, 75A1 and 7C7 bound to CHO cells expressing human CD83 (black line), but not to cells expressing mouse CD83 (dashed line) or to parental CHO cells that lacked CD83 expression (solid histogram) (FIG. 17A-F). The anti-CD83 antibody 60B10 bound to CHO cells expressing human CD83, but also showed cross-reactivity with CHO cells expressing mouse CD83 (FIG. 17G). The anti-CD83 antibodies, 42C6 and 39A2, bound specifically to CHO cells expressing mouse CD83 (dashed line), but not to CHO cells expressing human CD83 (black line) or the parental CHO cell line that lacked CD83 expression (FIGS. 18A and B).

Sequencing of the antibodies isolated from the hybridoma clones resulted in the following sequences (variable region underlined and HVRs are bold):

39A2 Anti-Mouse CD83 Heavy Chain DNA Sequence (SEQ ID NO: 4)

```
CAGGTGCAGCTGAAGGAGTCAGGACCTGGCCTAGTGAAGCCCTCACAGTCAATG
TCCCTCACTTGCTCTGTCAATGGTTTCTCCATCACCAGTCGTTACTGGTGGACCTG
GATCAGGCAGTTCCCAGGGAAGAACCTGGAGTGGATGGGTTACATAAGTTATAG
TGGTGGCACCAGCTACAACCCCTCCCTCAAGAGCCGCATCTCCATCACCCGAGAC
ACATCCAAGAACCAGTTCTTCCTGCACCTGAACTCTGTGACCACTGCTGACACAG
CCACATATTACTGTGCAAGAGATCTCTACGGTACCTACTTTGATTACTGGGGCCA
AGGAACCCTGGTCACCGTCTCCTCAGCCTCCACCAAGGGCCCATCGGTCTATCCA
CTGGCTCCTGTGTGTGGAGATACAACTGGCTCCTCGGTGACTCTAGGATGCCTGG
TCAAGGGTTATTTCCCTGAGCCAGTGACCTTGACCTGGAACTCTGGATCCCTGTC
CAGTGGTGTGCACACCTTCCCAGCTGTCCTGCAGTCTGACCTCTACACCCTCAGC
AGCTCAGTGACTGTAACCTCGAGCACCTGGCCCAGCCAGTCCATCACCTGCAATG
TGGCCCACCCGGCAAGCAGCACCAAGGTGGACAAGAAAATTGAGCCCAGAGGA
CCCACAATCAAGCCCTGTCCTCCATGCAAATGCCCAGCACCTAACCTCTTGGGTG
GACCATCCGTCTTCATCTTCCCTCCAAAGATCAAGGATGTACTCATGATCTCCCTG
AGCCCCATAGTCACATGTGTGGTGGTGGATGTGAGCGAGGATGACCCAGATGTC
CAGATCAGCTGGTTTGTGAACAACGTGGAAGTACACACAGCTCAGACACAAACC
CATAGAGAGGATTACAACAGTACTCTACGCGTGGTCAGTGCCCTCCCCATCCAGC
ACCAGGACTGGATGAGTGGCAAGGAGTTCAAATGCAAGGTCAACAACAAAGACC
TCCCAGCGCCCATCGAGAGAACCATCTCAAAACCCAAAGGGTCAGTAAGAGCTC
CACAGGTATATGTCTTGCCTCCACCAGAAGAAGAGATGACTAAGAAACAGGTCA
CTCTGACCTGCATGGTCACAGACTTCATGCCTGAAGACATTTACGTGGAGTGGAC
CAACAACGGGAAAACAGAGCTAAACTACAAGAACACTGAACCAGTCCTGGACTC
TGATGGTTCTTACTTCATGTACAGCAAGCTGAGAGTGGAAAAGAAGAACTGGGT
GGAAAGAAATAGCTACTCCTGTTCAGTGGTCCACGAGGGTCTGCACAATCACCA
CACGACTAAGAGCTTCTCCCGGACTCCGGGTAAA
```

39A2 Anti-mouse CD83 Heavy Chain Amino Acid Sequence (SEQ ID NO: 5)

QVQLKESGPGLVKPSQSMSLTCSVNGFSITSRYWWTWIRQFPGKNLEWM**GYISYSG
GTSYNPSLKSRISITRDTSKNQFFLHLNSVTTADTATYYCARDLYGTYFDY**WGQGTL
VTVSSASTKGPSVYPLAPVCGDTTGSSVTLGCLVKGYFPEPVTLTWNSGSLSSGVHTF
PAVLQSDLYTLSSSVTVTSSTWPSQSITCNVAHPASSTKVDKKIEPRGPTIKPCPPCKC
PAPNLLGGPSVFIFPPKIKDVLMISLSPIVTCVVVDVSEDDPDVQISWFVNNVEVHTAQ

TQTHREDYNSTLRVVSALPIQHQDWMSGKEFKCKVNNKDLPAPIERTISKPKGSVRA

PQVYVLPPPEEEMTKKQVTLTCMVTDFMPEDIYVEWTNNGKTELNYKNTEPVLDSD

GSYFMYSKLRVEKKNWVERNSYSCSVVHEGLHNHHTTKSFSRTPGK

39A2 Anti-mouse CD83 Heavy Chain Variable
Region Amino Acid Sequence
(SEQ ID NO: 6)
QVQLKESGPGLVKPSQSMSLTCSVNGFSITSRYWWTWIRQFPGKNLEWMGYISYSG

GTSYNPSLKSRISITRDTSKNQFFLHLNSVTTADTATYYCARDLYGTYFDYWGQGTL

VTVSS

39A2 HVR-H1 Amino Acid Sequence
(SEQ ID NO: 7)
GFSITSRYWWT

39A2 HVR-H2 Amino Acid Sequence
(SEQ ID NO: 8)
GYISYSGGTSYNPSLKS

39A2 HVR-H3 Amino Acid Sequence
(SEQ ID NO: 9)
ARDLYGTYFDY

39A2 Anti-mouse CD83 Light Chain DNA Sequence
(SEQ ID NO: 10)
CAGTATGAGCTAATTCAGCCAAAGTCTGTGTCAGAGTCTCTAGGGAGAACAGTC

ACCATCTCCTGCAAACGCAGCAGTGGCAACATTGGAAATAACTATGTACACTGGT

ACCAACAGCACTTTGGAAGCTCACCCAAAACTGTGATCTATGATGACAATAAAA

GACCATCTGGGGTTCCTCATAGGTTCTCTGGCTCCATTGACAGCTCCTCAAACTC

AGCTTCCCTGACTATCACTGATCTGCAGATTGAAGATGAAGCTGAATACTACTGT

CAATCTGCTTGGGTGTTCGGTTCAGGCACCAAAGTGACTGTCCTACGCGCTGATG

CTGCACCAACTGTATCCATCTTCCCACCATCCAGTGAGCAGTTAACATCTGGAGG

TGCCTCAGTCGTGTGCTTCTTGAACAACTTCTACCCCAAAGACATCAATGTCAAG

TGGAAGATTGATGGCAGTGAACGACAAAATGGCGTCCTGAACAGTTGGACTGAT

CAGGACAGCAAAGACAGCACCTACAGCATGAGCAGCACCCTCACGTTGACCAAG

GACGAGTATGAACGACATAACAGCTATACCTGTGAGGCCACTCACAAGACATCA

ACTTCACCCATTGTCAAGAGCTTCAACAGGAATGAGTGT

39A2 Anti-mouse CD83 Light Chain Amino
Acid Sequence
(SEQ ID NO: 11)
QYELIQPKSVSESLGRTVTISCKRSSGNIGNNYVHWYQQHFGSSPKTVIYDDNKRPS

GVPHRFSGSIDSSSNSASLTITDLQIEDEAEYYCQSAWVFGSGTKVTVLRADAAPTVSI

FPPSSEQLTSGGASVVCFLNNFYPKDINVKWKIDGSERQNGVLNSWTDQDSKDSTYS

MSSTLTLTKDEYERHNSYTCEATHKTSTSPIVKSFNRNEC

39A2 Anti-mouse CD83 Light Chain Variable
Region Amino Acid Sequence
(SEQ ID NO: 12)
QYELIQPKSVSESLGRTVTISCKRSSGNIGNNYVHWYQQHFGSSPKTVIYDDNKRPS

GVPHRFSGSIDSSSNSASLTITDLQIEDEAEYYCQSAWVFGSGTKVTVL

39A2 HVR-L 1 Amino Acid Sequence
(SEQ ID NO: 13)
KRSSGNIGNNYVH

39A2 HVR-L2 Amino Acid Sequence
(SEQ ID NO: 14)
DDNKRPS

39A2 HVR-L3 Amino Acid Sequence
(SEQ ID NO: 15)
QSAWV

42C6 Anti-mouse CD83 Heavy Chain DNA
Sequence
(SEQ ID NO: 16)
<u>CAGGTGCAGCTGAAGGAGTCAGGACCTGGCCTAGTGAAGCCCTCACAGTCAATG</u>

<u>TCCCTCACTTGCTCTGTCAATGGTTTCTCCATCACCAGTCGTTACTGGTGGACCTG</u>

<u>GATCAGGCAGTTCCCAGGGAAGAACCTGGAGTGGATGGGTTACATAAGTTATAG</u>

<u>TGGTGGCACCAGCTACAACCCCTCCCTCAAGAGCCGCATCTCCATCACCCGAGAC</u>

<u>ACATCCAAGAACCAGTTCTTCCTGCACCTGAACTCTGTGACCACTGCTGACACAG</u>

<u>CCACATATTACTGTGCAAGAGATCTCTACGGTACCTACTTTGATTACTGGGGCCA</u>

<u>AGGAACCATGGTCACCGTCTCCTCA</u>GCCTCCACCAAGGGCCCATCGGTCTATCCA

CTGGCTCCTGTGTGTGGAGATACAACTGGCTCCTCGGTGACTCTAGGATGCCTGG

TCAAGGGTTATTTCCCTGAGCCAGTGACCTTGACCTGGAACTCTGGATCCCTGTC

CAGTGGTGTGCACACCTTCCCAGCTGTCCTGCAGTCTGACCTCTACACCCTCAGC

AGCTCAGTGACTGTAACCTCGAGCACCTGGCCCAGCCAGTCCATCACCTGCAATG

TGGCCCACCCGGCAAGCAGCACCAAGGTGGACAAGAAAATTGAGCCCAGAGGA

CCCACAATCAAGCCCTGTCCTCCATGCAAATGCCCAGCACCTAACCTCTTGGGTG

GACCATCCGTCTTCATCTTCCCTCCAAAGATCAAGGATGTACTCATGATCTCCCTG

AGCCCCATAGTCACATGTGTGGTGGTGGATGTGAGCGAGGATGACCCAGATGTC

CAGATCAGCTGGTTTGTGAACAACGTGGAAGTACACACAGCTCAGACACAAACC

CATAGAGAGGATTACAACAGTACTCTACGCGTGGTCAGTGCCCTCCCCATCCAGC

ACCAGGACTGGATGAGTGGCAAGGAGTTCAAATGCAAGGTCAACAACAAAGACC

TCCCAGCGCCCATCGAGAGAACCATCTCAAAACCCAAAGGGTCAGTAAGAGCTC

CACAGGTATATGTCTTGCCTCCACCAGAAGAAGAGATGACTAAGAAACAGGTCA

CTCTGACCTGCATGGTCACAGACTTCATGCCTGAAGACATTTACGTGGAGTGGAC

CAACAACGGGAAAACAGAGCTAAACTACAAGAACACTGAACCAGTCCTGGACTC

TGATGGTTCTTACTTCATGTACAGCAAGCTGAGAGTGGAAAAGAAGAACTGGGT

GGAAAGAAATAGCTACTCCTGTTCAGTGGTCCACGAGGGTCTGCACAATCACCA

CACGACTAAGAGCTTCTCCCGGACTCCGGGTAAA

42C6 Anti-mouse CD83 Heavy Chain Amino
Acid Sequence
(SEQ ID NO: 17)
<u>QVQLKESGPGLVKPSQSMSLTCSVNGFSITSRYWWTWIRQFPGKNLEWMGYISYSG</u>

<u>GTSYNPSLKSRISITRDTSKNQFFLHLNSVTTADTATYYCARDLYGTYFDYWGQGT</u>

<u>MVTVSS</u>ASTKGPSVYPLAPVCGDTTGSSVTLGCLVKGYFPEPVTLTWNSGSLSSGVH

TFPAVLQSDLYTLSSSVTVTSSTWPSQSITCNVAHPASSTKVDKKIEPRGPTIKPCPPCK

CPAPNLLGGPSVFIFPPKIKDVLMISLSPIVTCVVVDVSEDDPDVQISWFVNNVEVHTA

QTQTHREDYNSTLRVVSALPIQHQDWMSGKEFKCKVNNKDLPAPIERTISKPKGSVR

APQVYVLPPPEEEMTKKQVTLTCMVTDFMPEDIYVEWTNNGKTELNYKNTEPVLDS

DGSYFMYSKLRVEKKNWVERNSYSCSVVHEGLHNHHTTKSFSRTPGK

42C6 Anti-mouse CD83 Heavy Chain Variable
Region Amino Acid Sequence
(SEQ ID NO: 18)
QVQLKESGPGLVKPSQSMSLTCSVNGFSITSRYWWTWIRQFPGKNLEWMGYISYSG

GTSYNPSLKSRISITRDTSKNQFFLHLNSVTTADTATYYCARDLYGTYFDYWGQGT

MVTVSS

42C6 HVR-H1 Amino Acid Sequence
(SEQ ID NO: 19)
GFSITSRYWWT

42C6 HVR-H2 Amino Acid Sequence
(SEQ ID NO: 20)
GYISYSGGTSYNPSLKS

42C6 HVR-H3 Amino Acid Sequence
(SEQ ID NO: 21)
ARDLYGTYFDY

42C6 Anti-mouse CD83 Light Chain DNA Sequence
(SEQ ID NO: 22)
CAGTATGAGCTAATTCAGCCAAAGTCTGTGTCAGAGTCTCTAGGGAGAACAGTC

ACCATCTCCTGCAAACGCAGCAGTGGCAACATTGGAAATAACTATGTACACTGGT

ACCAACAGCACTTTGGAAGCTCACCCAAAACTGTGATCTATGATGACAATAAAA

GACCATCTGGGGTTCCTCATAGGTTCTCTGGCTCCATTGACAGCTCCTCAAACTC

AGCTTCCCTGACTATCACTGATCTGCAGATTGAAGATGAAGCTGAATACTACTGT

CAATCTGCTTGGGTGTTCGGTTCAGGCACCAAAGTGACTGTCCTACGCGCTGATG

CTGCACCAACTGTATCCATCTTCCCACCATCCAGTGAGCAGTTAACATCTGGAGG

TGCCTCAGTCGTGTGCTTCTTGAACAACTTCTACCCCAAAGACATCAATGTCAAG

TGGAAGATTGATGGCAGTGAACGACAAAATGGCGTCCTGAACAGTTGGACTGAT

CAGGACAGCAAAGACAGCACCTACAGCATGAGCAGCACCCTCACGTTGACCAAG

GACGAGTATGAACGACATAACAGCTATACCTGTGAGGCCACTCACAAGACATCA

ACTTCACCCATTGTCAAGAGCTTCAACAGGAATGAGTGT

42C6 Anti-mouse CD83 Light Chain Amino
Acid Sequence
(SEQ ID NO: 23)
QYELIQPKSVSESLGRTVTISCKRSSGNIGNNYVHWYQQHFGSSPKTVIYDDNKRPS

GVPHRFSGSIDSSSNSASLTITDLQIEDEAEYYCQSAWVFGSGTKVTVLRADAAPTVSI

FPPSSEQLTSGGASVVCFLNNFYPKDINVKWKIDGSERQNGVLNSWTDQDSKDSTYS

MSSTLTLTKDEYERHNSYTCEATHKTSTSPIVKSFNRNEC

42C6 Anti-mouse CD83 Light Chain Variable
Region Amino Acid Sequence
(SEQ ID NO: 24)
QYELIQPKSVSESLGRTVTISCKRSSGNIGNNYVHWYQQHFGSSPKTVIYDDNKRPS

GVPHRFSGSIDSSSNSASLTITDLQIEDEAEYYCQSAWVFGSGTKVTVL

42C6 HVR-L1 Amino Acid Sequence
(SEQ ID NO: 25)
KRSSGNIGNNYVH

42C6 HVR-L2 Amino Acid Sequence
(SEQ ID NO: 26)
DDNKRPS

42C6 HVR-L3 Amino Acid Sequence
(SEQ ID NO: 27)
QSAWV

-continued

60B10 Anti-human CD83 Heavy Chain DNA Sequence
(SEQ ID NO: 28)

<u>CAGGTGCAGCTGAAGGAGTCAGGACCTGGCCTCGTGAAGCCCTCACAGTCACTG</u>

<u>TCCCTCACTTGCTCTGTCACTGGTTTCTCCATCACCACCGGTGGTTACTGGTGGAC</u>

<u>CTGGATCAGGCAGTTCCCAGGGCAGAAGCTGGAGTGGATGGGGTACATATTTAG</u>

<u>TAGTGGTAACACCAACTACAACCCATCCATCAAGAGCCGCATCTCCATAACCAG</u>

<u>AGACACATCCAAGAACCAGTTCTTCCTGCAGCTGAACTCTGTGACTACTGAGGGG</u>

<u>GACACAGCCAGATATTATTGTGCAAGGGCCTACGGTAAGCTAGGCTTTGATTACT</u>

<u>GGGGCCAAGGAACCCTGGTCACCGTCTCCTC</u>AGCCTCCACCAAGGGCCCATCGG

TCTATCCACTGGCTCCTGTGTGTGGAGATACAACTGGCTCCTCGGTGACTCTAGG

ATGCCTGGTCAAGGGTTATTTCCCTGAGCCAGTGACCTTGACCTGGAACTCTGGA

TCCCTGTCCAGTGGTGTGCACACCTTCCCAGCTGTCCTGCAGTCTGACCTCTACAC

CCTCAGCAGCTCAGTGACTGTAACCTCGAGCACCTGGCCCAGCCAGTCCATCACC

TGCAATGTGGCCCACCCGGCAAGCAGCACCAAGGTGGACAAGAAAATTGAGCCC

AGAGGACCCACAATCAAGCCCTGTCCTCCATGCAAATGCCCAGCACCTAACCTCT

TGGGTGGACCATCCGTCTTCATCTTCCCTCCAAAGATCAAGGATGTACTCATGAT

CTCCCTGAGCCCCATAGTCACATGTGTGGTGGTGGATGTGAGCGAGGATGACCCA

GATGTCCAGATCAGCTGGTTTGTGAACAACGTGGAAGTACACACAGCTCAGACA

CAAACCCATAGAGAGGATTACAACAGTACTCTACGCGTGGTCAGTGCCCTCCCCA

TCCAGCACCAGGACTGGATGAGTGGCAAGGAGTTCAAATGCAAGGTCAACAACA

AAGACCTCCCAGCGCCCATCGAGAGAACCATCTCAAAACCCAAAGGGTCAGTAA

GAGCTCCACAGGTATATGTCTTGCCTCCACCAGAAGAAGAGATGACTAAGAAAC

AGGTCACTCTGACCTGCATGGTCACAGACTTCATGCCTGAAGACATTTACGTGGA

GTGGACCAACAACGGGAAAACAGAGCTAAACTACAAGAACACTGAACCAGTCCT

GGACTCTGATGGTTCTTACTTCATGTACAGCAAGCTGAGAGTGGAAAAGAAGAA

CTGGGTGGAAAGAAATAGCTACTCCTGTTCAGTGGTCCACGAGGGTCTGCACAAT

CACCACACGACTAAGAGCTTCTCCCGGACTCCGGGTAAA

60B10 Anti-human CD83 Heavy Chain Amino
Acid Sequence
(SEQ ID NO: 29)
<u>QVQLKESGPGLVKPSQSLSLTCSVTGFSITTGGYWWTWIRQFPGQKLEWMGYIFSS</u>

<u>GNTNYNPSIKSRISITRDTSKNQFFLQLNSVTTEGDTARYYCARAYGKLGFDYWGQ</u>

<u>GTLVTVSS</u>ASTKGPSVYPLAPVCGDTTGSSVTLGCLVKGYFPEPVTLTWNSGSLSSGV

HTFPAVLQSDLYTLSSSVTVTSSTWPSQSITCNVAHPASSTKVDKKIEPRGPTIKPCPPC

KCPAPNLLGGPSVFIFPPKIKDVLMISLSPIVTCVVVDVSEDDPDVQISWFVNNVEVHT

AQTQTHREDYNSTLRVVSALPIQHQDWMSGKEFKCKVNNKDLPAPIERTISKPKGSV

RAPQVYVLPPPEEEMTKKQVTLTCMVTDFMPEDIYVEWTNNGKTELNYKNTEPVLD

SDGSYFMYSKLRVEKKNWVERNSYSCSVVHEGLHNHHTTKSFSRTPGK

60B10 Anti-human CD83 Heavy Chain Variable
Region Amino Acid Sequence
(SEQ ID NO: 30)
<u>QVQLKESGPGLVKPSQSLSLTCSVTGFSITTGGYWWTWIRQFPGQKLEWMGYIFSS</u>

<u>GNTNYNPSIKSRISITRDTSKNQFFLQLNSVTTEGDTARYYCARAYGKLGFDYWGQ</u>

<u>GTLVTVSS</u>

60B10 HVR-H1 Amino Acid Sequence
(SEQ ID NO: 31)
GFSITTGGYWWT

60B10 HVR-H2 Amino Acid Sequence
(SEQ ID NO: 32)
GYIFSSGNTNYNPSIKS

60B10 HVR-H3 Amino Acid Sequence
(SEQ ID NO: 33)
CARAYGKLGFDY

60B10 Anti-human CD83 Light Chain DNA Sequence
(SEQ ID NO: 34)
CAACCTGTGCTGACTCAGTCACCCTCTGCCTCTGCCTCCCTGGGAAACTCAGTCA

AAATCACCTGTACCCTGAGTAGTCAGCACAGCACCTATACCATTGGTTGGTACCA

GCAACATCCAGACAAGGCTCCTAAGTATGTGATGTATGTTAATAGTGATGGAAGC

CACAGCAAGGGGGATGGGATCCCTGATCGCTTCTCTGGCTCCAGCTCTGGGGCTC

ATCGTTACTTAAGCATCTCCAACATTCAGCCTGAAGATGAAGCTGACTATTTCTG

TGGTTCTTCTGATAGCAGTGGGTATGTTTTTGGCAGCGGAACCCAGCTCACCGTC

CTACGCGCTGATGCTGCACCAACTGTATCCATCTTCCCACCATCCAGTGAGCAGT

TAACATCTGGAGGTGCCTCAGTCGTGTGCTTCTTGAACAACTTCTACCCCAAAGA

CATCAATGTCAAGTGGAAGATTGATGGCAGTGAACGACAAAATGGCGTCCTGAA

CAGTTGGACTGATCAGGACAGCAAAGACAGCACCTACAGCATGAGCAGCACCCT

CACGTTGACCAAGGACGAGTATGAACGACATAACAGCTATACCTGTGAGGCCAC

TCACAAGACATCAACTTCACCCATTGTCAAGAGCTTCAACAGGAATGAGTGT

60B10 Anti-human CD83 Light Chain Amino
Acid Sequence
(SEQ ID NO: 35)
QPVLTQSPSASASLGNSVKITCTLSSQHSTYTIGWYQQHPDKAPKYVMYVNSDGSH

SKGDGIPDRFSGSSSGAHRYLSISNIQPEDEADYFCGSSDSSGYVFGSGTQLTVLRAD

AAPTVSIFPPSSEQLTSGGASVVCFLNNFYPKDINVKWKIDGSERQNGVLNSWTDQDS

KDSTYSMSSTLTLTKDEYERHNSYTCEATHKTSTSPIVKSFNRNEC

60B10 Anti-human CD83 Light Chain Variable
Region Amino Acid Sequence
(SEQ ID NO: 36)
QPVLTQSPSASASLGNSVKITCTLSSQHSTYTIGWYQQHPDKAPKYVMYVNSDGSH

SKGDGIPDRFSGSSSGAHRYLSISNIQPEDEADYFCGSSDSSGYVFGSGTQLTVL

60B10 HVR-L1 Amino Acid Sequence
(SEQ ID NO: 37)
TLSSQHSTYTIG

60B10 HVR-L2 Amino Acid Sequence
(SEQ ID NO: 38)
VNSDGSHSKGD

60B10 HVR-L3 Amino Acid Sequence
(SEQ ID NO: 39)
GSSDSSGYV

Example 11

Figure 19:
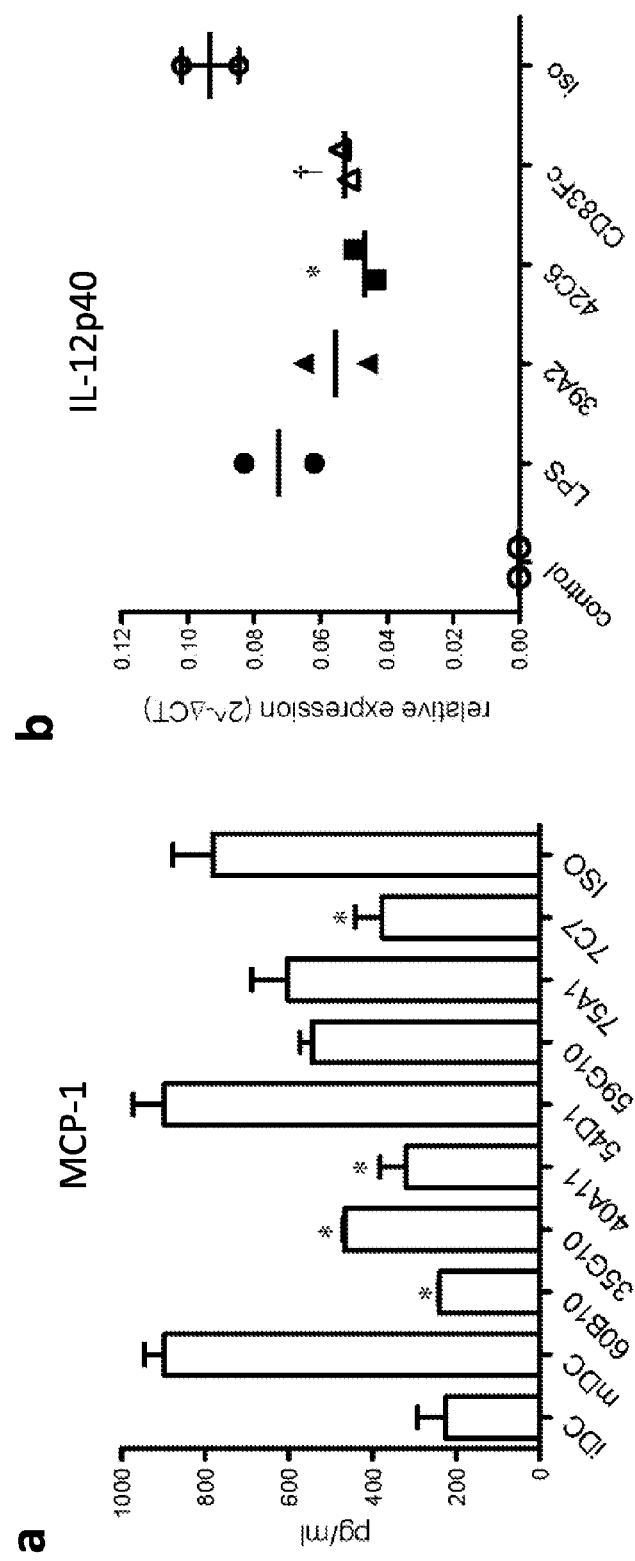
FIG. 19 shows that anti-CD83 antibodies significantly reduced production of proinflammatory cytokines. (a) ELISA data analysis demonstrated that anti-CD83 antibodies 60B10, 35G10, 40A11 or 7C7 significantly reduced production of MCP-1 from mDCs as compared to use of isotype control antibody (ISO); *indicates value significantly different from isotype control treated p=0.0303, p=0.0309, p=0.0369, p=0.0247, respectively. No significant difference was seen in cells given 54D1, 59G10, or 75A1 antibodies. (b) Quantitative PCR analysis of IL-12p40 expression in mouse bone marrow-derived DCs (BMDCs) demonstrated that anti-CD83 antibodies 39A2 or 42C6 significantly reduced LPS-induced CD83 expression as compared to use of isotype control antibody. IL-12p40 expression normalized to β-actin. Each symbol represents cells from independent mice. *, p=0.0372; †, p=0.0438.

Anti-CD83 Antibodies Reduced Release of Pro-Inflammatory Cytokines from mDCs Dendritic cells (DCs) were monitored for an anti-inflammatory response when treated with anti-CD83 antibodies 60B10, 35G10, 40A11, 54D1, 59G10, 75A1, or 7C7. For the assay, monocyte-derived dendritic cells were either left as immature DCs (iDCs) or treated with a cytokine cocktail containing 25 ng/ml rhIL-1β, 100 ng/ml rhIL-6, 50 ng/ml rhTNFα and 1 µg/ml PGE-2 to produce mature DCs (mDCs). Mature DCs were treated with 10 µg/ml of the indicated anti-CD83 antibody and incubated for 48 hrs. After incubation, cell culture supernatants were collected and the secreted pro-inflammatory cytokines were analyzed by ELISA (Invitrogen) according to standard manufacturer's instructions. Analysis of secreted cytokine levels showed that release of pro-inflammatory cytokine MCP-1 was significantly reduced in mDCs treated with anti-CD83 antibodies 60B10, 35G10, 40A11, or 7C7 (FIG. 19A). Treatment with anti-CD83 antibodies 54D1, 59G10, or 75A1 did not significantly reduce production of MCP-1 from mDCs (FIG. 19A).

DCs were monitored for an anti-inflammatory response when treated with anti-mouse CD83 antibodies 39A2 or 42C6. For the assay, mouse bone marrow-derived DCs (BMDCs) were either left as immature DCs (iDCs) or matured with LPS. Matured DCs were treated with 39A2, 42C6 or soluble mouse CD83.Fc protein and subsequently harvested for isolation of RNA to determine expression of the proinflammatory cytokine IL-12p40. Quantitative PCR analysis of IL-12p40 RNA levels showed that treatment of DCs with anti-mouse CD83 antibodies 39A2 or 42C6 together with LPS stimulus, significantly reduced IL-12p40 expression to similar levels observed in DCs treated with soluble mouse CD83.Fc protein (FIG. 19B).

Example 12

Use of Anti-CD83 Antibodies Protects Mice from DSS Induced Colitis

Figure 20:
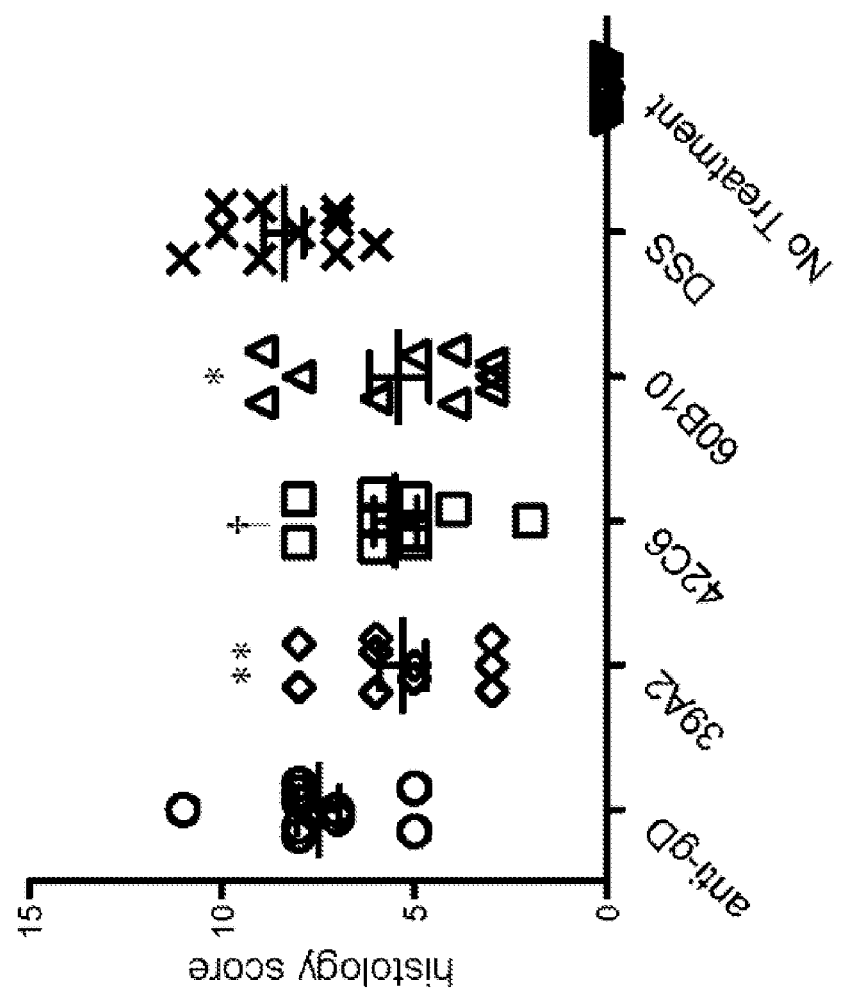
FIG. 20 shows that anti-CD83 antibody protected mice against DSS induced colitis. Mice that were given anti-CD83 antibodies had significantly reduced histology scores compared to those mice given anti-gD control antibody or DSS alone: 39A2, mean=5.3, ** indicates p=0.0011; 42C6, mean=5.5, † indicates p=0.0015; 60B10, mean=5.4, * indicates p=0.0059.

To assess the effect of anti-CD83 antibody treatment in a mouse model of inflammatory bowel disease, colitis was induced in mice by treatment with dextran sodium sulfate (DSS). FVB mice at 8-10 weeks of age were given 200 μg of anti-CD83 antibodies 39A2, 42C6, or 60B10, or of control anti-gD antibody by intraperitoneal injection once per day on day −1, day 1, day 3, and day 5 of the study. Mice were given 6% DSS in drinking water starting on day 0 of the study for 7 days. At day 7 the mice were switched to normal drinking water until cessation of the experiment on day 12. Mice were then euthanized, and the small and large intestine were sectioned and stained with H&E for histology analysis. Sections were randomized and scored double-blind. Colon sections from mice treated with DSS alone had a mean histology score of 8.4 (FIG. 20). In comparison, mice that were given anti-CD83 antibodies had significantly reduced histology scores. Use of 39A2, 42C6, or 60B10 antibodies resulted in a mean histology score of 5.3, 5.5, or 5.4, respectively.

What is claimed is:

1. A method for treating an autoimmune disease in an individual comprising administering to the individual an effective amount of an anti-CD83 agonist antibody, wherein the autoimmune disease is selected from the group consisting of multiple sclerosis, ulcerative colitis, inflammatory bowel disease, Crohn's disease, psoriasis, vasculitis, and diabetes mellitus, and wherein the anti-CD83 agonist antibody has one or more of the following characteristics: inhibits release of a pro-inflammatory cytokine from mature dendritic cells, induces release of an anti-inflammatory cytokine from mature dendritic cells, induces a decrease of cell surface expression of CD83 and/or HLA-DR on mature dendritic cells, and inhibits activation of MAPK and/or mTOR signaling in mature dendritic cells.

2. The method of claim 1, wherein the individual has an autoimmune disease associated with myeloid cell activation.

3. The method of claim 2, wherein the individual has Crohn's disease.

4. The method of claim 2, wherein the individual has ulcerative colitis.

5. The method of claim 1, wherein the individual is a human.

6. The method of claim 1, wherein the anti-CD83 agonist antibody inhibits release of a pro-inflammatory cytokine from mature dendritic cells.

7. The method of claim 6, wherein the release of pro-inflammatory cytokine MCP-1 and/or IL-12p40 are inhibited.

8. The method of claim 1, wherein the anti-CD83 agonist antibody induces release of an anti-inflammatory cytokine from mature dendritic cells.

9. The method of claim 8, wherein the release of anti-inflammatory cytokine IL-1 ra is induced.

10. The method of claim 1, wherein the anti-CD83 agonist antibody induces a decrease of cell surface expression of CD83 and/or HLA-DR on mature dendritic cells.

11. The method of claim 1, wherein the anti-CD83 agonist antibody inhibits activation of MAPK and/or mTOR signaling in mature dendritic cells.

12. The method of claim 11, wherein the inhibition of the activation of MAPK signaling is measured by a decrease in phosphorylation of p38 and CREB proteins in mature dendritic cells.

13. The method of claim 11, wherein the inhibition of the activation of mTOR signaling is measured by a decrease in phosphorylation of the mTOR protein in mature dendritic cells.

14. The method of claim 1, wherein the anti-CD83 agonist antibody is a monoclonal antibody.

15. The method of claim 14, wherein the anti-CD83 agonist antibody is an antibody fragment selected from the group consisting of Fab, Fab'-SH, Fv, scFv, and (Fab')$_2$ fragments.

16. The method of claim 1, wherein the anti-CD83 agonist antibody is a humanized antibody or a chimeric antibody.

17. The method of claim 1, wherein the anti-CD83 agonist antibody comprises a heavy chain variable domain comprising (a) HVR-H1 comprising the amino acid sequence of SEQ ID NO:31, (b) HVR-H2 comprising the amino acid sequence of SEQ ID NO:32, and (c) HVR-H3 comprising the amino acid sequence of SEQ ID NO:33; and a light chain variable domain comprising (a) HVR-L1 comprising the amino acid sequence of SEQ ID NO:37, (b) HVR-L2 comprising the amino acid sequence of SEQ ID NO:38, and (c) HVR-L3 comprising the amino acid sequence of SEQ ID NO:39.

18. The method of claim 1, wherein the antibody comprises a heavy chain variable domain comprising the amino acid sequence of SEQ ID NO:30, and/or a light chain variable domain comprising the amino acid sequence of SEQ ID NO:36.

19. The method of claim 1, wherein the anti-CD83 agonist antibody is a human antibody.

20. The method of claim 1, wherein the anti-CD83 agonist antibody is administered intravenously, intramuscularly, subcutaneously, topically, orally, transdermally, intraperitoneally, intraorbitally, by implantation, by inhalation, intrathecally, intraventricularly, or intranasally.

21. An article of manufacture comprising an anti-CD83 agonist antibody and a package insert comprising instructions for using the anti-CD83 agonist antibody to treat an autoimmune disease in an individual, wherein the autoimmune disease is selected from the group consisting of multiple sclerosis, ulcerative colitis, inflammatory bowel disease, Crohn's disease, psoriasis, vasculitis, and diabetes mellitus, and wherein the anti-CD83 agonist antibody has one or more of the following characteristics: inhibits release of a pro-inflammatory cytokine from mature dendritic cells, induces release of an anti-inflammatory cytokine from mature dendritic cells, induces a decrease of cell surface expression of CD83 and/or HLA-DR on mature dendritic cells, and inhibits activation of MAPK and/or mTOR signaling in mature dendritic cells.

* * * * *

SEQUENCE LISTING

```
<160> NUMBER OF SEQ ID NOS: 44

<210> SEQ ID NO 1
<211> LENGTH: 205
<212> TYPE: PRT
<213> ORGANISM: Homo sapiens

<400> SEQUENCE: 1

Met Ser Arg Gly Leu Gln Leu Leu Leu Ser Cys Ala Tyr Ser Leu
 1               5                  10                  15

Ala Pro Ala Thr Pro Glu Val Lys Val Ala Cys Ser Glu Asp Val Asp
                20                  25                  30

Leu Pro Cys Thr Ala Pro Trp Asp Pro Gln Val Pro Tyr Thr Val Ser
                35                  40                  45

Trp Val Lys Leu Leu Glu Gly Gly Glu Glu Arg Met Glu Thr Pro Gln
    50                  55                  60

Glu Asp His Leu Arg Gly Gln His Tyr His Gln Lys Gly Gln Asn Gly
 65                 70                  75                  80

Ser Phe Asp Ala Pro Asn Glu Arg Pro Tyr Ser Leu Lys Ile Arg Asn
                85                  90                  95

Thr Thr Ser Cys Asn Ser Gly Thr Tyr Arg Cys Thr Leu Gln Asp Pro
                100                 105                 110

Asp Gly Gln Arg Asn Leu Ser Gly Lys Val Ile Leu Arg Val Thr Gly
                115                 120                 125

Cys Pro Ala Gln Arg Lys Glu Glu Thr Phe Lys Lys Tyr Arg Ala Glu
                130                 135                 140

Ile Val Leu Leu Leu Ala Leu Val Ile Phe Tyr Leu Thr Leu Ile Ile
145                 150                 155                 160

Phe Thr Cys Lys Phe Ala Arg Leu Gln Ser Ile Phe Pro Asp Phe Ser
                165                 170                 175

Lys Ala Gly Met Glu Arg Ala Phe Leu Pro Val Thr Ser Pro Asn Lys
                180                 185                 190

His Leu Gly Leu Val Thr Pro His Lys Thr Glu Leu Val
                195                 200                 205
```

```
<210> SEQ ID NO 2
<211> LENGTH: 121
<212> TYPE: PRT
<213> ORGANISM: Homo sapiens

<400> SEQUENCE: 2

Thr Pro Glu Val Lys Val Ala Cys Ser Glu Asp Val Asp Leu Pro Cys
  1               5                  10                  15

Thr Ala Pro Trp Asp Pro Gln Val Pro Tyr Thr Val Ser Trp Val Lys
             20                  25                  30

Leu Leu Glu Gly Gly Glu Glu Arg Met Glu Thr Pro Gln Glu Asp His
         35                  40                  45

Leu Arg Gly Gln His Tyr His Gln Lys Gly Gln Asn Gly Ser Phe Asp
     50                  55                  60

Ala Pro Asn Glu Arg Pro Tyr Ser Leu Lys Ile Arg Asn Thr Thr Ser
 65                  70                  75                  80

Cys Asn Ser Gly Thr Tyr Arg Cys Thr Leu Gln Asp Pro Asp Gly Gln
                 85                  90                  95

Arg Asn Leu Ser Gly Lys Val Ile Leu Arg Val Thr Gly Cys Pro Ala
            100                 105                 110

Gln Arg Lys Glu Glu Thr Phe Lys Lys
        115                 120

<210> SEQ ID NO 3
<211> LENGTH: 358
<212> TYPE: PRT
<213> ORGANISM: Artificial Sequence
<220> FEATURE:
<223> OTHER INFORMATION: Synthetic Construct

<400> SEQUENCE: 3

Thr Pro Glu Val Lys Val Ala Cys Ser Glu Asp Val Asp Leu Pro Cys
  1               5                  10                  15

Thr Ala Pro Trp Asp Pro Gln Val Pro Tyr Thr Val Ser Trp Val Lys
             20                  25                  30

Leu Leu Glu Gly Gly Glu Glu Arg Met Glu Thr Pro Gln Glu Asp His
         35                  40                  45

Leu Arg Gly Gln His Tyr His Gln Lys Gly Gln Asn Gly Ser Phe Asp
     50                  55                  60

Ala Pro Asn Glu Arg Pro Tyr Ser Leu Lys Ile Arg Asn Thr Thr Ser
 65                  70                  75                  80

Cys Asn Ser Gly Thr Tyr Arg Cys Thr Leu Gln Asp Pro Asp Gly Gln
                 85                  90                  95

Arg Asn Leu Ser Gly Lys Val Ile Leu Arg Val Thr Gly Cys Pro Ala
            100                 105                 110

Gln Arg Lys Glu Glu Thr Phe Lys Lys Tyr Gly Arg Ala Gln Val Thr
        115                 120                 125

Asp Lys Ala Ala His Tyr Thr Leu Cys Pro Pro Cys Pro Ala Pro Glu
    130                 135                 140

Leu Leu Gly Gly Pro Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser His Glu Asp Pro Glu Val Lys Phe Asn Trp Tyr Val Asp Gly
            180                 185                 190

Val Glu Val His Asn Ala Lys Thr Lys Pro Arg Glu Glu Gln Tyr Asn
        195                 200                 205
```

```
Ser Thr Tyr Arg Val Val Ser Val Leu Thr Val Leu His Gln Asp Trp
            210                 215                 220

Leu Asn Gly Lys Glu Tyr Lys Cys Lys Val Ser Asn Lys Ala Leu Pro
225                 230                 235                 240

Ala Pro Ile Glu Lys Thr Ile Ser Lys Ala Lys Gly Gln Pro Arg Glu
                245                 250                 255

Pro Gln Val Tyr Thr Leu Pro Pro Ser Arg Glu Glu Met Thr Lys Asn
            260                 265                 270

Gln Val Ser Leu Thr Cys Leu Val Lys Gly Phe Tyr Pro Ser Asp Ile
        275                 280                 285

Ala Val Glu Trp Glu Ser Asn Gly Gln Pro Glu Asn Asn Tyr Lys Thr
    290                 295                 300

Thr Pro Pro Val Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
            340                 345                 350

Ser Leu Ser Pro Gly Lys
        355

<210> SEQ ID NO 4
<211> LENGTH: 1344
<212> TYPE: DNA
<213> ORGANISM: Artificial Sequence
<220> FEATURE:
<223> OTHER INFORMATION: Synthetic Construct

<400> SEQUENCE: 4
caggtgcagc tgaaggagtc aggacctggc ctagtgaagc cctcacagtc aatgtccctc    60
acttgctctg tcaatggttt ctccatcacc agtcgttact ggtggacctg gatcaggcag   120
ttcccaggga agaacctgga gtggatgggt tacataagtt atagtggtgg caccagctac   180
aacccctccc tcaagagccg catctccatc acccgagaca catccaagaa ccagttcttc   240
ctgcacctga actctgtgac cactgctgac acagccacat attactgtgc aagagatctc   300
tacggtacct actttgatta ctggggccaa ggaaccctgg tcaccgtctc ctcagcctcc   360
accaagggcc catcggtcta tccactggct cctgtgtgtg gagatacaac tggctcctcg   420
gtgactctag gatgcctggt caagggttat ttccctgagc cagtgacctt gacctggaac   480
tctggatccc tgtccagtgg tgtgcacacc ttcccagctg tcctgcagtc tgacctctac   540
accctcagca gctcagtgac tgtaacctcg agcacctggc ccagccagtc catcacctgc   600
aatgtggccc accggcaag cagcaccaag gtggacaaga aaattgagcc cagaggaccc   660
acaatcaagc cctgtcctcc atgcaaatgc ccagcaccta acctcttggg tggaccatcc   720
gtcttcatct tccctccaaa gatcaaggat gtactcatga tctcccctga gccccatagtc   780 acatgtgtgg tggtggatgt gagcgaggat gacccagatg tccagatcag ctggtttgtg   840
aacaacgtgg aagtacacac agctcagaca caaacccata gagaggatta caacagtact   900
ctacgcgtgt cagtgccct ccccatccag caccaggact ggatgagtgg caaggagttc   960
aaatgcaagg tcaacaacaa agacctccca gcgcccatcg agaaccat ctcaaaaccc     1020 aaagggtcag taagagctcc acaggtatat gtcttgcctc caccagaaga agagatgact   1080
aagaaacagg tcactctgac ctgcatggtc acagacttca tgcctgaaga catttacgtg   1140
```

```
gagtggacca caacgggaa acagagcta actacaaga acactgaacc agtcctggac     1200
tctgatggtt cttacttcat gtacagcaag ctgagagtgg aaaagaagaa ctgggtggaa     1260
agaaatagct actcctgttc agtggtccac gagggtctgc acaatcacca cacgactaag     1320
agcttctccc ggactccggg taaa                                             1344
```

<210> SEQ ID NO 5
<211> LENGTH: 448
<212> TYPE: PRT
<213> ORGANISM: Artificial Sequence
<220> FEATURE:
<223> OTHER INFORMATION: Synthetic Construct

<400> SEQUENCE: 5

```
Gln Val Gln Leu Lys Glu Ser Gly Pro Gly Leu Val Lys Pro Ser Gln
1               5                   10                  15

Ser Met Ser Leu Thr Cys Ser Val Asn Gly Phe Ser Ile Thr Ser Arg
            20                  25                  30

Tyr Trp Trp Thr Trp Ile Arg Gln Phe Pro Gly Lys Asn Leu Glu Trp
        35                  40                  45

Met Gly Tyr Ile Ser Tyr Ser Gly Gly Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu His Leu Asn Ser Val Thr Thr Ala Asp Thr Ala Thr Tyr Tyr Cys
                85                  90                  95

Ala Arg Asp Leu Tyr Gly Thr Tyr Phe Asp Tyr Trp Gly Gln Gly Thr
            100                 105                 110

Leu Val Thr Val Ser Ser Ala Ser Thr Lys Gly Pro Ser Val Tyr Pro
        115                 120                 125

Leu Ala Pro Val Cys Gly Asp Thr Thr Gly Ser Ser Val Thr Leu Gly
    130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Thr Ser Ser Thr
            180                 185                 190

Trp Pro Ser Gln Ser Ile Thr Cys Asn Val Ala His Pro Ala Ser Ser
        195                 200                 205

Thr Lys Val Asp Lys Lys Ile Glu Pro Arg Gly Pro Thr Ile Lys Pro
    210                 215                 220

Cys Pro Pro Cys Lys Cys Pro Ala Pro Asn Leu Leu Gly Gly Pro Ser
225                 230                 235                 240

Val Phe Ile Phe Pro Pro Lys Ile Lys Asp Val Leu Met Ile Ser Leu
                245                 250                 255

Ser Pro Ile Val Thr Cys Val Val Val Asp Val Ser Glu Asp Asp Pro
            260                 265                 270

Asp Val Gln Ile Ser Trp Phe Val Asn Asn Val Glu Val His Thr Ala
        275                 280                 285

Gln Thr Gln Thr His Arg Glu Asp Tyr Asn Ser Thr Leu Arg Val Val
    290                 295                 300

Ser Ala Leu Pro Ile Gln His Gln Asp Trp Met Ser Gly Lys Glu Phe
305                 310                 315                 320

Lys Cys Lys Val Asn Asn Lys Asp Leu Pro Ala Pro Ile Glu Arg Thr
```

```
                    325                 330                 335
Ile Ser Lys Pro Lys Gly Ser Val Arg Ala Pro Gln Val Tyr Val Leu
                340                 345                 350

Pro Pro Pro Glu Glu Met Thr Lys Lys Gln Val Thr Leu Thr Cys
            355                 360                 365

Met Val Thr Asp Phe Met Pro Glu Asp Ile Tyr Val Glu Trp Thr Asn
        370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
                405                 410                 415

Asn Trp Val Glu Arg Asn Ser Tyr Ser Cys Ser Val Val His Glu Gly
            420                 425                 430

Leu His Asn His His Thr Thr Lys Ser Phe Ser Arg Thr Pro Gly Lys
        435                 440                 445

<210> SEQ ID NO 6
<211> LENGTH: 118
<212> TYPE: PRT
<213> ORGANISM: Artificial Sequence
<220> FEATURE:
<223> OTHER INFORMATION: Synthetic Construct

<400> SEQUENCE: 6

Gln Val Gln Leu Lys Glu Ser Gly Pro Gly Leu Val Lys Pro Ser Gln
1               5                   10                  15

Ser Met Ser Leu Thr Cys Ser Val Asn Gly Phe Ser Ile Thr Ser Arg
            20                  25                  30

Tyr Trp Trp Thr Trp Ile Arg Gln Phe Pro Gly Lys Asn Leu Glu Trp
        35                  40                  45

Met Gly Tyr Ile Ser Tyr Ser Gly Gly Thr Tyr Asn Pro Ser Leu
    50                  55                  60

Lys Ser Arg Ile Ser Ile Thr Arg Asp Thr Ser Lys Asn Gln Phe Phe
65                  70                  75                  80

Leu His Leu Asn Ser Val Thr Thr Ala Asp Thr Ala Thr Tyr Tyr Cys
                85                  90                  95

Ala Arg Asp Leu Tyr Gly Thr Tyr Phe Asp Tyr Trp Gly Gln Gly Thr
            100                 105                 110

Leu Val Thr Val Ser Ser
        115

<210> SEQ ID NO 7
<211> LENGTH: 11
<212> TYPE: PRT
<213> ORGANISM: Artificial Sequence
<220> FEATURE:
<223> OTHER INFORMATION: Synthetic Construct

<400> SEQUENCE: 7

Gly Phe Ser Ile Thr Ser Arg Tyr Trp Trp Thr
1               5                   10

<210> SEQ ID NO 8
<211> LENGTH: 17
<212> TYPE: PRT
<213> ORGANISM: Artificial Sequence
<220> FEATURE:
<223> OTHER INFORMATION: Synthetic Construct

<400> SEQUENCE: 8
```

Gly Tyr Ile Ser Tyr Ser Gly Gly Thr Ser Tyr Asn Pro Ser Leu Lys
1               5                   10                  15

Ser

<210> SEQ ID NO 9
<211> LENGTH: 11
<212> TYPE: PRT
<213> ORGANISM: Artificial Sequence
<220> FEATURE:
<223> OTHER INFORMATION: Synthetic Construct

<400> SEQUENCE: 9

Ala Arg Asp Leu Tyr Gly Thr Tyr Phe Asp Tyr
1               5                   10

<210> SEQ ID NO 10
<211> LENGTH: 639
<212> TYPE: DNA
<213> ORGANISM: Artificial Sequence
<220> FEATURE:
<223> OTHER INFORMATION: Synthetic Construct

<400> SEQUENCE: 10
cagtatgagc taattcagcc aaagtctgtg tcagagtctc tagggagaac agtcaccatc      60
tcctgcaaac gcagcagtgg caacattgga aataactatg tacactggta ccaacagcac     120
tttggaagct cacccaaaac tgtgatctat gatgacaata aagaccatc tggggttcct      180 cataggttct ctggctccat tgacagctcc tcaaactcag cttccctgac tatcactgat     240
ctgcagattg aagatgaagc tgaatactac tgtcaatctg cttgggtgtt cggttcaggc     300
accaaagtga ctgtcctacg cgctgatgct gcaccaactg tatccatctt cccaccatcc     360
agtgagcagt taacatctgg aggtgcctca gtcgtgtgct tcttgaacaa cttctacccc     420
aaagacatca atgtcaagtg gaagattgat ggcagtgaac gacaaaatgg cgtcctgaac     480
agttggactg atcaggacag caaagacagc acctacagca tgagcagcac cctcacgttg     540
accaaggacg agtatgaacg acataacagc tatacctgtg aggccactca caagacatca     600
acttcaccca ttgtcaagag cttcaacagg aatgagtgt                            639

<210> SEQ ID NO 11
<211> LENGTH: 213
<212> TYPE: PRT
<213> ORGANISM: Artificial Sequence
<220> FEATURE:
<223> OTHER INFORMATION: Synthetic Construct

<400> SEQUENCE: 11

Gln Tyr Glu Leu Ile Gln Pro Lys Ser Val Ser Glu Ser Leu Gly Arg
1               5                   10                  15

Thr Val Thr Ile Ser Cys Lys Arg Ser Ser Gly Asn Ile Gly Asn Asn
                20                  25                  30

Tyr Val His Trp Tyr Gln Gln His Phe Gly Ser Ser Pro Lys Thr Val
            35                  40                  45

Ile Tyr Asp Asp Asn Lys Arg Pro Ser Gly Val Pro His Arg Phe Ser
        50                  55                  60

Gly Ser Ile Asp Ser Ser Ser Asn Ser Ala Ser Leu Thr Ile Thr Asp
65                  70                  75                  80

Leu Gln Ile Glu Asp Glu Ala Glu Tyr Tyr Cys Gln Ser Ala Trp Val
                85                  90                  95

```
Phe Gly Ser Gly Thr Lys Val Thr Val Leu Arg Ala Asp Ala Ala Pro
                100                 105                 110
Thr Val Ser Ile Phe Pro Pro Ser Glu Gln Leu Thr Ser Gly Gly
            115                 120                 125
Ala Ser Val Val Cys Phe Leu Asn Asn Phe Tyr Pro Lys Asp Ile Asn
        130                 135                 140
Val Lys Trp Lys Ile Asp Gly Ser Glu Arg Gln Asn Gly Val Leu Asn
145                 150                 155                 160
Ser Trp Thr Asp Gln Asp Ser Lys Asp Ser Thr Tyr Ser Met Ser Ser
                165                 170                 175
Thr Leu Thr Leu Thr Lys Asp Glu Tyr Glu Arg His Asn Ser Tyr Thr
            180                 185                 190
Cys Glu Ala Thr His Lys Thr Ser Thr Ser Pro Ile Val Lys Ser Phe
        195                 200                 205
Asn Arg Asn Glu Cys
    210

<210> SEQ ID NO 12
<211> LENGTH: 106
<212> TYPE: PRT
<213> ORGANISM: Artificial Sequence
<220> FEATURE:
<223> OTHER INFORMATION: Synthetic Construct

<400> SEQUENCE: 12

Gln Tyr Glu Leu Ile Gln Pro Lys Ser Val Ser Glu Ser Leu Gly Arg
 1               5                  10                  15
Thr Val Thr Ile Ser Cys Lys Arg Ser Ser Gly Asn Ile Gly Asn Asn
            20                  25                  30
Tyr Val His Trp Tyr Gln Gln His Phe Gly Ser Ser Pro Lys Thr Val
        35                  40                  45
Ile Tyr Asp Asp Asn Lys Arg Pro Ser Gly Val Pro His Arg Phe Ser
    50                  55                  60
Gly Ser Ile Asp Ser Ser Ser Asn Ser Ala Ser Leu Thr Ile Thr Asp
65                  70                  75                  80
Leu Gln Ile Glu Asp Glu Ala Glu Tyr Tyr Cys Gln Ser Ala Trp Val
                85                  90                  95
Phe Gly Ser Gly Thr Lys Val Thr Val Leu
                100                 105

<210> SEQ ID NO 13
<211> LENGTH: 13
<212> TYPE: PRT
<213> ORGANISM: Artificial Sequence
<220> FEATURE:
<223> OTHER INFORMATION: Synthetic Construct

<400> SEQUENCE: 13

Lys Arg Ser Ser Gly Asn Ile Gly Asn Asn Tyr Val His
 1               5                  10

<210> SEQ ID NO 14
<211> LENGTH: 7
<212> TYPE: PRT
<213> ORGANISM: Artificial Sequence
<220> FEATURE:
<223> OTHER INFORMATION: Synthetic Construct

<400> SEQUENCE: 14

Asp Asp Asn Lys Arg Pro Ser
```

<210> SEQ ID NO 15
<211> LENGTH: 5
<212> TYPE: PRT
<213> ORGANISM: Artificial Sequence
<220> FEATURE:
<223> OTHER INFORMATION: Synthetic Construct

<400> SEQUENCE: 15

Gln Ser Ala Trp Val
 1               5

<210> SEQ ID NO 16
<211> LENGTH: 1344
<212> TYPE: DNA
<213> ORGANISM: Artificial Sequence
<220> FEATURE:
<223> OTHER INFORMATION: Synthetic Construct

<400> SEQUENCE: 16

```
caggtgcagc tgaaggagtc aggacctggc ctagtgaagc cctcacagtc aatgtccctc      60
acttgctctg tcaatggttt ctccatcacc agtcgttact ggtggacctg gatcaggcag     120
ttcccaggga agaacctgga gtggatgggt tacataagtt atagtggtgg caccagctac     180
aacccctccc tcaagagccg catctccatc acccgagaca tccaagaa ccagttcttc       240 ctgcacctga actctgtgac cactgctgac acagccacat attactgtgc aagagatctc     300
tacggtacct actttgatta ctggggccaa ggaaccatgg tcaccgtctc ctcagcctcc     360
accaagggcc catcggtcta tccactggct cctgtgtgtg agatacaac tggctcctcg      420 gtgactctag gatgcctggt caagggttat ttccctgagc cagtgacctt gacctggaac     480
tctggatccc tgtccagtgg tgtgcacacc ttcccagctg tcctgcagtc tgacctctac     540
accctcagca gctcagtgac tgtaacctcg agcacctggc ccagccagtc catcacctgc     600
aatgtggccc acccggcaag cagcaccaag gtggacaaga aaattgagcc cagaggaccc     660
acaatcaagc cctgtcctcc atgcaaatgc ccagcaccta acctcttggg tggaccatcc     720
gtcttcatct tccctccaaa gatcaaggat gtactcatga tctccctgag ccccatagtc     780
acatgtgtgg tggtggatgt gagcgaggat gacccagatg tccagatcag ctggtttgtg     840
aacaacgtgg aagtacacac agctcagaca caaacccata gagaggatta caacagtact     900
ctacgcgtgg tcagtgccct ccccatccag caccaggact ggatgagtgg caaggagttc     960
aaatgcaagg tcaacaacaa agacctccca gcgcccatcg agagaaccat ctcaaaaccc    1020
aaagggtcag taagagctcc acaggtatat gtcttgcctc caccagaaga agagatgact    1080
aagaaacagg tcactctgac ctgcatggtc acagacttca tgcctgaaga catttacgtg    1140
gagtggacca caacgggaa aacagagcta aactacaaga cactgaacc agtcctggac     1200 tctgatggtt cttacttcat gtacagcaag ctgagagtgg aaaagaagaa ctgggtggaa    1260
agaaatagct actcctgttc agtggtccac gagggtctgc acaatcacca cacgactaag    1320
agcttctccc ggactccggg taaa                                           1344
```

<210> SEQ ID NO 17
<211> LENGTH: 448
<212> TYPE: PRT
<213> ORGANISM: Artificial Sequence
<220> FEATURE:
<223> OTHER INFORMATION: Synthetic Construct

<400> SEQUENCE: 17

```
Gln Val Gln Leu Lys Glu Ser Gly Pro Gly Leu Val Lys Pro Ser Gln
  1               5                  10                  15

Ser Met Ser Leu Thr Cys Ser Val Asn Gly Phe Ser Ile Thr Ser Arg
             20                  25                  30

Tyr Trp Trp Thr Trp Ile Arg Gln Phe Pro Gly Lys Asn Leu Glu Trp
         35                  40                  45

Met Gly Tyr Ile Ser Tyr Ser Gly Gly Thr Ser Tyr Asn Pro Ser Leu
     50                  55                  60

Lys Ser Arg Ile Ser Ile Thr Arg Asp Thr Ser Lys Asn Gln Phe Phe
 65                  70                  75                  80

Leu His Leu Asn Ser Val Thr Ala Asp Thr Ala Thr Tyr Tyr Cys
                 85                  90                  95

Ala Arg Asp Leu Tyr Gly Thr Tyr Phe Asp Tyr Trp Gly Gln Gly Thr
                100                 105                 110

Met Val Thr Val Ser Ser Ala Ser Thr Lys Gly Pro Ser Val Tyr Pro
            115                 120                 125

Leu Ala Pro Val Cys Gly Asp Thr Thr Gly Ser Ser Val Thr Leu Gly
130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Thr Ser Ser Thr
            180                 185                 190

Trp Pro Ser Gln Ser Ile Thr Cys Asn Val Ala His Pro Ala Ser Ser
        195                 200                 205

Thr Lys Val Asp Lys Lys Ile Glu Pro Arg Gly Pro Thr Ile Lys Pro
210                 215                 220

Cys Pro Pro Cys Lys Cys Pro Ala Pro Asn Leu Leu Gly Gly Pro Ser
225                 230                 235                 240

Val Phe Ile Phe Pro Pro Lys Ile Lys Asp Val Leu Met Ile Ser Leu
                245                 250                 255

Ser Pro Ile Val Thr Cys Val Val Asp Val Ser Glu Asp Asp Pro
            260                 265                 270

Asp Val Gln Ile Ser Trp Phe Val Asn Asn Val Glu Val His Thr Ala
        275                 280                 285

Gln Thr Gln Thr His Arg Glu Asp Tyr Asn Ser Thr Leu Arg Val Val
    290                 295                 300

Ser Ala Leu Pro Ile Gln His Gln Asp Trp Met Ser Gly Lys Glu Phe
305                 310                 315                 320

Lys Cys Lys Val Asn Asn Lys Asp Leu Pro Ala Pro Ile Glu Arg Thr
                325                 330                 335

Ile Ser Lys Pro Lys Gly Ser Val Arg Ala Pro Gln Val Tyr Val Leu
            340                 345                 350

Pro Pro Pro Glu Glu Glu Met Thr Lys Lys Gln Val Thr Leu Thr Cys
        355                 360                 365

Met Val Thr Asp Phe Met Pro Glu Asp Ile Tyr Val Glu Trp Thr Asn
    370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
                405                 410                 415
```

```
Asn Trp Val Glu Arg Asn Ser Tyr Ser Cys Ser Val Val His Glu Gly
                420                 425                 430

Leu His Asn His His Thr Thr Lys Ser Phe Ser Arg Thr Pro Gly Lys
        435                 440                 445

<210> SEQ ID NO 18
<211> LENGTH: 118
<212> TYPE: PRT
<213> ORGANISM: Artificial Sequence
<220> FEATURE:
<223> OTHER INFORMATION: Synthetic Construct

<400> SEQUENCE: 18

Gln Val Gln Leu Lys Glu Ser Gly Pro Gly Leu Val Lys Pro Ser Gln
 1               5                  10                  15

Ser Met Ser Leu Thr Cys Ser Val Asn Gly Phe Ser Ile Thr Ser Arg
            20                  25                  30

Tyr Trp Trp Thr Trp Ile Arg Gln Phe Pro Gly Lys Asn Leu Glu Trp
        35                  40                  45

Met Gly Tyr Ile Ser Tyr Ser Gly Gly Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu His Leu Asn Ser Val Thr Thr Ala Asp Thr Ala Thr Tyr Tyr Cys
                85                  90                  95

Ala Arg Asp Leu Tyr Gly Thr Tyr Phe Asp Tyr Trp Gly Gln Gly Thr
            100                 105                 110

Met Val Thr Val Ser Ser
        115

<210> SEQ ID NO 19
<211> LENGTH: 11
<212> TYPE: PRT
<213> ORGANISM: Artificial Sequence
<220> FEATURE:
<223> OTHER INFORMATION: Synthetic Construct

<400> SEQUENCE: 19

Gly Phe Ser Ile Thr Ser Arg Tyr Trp Trp Thr
 1               5                  10

<210> SEQ ID NO 20
<211> LENGTH: 17
<212> TYPE: PRT
<213> ORGANISM: Artificial Sequence
<220> FEATURE:
<223> OTHER INFORMATION: Synthetic Construct

<400> SEQUENCE: 20

Gly Tyr Ile Ser Tyr Ser Gly Gly Thr Ser Tyr Asn Pro Ser Leu Lys
 1               5                  10                  15

Ser

<210> SEQ ID NO 21
<211> LENGTH: 11
<212> TYPE: PRT
<213> ORGANISM: Artificial Sequence
<220> FEATURE:
<223> OTHER INFORMATION: Synthetic Construct

<400> SEQUENCE: 21
```

Ala Arg Asp Leu Tyr Gly Thr Tyr Phe Asp Tyr
1               5                   10

<210> SEQ ID NO 22
<211> LENGTH: 639
<212> TYPE: DNA
<213> ORGANISM: Artificial Sequence
<220> FEATURE:
<223> OTHER INFORMATION: Synthetic Construct

<400> SEQUENCE: 22

```
cagtatgagc taattcagcc aaagtctgtg tcagagtctc tagggagaac agtcaccatc    60
tcctgcaaac gcagcagtgg caacattgga ataactatg  tacactggta ccaacagcac   120
tttggaagct cacccaaaac tgtgatctat gatgacaata aagaccatc  tggggttcct   180
cataggttct ctggctccat tgacagctcc tcaaactcag cttccctgac tatcactgat   240
ctgcagattg aagatgaagc tgaatactac tgtcaatctg cttgggtgtt cggttcaggc   300
accaaagtga ctgtcctacg cgctgatgct gcaccaactg tatccatctt cccaccatcc   360
agtgagcagt taacatctgg aggtgcctca gtcgtgtgct tcttgaacaa cttctacccc   420
aaagacatca atgtcaagtg gaagattgat ggcagtgaac gacaaaatgg cgtcctgaac   480
agttggactg atcaggacag caaagacagc acctacagca tgagcagcac cctcacgttg   540
accaaggacg agtatgaacg acataacagc tatacctgtg aggccactca caagacatca   600
acttcaccca ttgtcaagag cttcaacagg aatgagtgt                           639
```

<210> SEQ ID NO 23
<211> LENGTH: 213
<212> TYPE: PRT
<213> ORGANISM: Artificial Sequence
<220> FEATURE:
<223> OTHER INFORMATION: Synthetic Construct

<400> SEQUENCE: 23

Gln Tyr Glu Leu Ile Gln Pro Lys Ser Val Ser Glu Ser Leu Gly Arg
1               5                   10                  15

Thr Val Thr Ile Ser Cys Lys Arg Ser Ser Gly Asn Ile Gly Asn Asn
            20                  25                  30

Tyr Val His Trp Tyr Gln Gln His Phe Gly Ser Ser Pro Lys Thr Val
        35                  40                  45

Ile Tyr Asp Asp Asn Lys Arg Pro Ser Gly Val Pro His Arg Phe Ser
    50                  55                  60

Gly Ser Ile Asp Ser Ser Ser Asn Ser Ala Ser Leu Thr Ile Thr Asp
65                  70                  75                  80

Leu Gln Ile Glu Asp Glu Ala Glu Tyr Tyr Cys Gln Ser Ala Trp Val
                85                  90                  95

Phe Gly Ser Gly Thr Lys Val Thr Val Leu Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr

```
                    180                 185                 190
Cys Glu Ala Thr His Lys Thr Ser Thr Ser Pro Ile Val Lys Ser Phe
            195                 200                 205

Asn Arg Asn Glu Cys
    210
```

<210> SEQ ID NO 24
<211> LENGTH: 106
<212> TYPE: PRT
<213> ORGANISM: Artificial Sequence
<220> FEATURE:
<223> OTHER INFORMATION: Synthetic Construct

<400> SEQUENCE: 24

```
Gln Tyr Glu Leu Ile Gln Pro Lys Ser Val Ser Glu Ser Leu Gly Arg
1               5                   10                  15

Thr Val Thr Ile Ser Cys Lys Arg Ser Ser Gly Asn Ile Gly Asn Asn
            20                  25                  30

Tyr Val His Trp Tyr Gln Gln His Phe Gly Ser Ser Pro Lys Thr Val
        35                  40                  45

Ile Tyr Asp Asp Asn Lys Arg Pro Ser Gly Val Pro His Arg Phe Ser
50                  55                  60

Gly Ser Ile Asp Ser Ser Asn Ser Ala Ser Leu Thr Ile Thr Asp
65                  70                  75                  80

Leu Gln Ile Glu Asp Glu Ala Glu Tyr Tyr Cys Gln Ser Ala Trp Val
                85                  90                  95

Phe Gly Ser Gly Thr Lys Val Thr Val Leu
            100                 105
```

<210> SEQ ID NO 25
<211> LENGTH: 13
<212> TYPE: PRT
<213> ORGANISM: Artificial Sequence
<220> FEATURE:
<223> OTHER INFORMATION: Synthetic Construct

<400> SEQUENCE: 25

```
Lys Arg Ser Ser Gly Asn Ile Gly Asn Asn Tyr Val His
1               5                   10
```

<210> SEQ ID NO 26
<211> LENGTH: 7
<212> TYPE: PRT
<213> ORGANISM: Artificial Sequence
<220> FEATURE:
<223> OTHER INFORMATION: Synthetic Construct

<400> SEQUENCE: 26

```
Asp Asp Asn Lys Arg Pro Ser
1               5
```

<210> SEQ ID NO 27
<211> LENGTH: 5
<212> TYPE: PRT
<213> ORGANISM: Artificial Sequence
<220> FEATURE:
<223> OTHER INFORMATION: Synthetic Construct

<400> SEQUENCE: 27

```
Gln Ser Ala Trp Val
1               5
```

<210> SEQ ID NO 28
<211> LENGTH: 1350
<212> TYPE: DNA
<213> ORGANISM: Artificial Sequence
<220> FEATURE:
<223> OTHER INFORMATION: Synthetic Construct

<400> SEQUENCE: 28

```
caggtgcagc tgaaggagtc aggacctggc ctcgtgaagc cctcacagtc actgtccctc      60
acttgctctg tcactggttt ctccatcacc accggtggtt actggtggac ctggatcagg     120
cagttcccag ggcagaagct ggagtggatg ggtacatat ttagtagtgg taacaccaac      180
tacaacccat ccatcaagag ccgcatctcc ataaccagag acacatccaa gaaccagttc     240
ttcctgcagc tgaactctgt gactactgag ggggacacag ccagatatta ttgtgcaagg     300
gcctacggta agctaggctt tgattactgg ggccaaggaa ccctggtcac cgtctcctca     360
gcctccacca agggcccatc ggtctatcca ctggctcctg tgtgtggaga tacaactggc     420
tcctcggtga ctctaggatg cctggtcaag ggttatttcc ctgagccagt gaccttgacc     480
tggaactctg gatccctgtc cagtggtgtg cacaccttcc cagctgtcct gcagtctgac     540
ctctacaccc tcagcagctc agtgactgta acctcgagca cctggcccag ccagtccatc     600
acctgcaatg tggcccaccc ggcaagcagc accaaggtgg acaagaaaat tgagcccaga     660
ggacccacaa tcaagccctg tcctccatgc aaatgcccag cacctaacct cttgggtgga     720
ccatccgtct tcatcttccc tccaaagatc aaggatgtac tcatgatctc cctgagcccc     780
atagtcacat gtgtggtggt ggatgtgagc gaggatgacc cagatgtcca gatcagctgg     840
tttgtgaaca acgtggaagt acacacagct cagacacaaa cccatagaga ggattacaac     900
agtactctac gcgtggtcag tgccctcccc atccagcacc aggactggat gagtggcaag     960
gagttcaaat gcaaggtcaa caacaaagac ctcccagcgc ccatcgagag aaccatctca    1020
aaacccaaag ggtcagtaag agctccacag gtatatgtct tgcctccacc agaagaagag    1080
atgactaaga aacaggtcac tctgacctgc atggtcacag acttcatgcc tgaagacatt    1140
tacgtggagt ggaccaacaa cgggaaaaca gagctaaact acaagaacac tgaaccagtc    1200
ctggactctg atggttctta cttcatgtac agcaagctga gagtggaaaa gaagaactgg    1260
gtggaaagaa atagctactc ctgttcagtg gtccacgagg gtctgcacaa tcaccacacg    1320
actaagagct ctcccggac tccgggtaaa                                      1350
```

<210> SEQ ID NO 29
<211> LENGTH: 450
<212> TYPE: PRT
<213> ORGANISM: Artificial Sequence
<220> FEATURE:
<223> OTHER INFORMATION: Synthetic Construct

<400> SEQUENCE: 29

```
Gln Val Gln Leu Lys Glu Ser Gly Pro Gly Leu Val Lys Pro Ser Gln
  1               5                  10                  15

Ser Leu Ser Leu Thr Cys Ser Val Thr Gly Phe Ser Ile Thr Thr Gly
             20                  25                  30

Gly Tyr Trp Trp Thr Trp Ile Arg Gln Phe Pro Gly Gln Lys Leu Glu
         35                  40                  45

Trp Met Gly Tyr Ile Phe Ser Ser Gly Asn Thr Asn Tyr Asn Pro Ser
     50                  55                  60

Ile Lys Ser Arg Ile Ser Ile Thr Arg Asp Thr Ser Lys Asn Gln Phe
 65                  70                  75                  80
```

```
Phe Leu Gln Leu Asn Ser Val Thr Thr Glu Gly Asp Thr Ala Arg Tyr
                85                  90                  95

Tyr Cys Ala Arg Ala Tyr Gly Lys Leu Gly Phe Asp Tyr Trp Gly Gln
            100                 105                 110

Gly Thr Leu Val Thr Val Ser Ser Ala Ser Thr Lys Gly Pro Ser Val
            115                 120                 125

Tyr Pro Leu Ala Pro Val Cys Gly Asp Thr Thr Gly Ser Ser Val Thr
        130                 135                 140

Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Thr Ser
            180                 185                 190

Ser Thr Trp Pro Ser Gln Ser Ile Thr Cys Asn Val Ala His Pro Ala
        195                 200                 205

Ser Ser Thr Lys Val Asp Lys Lys Ile Glu Pro Arg Gly Pro Thr Ile
210                 215                 220

Lys Pro Cys Pro Pro Cys Lys Cys Pro Ala Pro Asn Leu Leu Gly Gly
225                 230                 235                 240

Pro Ser Val Phe Ile Phe Pro Pro Lys Ile Lys Asp Val Leu Met Ile
                245                 250                 255

Ser Leu Ser Pro Ile Val Thr Cys Val Val Asp Val Ser Glu Asp
            260                 265                 270

Asp Pro Asp Val Gln Ile Ser Trp Phe Val Asn Asn Val Glu Val His
        275                 280                 285

Thr Ala Gln Thr Gln Thr His Arg Glu Asp Tyr Asn Ser Thr Leu Arg
290                 295                 300

Val Val Ser Ala Leu Pro Ile Gln His Gln Asp Trp Met Ser Gly Lys
305                 310                 315                 320

Glu Phe Lys Cys Lys Val Asn Asn Lys Asp Leu Pro Ala Pro Ile Glu
                325                 330                 335

Arg Thr Ile Ser Lys Pro Lys Gly Ser Val Arg Ala Pro Gln Val Tyr
            340                 345                 350

Val Leu Pro Pro Pro Glu Glu Glu Met Thr Lys Lys Gln Val Thr Leu
        355                 360                 365

Thr Cys Met Val Thr Asp Phe Met Pro Glu Asp Ile Tyr Val Glu Trp
370                 375                 380

Thr Asn Asn Gly Lys Thr Glu Leu Asn Tyr Lys Asn Thr Glu Pro Val
385                 390                 395                 400

Leu Asp Ser Asp Gly Ser Tyr Phe Met Tyr Ser Lys Leu Arg Val Glu
                405                 410                 415

Lys Lys Asn Trp Val Glu Arg Asn Ser Tyr Ser Cys Ser Val Val His
            420                 425                 430

Glu Gly Leu His Asn His His Thr Thr Lys Ser Phe Ser Arg Thr Pro
        435                 440                 445

Gly Lys
    450

<210> SEQ ID NO 30
<211> LENGTH: 120
<212> TYPE: PRT
<213> ORGANISM: Artificial Sequence
<220> FEATURE:
```

<223> OTHER INFORMATION: Synthetic Construct

<400> SEQUENCE: 30

Gln Val Gln Leu Lys Glu Ser Gly Pro Gly Leu Val Lys Pro Ser Gln
1               5                   10                  15

Ser Leu Ser Leu Thr Cys Ser Val Thr Gly Phe Ser Ile Thr Thr Gly
            20                  25                  30

Gly Tyr Trp Trp Thr Trp Ile Arg Gln Phe Pro Gly Gln Lys Leu Glu
        35                  40                  45

Trp Met Gly Tyr Ile Phe Ser Ser Gly Asn Thr Asn Tyr Asn Pro Ser
    50                  55                  60

Ile Lys Ser Arg Ile Ser Ile Thr Arg Asp Thr Ser Lys Asn Gln Phe
65                  70                  75                  80

Phe Leu Gln Leu Asn Ser Val Thr Thr Glu Gly Asp Thr Ala Arg Tyr
                85                  90                  95

Tyr Cys Ala Arg Ala Tyr Gly Lys Leu Gly Phe Asp Tyr Trp Gly Gln
                100                 105                 110

Gly Thr Leu Val Thr Val Ser Ser
        115                 120

<210> SEQ ID NO 31
<211> LENGTH: 12
<212> TYPE: PRT
<213> ORGANISM: Artificial Sequence
<220> FEATURE:
<223> OTHER INFORMATION: Synthetic Construct

<400> SEQUENCE: 31

Gly Phe Ser Ile Thr Thr Gly Gly Tyr Trp Trp Thr
1               5                   10

<210> SEQ ID NO 32
<211> LENGTH: 17
<212> TYPE: PRT
<213> ORGANISM: Artificial Sequence
<220> FEATURE:
<223> OTHER INFORMATION: Synthetic Construct

<400> SEQUENCE: 32

Gly Tyr Ile Phe Ser Ser Gly Asn Thr Asn Tyr Asn Pro Ser Ile Lys
1               5                   10                  15

Ser

<210> SEQ ID NO 33
<211> LENGTH: 12
<212> TYPE: PRT
<213> ORGANISM: Artificial Sequence
<220> FEATURE:
<223> OTHER INFORMATION: Synthetic Construct

<400> SEQUENCE: 33

Cys Ala Arg Ala Tyr Gly Lys Leu Gly Phe Asp Tyr
1               5                   10

<210> SEQ ID NO 34
<211> LENGTH: 654
<212> TYPE: DNA
<213> ORGANISM: Artificial Sequence
<220> FEATURE:
<223> OTHER INFORMATION: Synthetic Construct

<400> SEQUENCE: 34

```
caacctgtgc tgactcagtc accctctgcc tctgcctccc tgggaaactc agtcaaaatc    60
acctgtaccc tgagtagtca gcacagcacc tataccattg gttggtacca gcaacatcca   120
gacaaggctc ctaagtatgt gatgtatgtt aatagtgatg gaagccacag caagggggat   180
gggatccctg atcgcttctc tggctccagc tctggggctc atcgttactt aagcatctcc   240
aacattcagc ctgaagatga agctgactat ttctgtggtt cttctgatag cagtgggtat   300 gttttttggca gcggaaccca gctcaccgtc ctacgcgctg atgctgcacc aactgtatcc   360
atcttcccac catccagtga gcagttaaca tctggaggtg cctcagtcgt gtgcttcttg   420
aacaacttct accccaaaga catcaatgtc aagtggaaga ttgatggcag tgaacgacaa   480
aatggcgtcc tgaacagttg gactgatcag gacagcaaag acagcaccta cagcatgagc   540 agcacccctca cgttgaccaa ggacgagtat gaacgacata cagctatac ctgtgaggcc   600 actcacaaga catcaacttc acccattgtc aagagcttca caggaatga gtgt           654
```

<210> SEQ ID NO 35
<211> LENGTH: 218
<212> TYPE: PRT
<213> ORGANISM: Artificial Sequence
<220> FEATURE:
<223> OTHER INFORMATION: Synthetic Construct

<400> SEQUENCE: 35

```
Gln Pro Val Leu Thr Gln Ser Pro Ser Ala Ser Ala Ser Leu Gly Asn
  1               5                  10                  15

Ser Val Lys Ile Thr Cys Thr Leu Ser Ser Gln His Ser Thr Tyr Thr
             20                  25                  30

Ile Gly Trp Tyr Gln Gln His Pro Asp Lys Ala Pro Lys Tyr Val Met
         35                  40                  45

Tyr Val Asn Ser Asp Gly Ser His Ser Lys Gly Asp Gly Ile Pro Asp
     50                  55                  60

Arg Phe Ser Gly Ser Ser Ser Gly Ala His Arg Tyr Leu Ser Ile Ser
 65                  70                  75                  80

Asn Ile Gln Pro Glu Asp Glu Ala Asp Tyr Phe Cys Gly Ser Ser Asp
                 85                  90                  95

Ser Ser Gly Tyr Val Phe Gly Ser Gly Thr Gln Leu Thr Val Leu Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215
```

<210> SEQ ID NO 36
<211> LENGTH: 111
<212> TYPE: PRT
<213> ORGANISM: Artificial Sequence
<220> FEATURE:
<223> OTHER INFORMATION: Synthetic Construct

<400> SEQUENCE: 36

Gln Pro Val Leu Thr Gln Ser Pro Ala Ser Ala Ser Leu Gly Asn
1               5                   10                  15

Ser Val Lys Ile Thr Cys Thr Leu Ser Ser Gln His Ser Thr Tyr Thr
            20                  25                  30

Ile Gly Trp Tyr Gln Gln His Pro Asp Lys Ala Pro Lys Tyr Val Met
        35                  40                  45

Tyr Val Asn Ser Asp Gly Ser His Ser Lys Gly Asp Gly Ile Pro Asp
    50                  55                  60

Arg Phe Ser Gly Ser Ser Ser Gly Ala His Arg Tyr Leu Ser Ile Ser
65                  70                  75                  80

Asn Ile Gln Pro Glu Asp Glu Ala Asp Tyr Phe Cys Gly Ser Ser Asp
                85                  90                  95

Ser Ser Gly Tyr Val Phe Gly Ser Gly Thr Gln Leu Thr Val Leu
            100                 105                 110

<210> SEQ ID NO 37
<211> LENGTH: 12
<212> TYPE: PRT
<213> ORGANISM: Artificial Sequence
<220> FEATURE:
<223> OTHER INFORMATION: Synthetic Construct

<400> SEQUENCE: 37

Thr Leu Ser Ser Gln His Ser Thr Tyr Thr Ile Gly
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Synthetic Construct

<400> SEQUENCE: 38

Val Asn Ser Asp Gly Ser His Ser Lys Gly Asp
1               5                   10

<210> SEQ ID NO 39
<211> LENGTH: 9
<212> TYPE: PRT
<213> ORGANISM: Artificial Sequence
<220> FEATURE:
<223> OTHER INFORMATION: Synthetic Construct

<400> SEQUENCE: 39

Gly Ser Ser Asp Ser Ser Gly Tyr Val
1               5

<210> SEQ ID NO 40
<211> LENGTH: 40
<212> TYPE: DNA
<213> ORGANISM: Artificial Sequence
<220> FEATURE:
<223> OTHER INFORMATION: Synthetic Construct

<400> SEQUENCE: 40
gatcaaacta gtccaccatg tcgcaaggcc tccagctcct                             40

<210> SEQ ID NO 41

```
<211> LENGTH: 36
<212> TYPE: DNA
<213> ORGANISM: Artificial Sequence
<220> FEATURE:
<223> OTHER INFORMATION: Synthetic Construct

<400> SEQUENCE: 41
catcatccgc ggtcataccg tttctgtctt aggaag                              36

<210> SEQ ID NO 42
<211> LENGTH: 158
<212> TYPE: DNA
<213> ORGANISM: Artificial Sequence
<220> FEATURE:
<223> OTHER INFORMATION: Synthetic Construct

<400> SEQUENCE: 42
gcggccgcga gcaactgata ttatatatgc cttgaacatg aaaccagggg caggctgtgg    60
aatatttcca ggcacgctgt ctcgaggcac agtagatcct caacccaagt ggataagaga  120
tgacaatagc tttccaagag agacagttat gagggacc                           158

<210> SEQ ID NO 43
<211> LENGTH: 415
<212> TYPE: DNA
<213> ORGANISM: Artificial Sequence
<220> FEATURE:
<223> OTHER INFORMATION: Synthetic Construct

<400> SEQUENCE: 43
acaggtctcc cagccagtgt ttctctcacc cctgcagggt gaaggctgtg ttggttcctg    60
gtgctacaat cacagcattg cagtcttatc ttgtttcaaa ataacttcgt ataatgtatg   120
ctatacgaag ttatctgttg acaattaatc atcggcatag tatatcggca tagtataata   180
cgacaaggtg aggaactaaa cccttcctcg tgctttacgg tatcgccgct cccgattcgc   240
agcgcatcgc cttctatcgc cttcttgacg agttcttctg aataacttcg tataatgtat   300
gctatacgaa gttatgcaaa cacagtctca agagttttta tagattctct tcttctcccc   360
tggaatcctc atttacaggg ataggggtg ggggagcacc ctgtcttgct ttaaa         415

<210> SEQ ID NO 44
<211> LENGTH: 450
<212> TYPE: DNA
<213> ORGANISM: Artificial Sequence
<220> FEATURE:
<223> OTHER INFORMATION: Synthetic Construct

<400> SEQUENCE: 44
ctcagtgaca cattacacac ttgtggtgca atgtatggat tacctgaata cccaccttcc    60
ccagggagca agcatttctc cgttttgtgc tttcttcagt gaagttccta ttctctagaa   120
agtataggaa cttcggtctg aagaggagtt acgtccagc caagctagct tggctgcagg    180
tcgtcgaaat tctaccgggt aggggctct atggcttctg aggcggaaag aaccagctgg    240
ggctcgacta gagcttgcgg aacccgaagt tcctattctc tagaaagtat aggaacttca   300
tcagtcaggt acatatataa cttcgtataa tgtatgctat acgaagttat gcacagtaga   360
tcctcaaccc aagtggataa gagatgacaa tagcttccca agagagacag ttatgaggga   420
ccacgcagaa atgaacaaag cacagttggt                                   450
```